United States Patent
Fan et al.

(10) Patent No.: US 12,350,353 B2
(45) Date of Patent: Jul. 8, 2025

(54) SYNTHETIC ENAMEL AND USES THEREOF

(71) Applicant: Trustees of Boston University, Boston, MA (US)

(72) Inventors: Yuwei Fan, Boston, MA (US); Lina Fahad N. Mengari, Boston, MA (US); Zhi Sun, Brighton, MA (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 0 days.

(21) Appl. No.: 18/511,294

(22) Filed: Nov. 16, 2023

(65) Prior Publication Data

US 2024/0156696 A1    May 16, 2024

Related U.S. Application Data

(60) Provisional application No. 63/425,842, filed on Nov. 16, 2022.

(51) Int. Cl.

| | | |
|---|---|---|
| *A61Q 11/00* | (2006.01) | |
| *A61K 8/21* | (2006.01) | |
| *A61K 8/24* | (2006.01) | |
| *A61K 8/27* | (2006.01) | |
| *A61K 8/36* | (2006.01) | |
| *A61K 31/185* | (2006.01) | |
| *A61K 33/06* | (2006.01) | |
| *A61K 33/16* | (2006.01) | |
| *A61K 33/42* | (2006.01) | |

(52) U.S. Cl.
CPC .................. *A61K 8/21* (2013.01); *A61K 8/24* (2013.01); *A61K 8/36* (2013.01); *A61K 31/185* (2013.01); *A61K 33/06* (2013.01); *A61K 33/16* (2013.01); *A61K 33/42* (2013.01); *A61Q 11/00* (2013.01); *A61K 2800/596* (2013.01); *A61K 2800/805* (2013.01); *A61K 2800/92* (2013.01)

(58) Field of Classification Search
CPC . A61Q 11/00; A61K 8/24; A61K 8/19; A61K 8/21; A61K 2800/92; A61K 8/27; A61K 8/55; A61K 9/0063
See application file for complete search history.

(56) References Cited

U.S. PATENT DOCUMENTS

| | | |
|---|---|---|
| 5,534,244 A | 7/1996 | Tung |
| 5,817,296 A | 10/1998 | Winston |
| 6,159,448 A | 12/2000 | Winston et al. |
| 6,485,708 B1 | 11/2002 | Winston et al. |
| 2010/0272764 A1 | 10/2010 | Latta et al. |
| 2014/0079750 A1 | 3/2014 | Li et al. |
| 2019/0216693 A1* | 7/2019 | Baig ................. A61K 8/24 |
| 2019/0365615 A1 | 12/2019 | García De Castro Andrews |
| 2021/0007948 A1 | 1/2021 | Baig et al. |

FOREIGN PATENT DOCUMENTS

CN         108096043 A  *  6/2018

OTHER PUBLICATIONS

Ionescu, et al., Dental tissue remineralization by bioactive calcium phosphate nanoparticles formulations. Scientific Reports, 12: 5994 (2022).

Thuy et al., Effect of strontium in combination with fluoride on enamel remineralization in vitro. Archives of Oral Biology, 53(11): 1017-22 (2008).

Wang, et al., Strontium ion can significantly decrease enamel demineralization and prevent the enamel surface hardness loss in acidic environment. 118(1): 39-49 (2019).

* cited by examiner

*Primary Examiner* — Tracy Liu
(74) *Attorney, Agent, or Firm* — NIXON PEABODY LLP; Ronald I. Eisenstein; Ravinderjit S. Braich

(57) ABSTRACT

The present disclosure relates to compositions and methods for restoring enamel, e.g., on tooth surfaces.

22 Claims, 37 Drawing Sheets

Side view on the fracture surface

Top view

Occluded dentin tubules after treatment

Open dentin tubules before treatment

Synthetic enamel crystal plug (between dotted lines) formed in a dentin tubule.

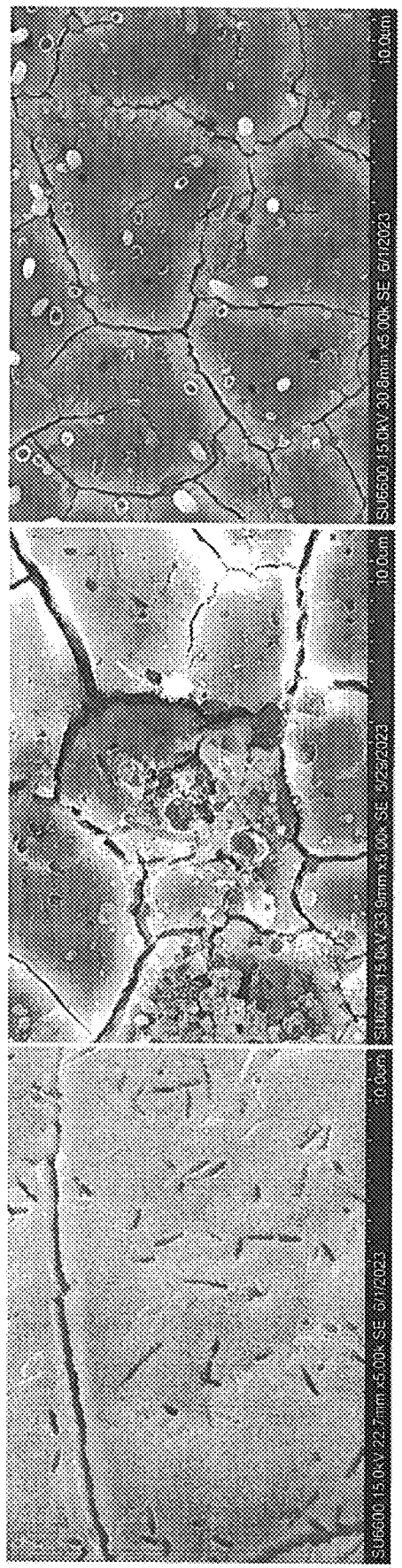

SYNTHETIC ENAMEL AND USES THEREOF

CROSS-REFERENCE TO RELATED APPLICATIONS

This application claims benefit under 35 U.S.C. § 119(e) of U.S. Provisional Application No. 63/425,842, filed Nov. 16, 2022, the contents of which are incorporated herein by reference in its entirety.

TECHNICAL FIELD

The present disclosure relates to compositions and methods for restoring enamel, e.g., on tooth surfaces. For example, compositions and methods can be used for restoring enamel on the surface of dentin, dentin tubules, root surface, root cannel, or cementum.

BACKGROUND

A tooth is a hard, calcified structure found in the mouths of many vertebrates and used to break down food. There are multiple layers in the formation of a tooth. The enamel is the outer-most layer of the tooth. Further in the tooth is the dentin layer, which accounts for most of the tooth's mass. It contains a mineral content of about 70%, which makes it harder than cementum and bone, but softer than enamel. In the center of the tooth is the pulp cavity, which contains the nerves and blood vessels important for tooth growth and function.

The enamel is the hardest substance in the human body and contains the highest percentage of minerals. The primary mineral is hydroxyapatite, which is a crystalline calcium phosphate. Once fully formed, enamel does not contain blood vessels or nerves, and is not made of cells. In humans, enamel varies in thickness over the surface of the tooth, often thickest at the cusp, up to 2.5 mm, and thinnest at its border with the cementum at the cementoenamel junction (CEJ).

Remineralization is the process of growing the enamel either on the surface of existing enamel or on the surface of dentin. It is the natural repair process for tooth lesions, (i.e., cavitated or non-cavitated) in which calcium, phosphate and sometimes fluoride ions are deposited into crystal voids in demineralized enamel. Remineralization occurs on a daily basis after attack by acids from food, through the presence of calcium, phosphate and fluoride found in saliva. Current treatments for remineralization include fluoride therapy, plaque control, diet, the use of xylitol, sorbitol, and erythritol to control the metabolism of bacteria, the use of biomimetic glass and ceramics in toothpaste to help remineralize teeth, and oligopeptide P11-4 which is used for biomimetic remineralization.

However, there remains a need in the art for improved remineralization compositions and methods for restoration of the enamel of teeth. The present disclosure addresses this need.

SUMMARY

In one aspect, provided herein is a remineralization composition. Generally, the composition has an ionic strength of from about 100 mM to about 500 mM and comprises strontium ions or stannous ions. For example, the composition has an ionic strength of from about 100 mM to about 500 mM and comprises strontium ions in a concentration about 0.05 ppm to about 300 ppm, or stannous ions in a concentration from about 0.1 ppm to about 50 ppm.

In some embodiments, the composition comprises calcium ions, phosphate ions, and fluoride ions. For example, the composition has an ionic strength of from about 100 mM to about 500 mM and comprises calcium ions, phosphate ions, and fluoride ions. The calcium ions can be present at a concentration from about 0.1 mM to about 500 mM. The phosphate ions can be present in a concentration from about 0.1 mM to about 100 mM. The fluoride ions can be present in a concentration from about 0.2 ppm to about 300 ppm. The strontium ions can be present in a concentration from about 0.05 ppm to about 300 ppm, e.g., in a concentration from about 20 ppm to about 100 ppm. The stannous ions can be present in a concentration from about 0.1 ppm to about 50 ppm, e.g., in a concentration from about 0.5 ppm to about 5 ppm.

In some embodiments of any one of the aspects described herein, the composition comprises calcium chloride, potassium phosphate, sodium fluoride and strontium acetate.

In some embodiments of any one of the aspects described herein, the composition comprises calcium chloride, potassium phosphate, sodium fluoride and stannous fluoride.

In embodiments of the various aspects described herein, the remineralization composition has a pH of from about 6 to about 8, e.g., from about 7 to about 7.5. For example, the composition can comprise a pH adjusting agent to adjust the pH to from about 6 to about 8, e.g., from about 7 to about 7.5 at room temperature.

In some embodiments, the composition comprises calcium ions in a concentration from about 2 mM to about 5 mM, phosphate ions in a concentration from about 0.5 mM to about 5 mM, fluoride ions in a concentration from about 2 ppm to about 20 ppm, and sodium ions in a concentration from about 150 mM to about 200 mM, and wherein the composition has a pH of from about 6.5 to about 7.5 and an ionic strength of from about 150 mM to about 200 mM, and wherein the composition comprises strontium in a concentration from about 10 ppm to about 200 ppm or stannous in a concentration from about 0.1 ppm to about 10 ppm. For example, the composition comprises from about 2 mM to about 3 mM calcium chloride, from about 1 mM to about 2 mM potassium dihydrogen phosphate, and from about 165 mM to about 175 mM sodium chloride, and wherein the composition has a pH of about 7.1 to about 7.4, and the composition further comprises: (i) from about 20 ppm to about 50 ppm strontium in strontium acetate and from about 5 ppm to about 15 ppm fluoride in sodium fluoride; or (ii) from about 0.1 ppm to about 1 ppm tin (II) in form of stannous fluoride and from about 1 ppm to about 3 ppm fluoride in sodium fluoride. In another example, the composition comprises from about 2 mM to about 3 mM calcium chloride, from about 1 mM to about 2 mM potassium dihydrogen phosphate, and from about 165 mM to about 175 mM sodium chloride, and wherein the composition has a pH of about 7.1 to about 7.4, and the composition further comprises: (i) from about 20 ppm to about 30 ppm strontium acetate and from about 5 ppm to about 15 ppm sodium fluoride; or (ii) from about 0.1 ppm to about 1 ppm stannous fluoride and from about 1 ppm to about 3 ppm sodium fluoride.

In some embodiments of any one of the aspects described herein, the comprises from about 2.5 mM calcium chloride, about 1.5 mM potassium dihydrogen phosphate, and from about 170 mM sodium chloride, and wherein the composition has a pH of about 7.3, and the composition further comprises: (a) about 25 ppm strontium in strontium acetate and from about 10 ppm fluoride in sodium fluoride; (b) about 0.5 ppm stannous fluoride and 2 ppm fluoride in sodium fluoride; (c) about 5 ppm strontium in strontium acetate and about 10 ppm fluoride in sodium fluoride; (d) about 10 ppm strontium in strontium acetate and about 5 ppm sodium fluoride; (e) about 10 ppm strontium in strontium acetate and about 10 ppm fluoride in sodium fluoride; (f) about 25 ppm strontium acetate and about 5 ppm sodium fluoride; (g) about 50 ppm strontium in strontium acetate and about 10 ppm fluoride in sodium fluoride; or (h) about 50 ppm strontium in strontium acetate and about 5 ppm fluoride in sodium fluoride. In another embodiment, the composition can comprise of 2.5 mM calcium chloride, about 1.5 mM potassium dihydrogen phosphate, and from about 170 mM sodium chloride, and wherein the composition has a pH of about 7.3, and the composition further comprises: about 25 ppm strontium acetate and from about 10 ppm sodium fluoride; (b) about 0.5 ppm stannous fluoride and 2 ppm sodium fluoride; (c) about 1 ppm strontium acetate and about 10 ppm sodium fluoride; (d) about 2 ppm strontium acetate and about 5 ppm sodium fluoride; (e) about 2 ppm strontium acetate and about 10 ppm sodium fluoride; (f) about 5 ppm strontium acetate and about 10 ppm sodium fluoride; (g) about 10 ppm strontium acetate and about 10 ppm sodium fluoride; or (h) about 2 ppm strontium acetate and about 5 ppm sodium fluoride.

In some embodiments of any one of the aspects described herein, the composition exhibits synergistic remineralization activity.

In some embodiments of any one of the aspects described herein, the composition can further comprise magnesium. For example, the composition can comprise magnesium in form of a magnesium salt, e.g., magnesium chloride. When present, the magnesium ions can be present in a concentration from about 1 ppm to about 50 ppm.

In some embodiments of any one of the aspects described herein, the composition can further comprise zinc. For example, zinc is in form of a zinc salt, e.g., zinc chloride. When present the zinc ions can be present in a concentration from about 1 ppm to about 50 ppm.

The remineralization compositions described herein can include a buffering agent. For example, the composition can comprise 4-(2-hydroxyethyl)-1 piperazineethanesulfonic acid (HEPES) as a buffering agent. When present the buffering agent can be present in a concentration up to about 150 mM. For example, the composition can comprise a buffering agent in a concentration from about 5 mM to about 150 mM. In another example, the composition can comprise a buffering agent in a concentration from about 10 mM to about 150 mM.

The remineralization compositions described herein can include additional components. For example, the remineralization compositions described herein can include one or more components used in oral care compositions. Such components include, but are not limited to flavoring agents, sweeteners, surfactants, thickening agents, anti-calculus agents, dental abrasive agents, binders, coloring agents, preservatives, and humectants.

Accordingly, in some embodiments of any one of the aspects described herein, the composition comprises a flavoring agent. When present, the flavoring agent can be present in an amount up to 5%, by weight of the composition. For example, the composition described herein can comprise a flavoring agent in an amount from about 0.01% to about 5%, by weight of the composition.

In some embodiments of any one of the aspects described herein, the remineralization composition further comprises a sweetener. When present, the sweetener can be present in an amount up to about 3%, by weight of the composition. For example, the composition comprises a sweetener in an amount from about 0.1% to about 3%, by weight of the composition.

The remineralization composition can also include a surfactant. The surfactant can be present in an amount up to about 2.5%, by weight of the composition. For example, the composition can comprise a surfactant in an amount from about 0.1% to about 2.5%, by weight of the composition. It is noted that a surfactant included in the composition can be an anionic, nonionic, cationic, zwitterionic or amphoteric surfactant.

In some embodiments of any one of the aspects described herein, the remineralization composition further comprises a thickening agent. When present, the thickening agent can be present in an amount up to about 5%, by weight of the composition. For example, the composition can comprise a thickening agent in an amount from about 0.1% to about 5%, by weight of the composition.

In some embodiments of any one of the aspects described herein, the remineralization composition further comprises an anti-calculus agent. For example, the remineralization composition comprises an anti-calculus agent in an amount up to about 15%, by weight of the composition. In some embodiments, the remineralization composition comprises an anti-calculus agent in an amount from about 0.1% to about 15%, by weight of the composition.

The remineralization compositions described herein can also comprise a dental abrasive agent. For example, the remineralization composition can comprise an abrasive agent in an amount up to about 50%, by weight of the composition, e.g., in an amount from about 5% to about 50%, by weight of the composition.

In some embodiments of any one of the aspects described herein, the remineralization composition further comprises a binder, optionally in an amount up to about 10%, by weight of the composition. For example, the remineralization composition comprises a binder in an amount from about 0.1% to about 10%, by weight of the composition.

In some embodiments of any one of the aspects described herein, the remineralization composition further comprises a coloring agent. The coloring agent can be present in an amount up to about 0.75%, by weight of the composition. For example, the remineralization composition can comprise a coloring agent an amount from about 0.01% to about 0.75%, by weight of the composition.

The remineralization composition described herein can also comprise a preservative. For example, the remineralization composition can comprise a preservative in an amount up to about 3%, by weight of the composition. In some embodiments of any one of the aspects described herein, the remineralization composition comprises a preservative in an amount from about 0.01% to about 3%, by weight of the composition.

In some embodiments of any one of the aspects described herein, the remineralization composition further comprises a humectant, optionally in an amount up to about 50%, by weight of the composition. For example, the remineralization composition comprises a humectant in an amount from about 10% to about 50%, by weight of the composition.

The remineralization composition can be formulated in any desire form. For example, the remineralization composition can be formulated as a solution, gel, suspension, slurry, paste, varnish, sealant or cement.

In some embodiments of any one of the aspects described herein, the remineralization composition is formulated as an oral care composition. Exemplary oral care compositions include, but are not limited to, mouthrinses, toothpastes, spray, foam, chewing gum and lozenges.

In some embodiments of any one of the aspects described herein, the remineralization composition can be present in a delivery device, such as a night guard, customer tray, aligner, sticky stripe, or microencapsulate with micro-pump. The remineralization composition can also be used as bonding agent additive, restorative material filler, or restorative matrix.

The remineralization compositions described herein can be used to grow enamel on damaged tooth surface, e.g., under physiological conditions. Accordingly, in another aspect, provided herein is a method for remineralizing a damaged dental surface. The method comprises contacting or applying, e.g., an effective amount of a remineralization composition described herein to a damaged dental surface. Exemplary damaged surfaces include, but are not limited to demineralization, decay, abrasion, superficial to moderate fractures, Non-Cavitated Caries Lesions (NCCL), and/or tooth discoloration.

Exposed dentin tubules in caries may cause tooth pain, bacterial infection, pulp inflammation, etc. Sealing dentin tubules is an important procedure in endodontic treatment and desensitization. Thus, the remineralization compositions described herein also can be used for dentin tube occlusion or sealing, tooth desensitization, root canal irrigation and/or sealing, enamel hardening, and/or fissure filling. Accordingly, in another aspect, provided herein is a method for dentin tube occlusion or sealing, tooth desensitization, root canal sealing, enamel hardening, and/or fissure filling. The method comprises contacting or applying, e.g., an effective amount of a remineralization composition described herein to a tooth in need thereof.

In some embodiments of any one of the aspects described herein, the step of applying the remineralization composition to teeth comprises administering to a subject's oral cavity a remineralization composition described herein.

Embodiments of the various aspects described herein are include a single-step chemical remineralization solution to grow new enamel on damaged tooth surface under physiological conditions. Without wishing to be bound by a theory, the newly formed enamel can integrate into the existing tooth structure to regenerate the hard tissues and restore the functions of the tooth. Different kinds of hard tissue damages of teeth such as demineralization, decay, abrasion, and/or superficial to moderate fracture can be treated. Further, the remineralization can be formed on top of existing natural or synthetic enamel. The remineralization also can be formed on top of an etched dentin surface. In some embodiments, one or more components of the mineralization composition can penetrate and establish enamel-like crystals at over 50 m deep inside dentin tubules.

Without wishing to be bound by a theory, the synthetic enamel formed using the remineralization compositions and methods described herein has the very close mineral density, chemical composition, crystal phases, hierarchical structure and hardness to the natural enamel. In various embodiments, the composition and methods described herein provide epitaxial growth of hydroxyapatite, which makes the new enamel crystals fully integrated into the existing tooth structure. In addition, the organized hydroxyapatite crystals can grow into the dentin tubule, which increases the bonding to dentin. Both the enamel integration and dentin tubule penetration can prevent secondary decay and failure of the restoration.

BRIEF DESCRIPTION OF THE DRAWINGS

FIG. 6A is a top view, FIG. 6B is a cross-section side view.

FIG. 8A is secondary electron image, and FIG. 8B is backscattering electron image showing the similar greyscale (mineral density) of synthetic enamel and natural enamel.

FIG. 9A shows the interface between the natural enamel and synthetic enamel growth at 5,000× magnification. FIG. 9B shows layer 3 and 4 of synthetic enamel at 10,000× magnification.

FIG. 10A shows the similar Z-number, i.e. relative mineral density, of synthetic enamel to natural enamel at 500× magnification. The number indicates the Z-number percentage of BSE greyscale relative to the natural enamel substrate. FIG. 10B is a higher magnification 2,000× showing the well-integrated interface between the synthetic enamel and natural enamel.

FIG. 11A shows the indents on different layers. FIG. 11B has the overlaid indent diagonal measurement values. It shows that synthetic enamel layer #1-4 have 91% of the hardness of natural healthy enamel. Top layer #5-6 has 61% of natural enamel hardness. This indicates that the mineralizing ions can penetrate deeper and increase mineral density and hardness with time. The etched enamel has shown fully recovered hardness.

FIG. 12A shows three layers (indicated by the arrows) of needle-like hydroxyapatite crystals. Other layers are plate octocalcium phosphate crystals. FIG. 12B. shows the higher magnification of FIG. 12A.

FIG. 10A is one example of qBSE results.

FIG. 21B shows a magnified image of the box in FIG. 21A, showing the needle-like synthetic enamel crystals inside a dentin tubule (indicated by dotted line).

FIGS. 25A (20,000× magnification) and 25C (50,000× magnification) using the composition with 0.5 ppm Sn (SnF2) and 2 ppm F (NaF). FIGS. 25B (20,000× magnification) and 25D (50,000× magnification), with 2 ppm F only.

FIG. 26A shows open dentin tubules on acid etched tooth before the treatment (2,000× magnification). FIG. 26B shows occluded dentin tubules by forming crystal plugs after 24 hours treatment (2,000× magnification).

FIG. 29A is a comparison of nanoidentation hardness on different synthetic enamel layers. The hardness unit of 1 GPa equals about 102 kg/mm$^2$. FIG. 29B is an optical image of synthetic enamel layer on dentin.

FIGS. 30A-30C demonstrate that synthetic enamel crystals formation on natural enamel in the presence of microbes at 5,000× magnification. FIG. 30A microbes from the air (rods, dots, and voids). FIG. 30B oral microbes. FIG. 30C *Escherichia coli* with a concentration of 10$^4$/mL.

FIG. 32A is a cross section side view of crystal growth and FIG. 32B is a top view of crystal growth.

FIG. 33A, 5,000× magnification. FIG. 33B, 20,000× magnification.

DETAILED DESCRIPTION

Figure 1:
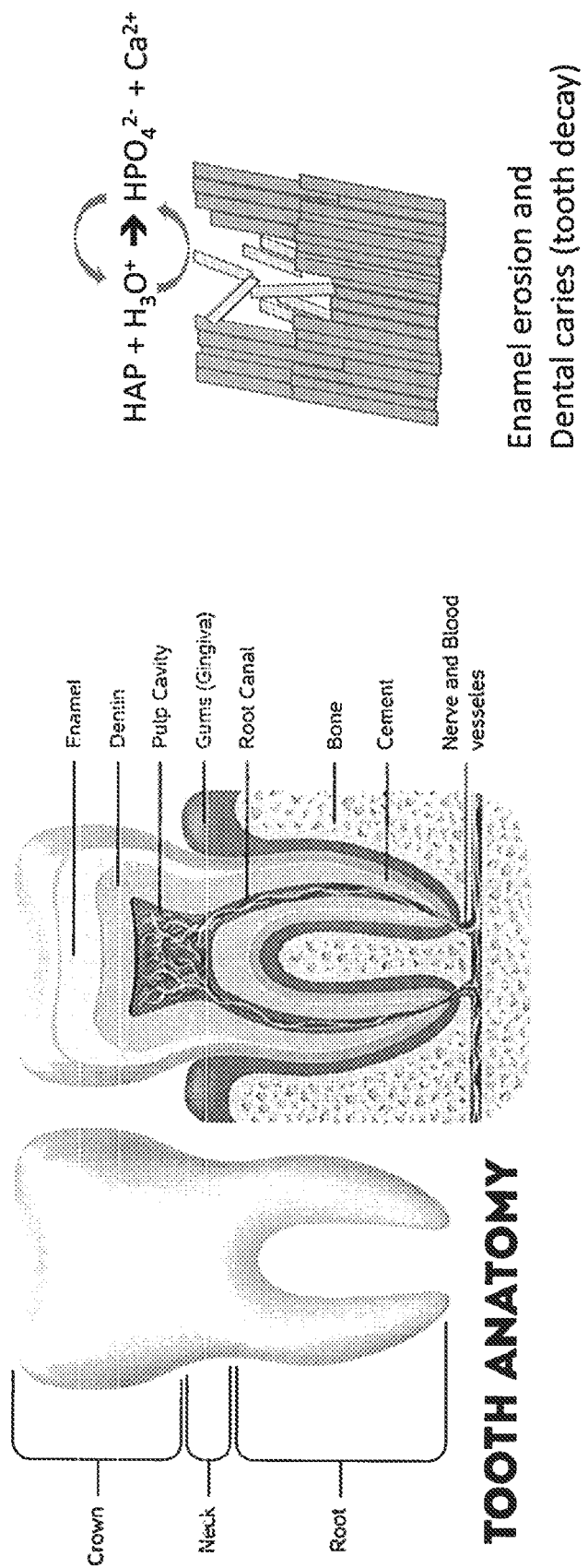
FIG. 1 depicts the different layers of a tooth and the process of the enamel erosion of a tooth.
Figure 2:
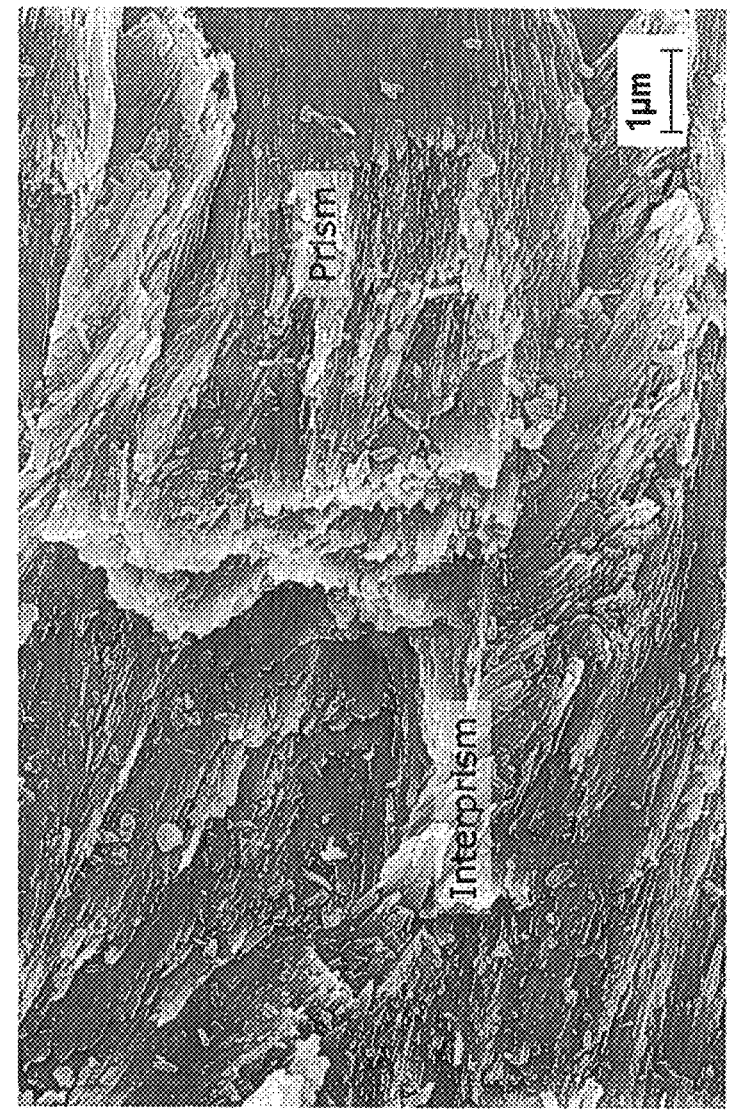
FIG. 2 describes the natural enamel microstructure including the composition of natural enamel and the fracture surface of a natural human enamel.
Figures 3A, 3B, 3C, 3D:
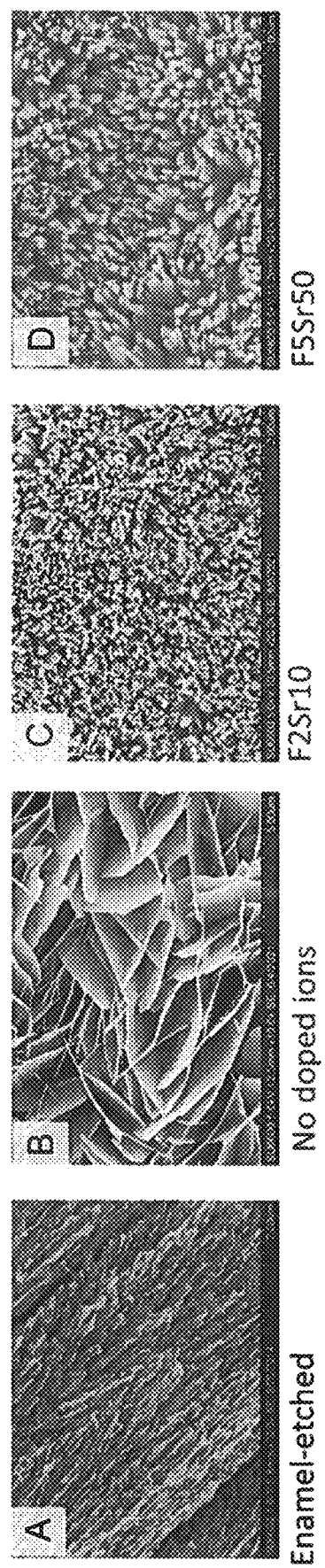
FIGS. 3A-3L shows crystal morphology and density of enamel remineralization can be controlled by varying the components of the remineralization composition (at 5,000× magnification). Etched natural enamel (FIG. 3A) and crystals formed in a biomineralization solution (BMS), without doped ions (FIG. 3B), in the presence of added 2 ppm fluoride and 10 ppm strontium (FIG. 3C), 2 ppm fluoride and 50 ppm strontium (FIG. 3D), 5 ppm strontium (FIG. 3E), 10 ppm strontium (FIG. 3F), 20 ppm strontium (FIG. 3G), 50 ppm strontium (FIG. 311), 1 ppm fluoride and 5 ppm strontium (FIG. 3I), 1 ppm fluoride and 10 ppm strontium (FIG. 3J), 1 ppm fluoride and 20 ppm strontium (FIG. 3K). 1 ppm fluoride and 50 ppm strontium (FIG. 3L).
Figure 3E:
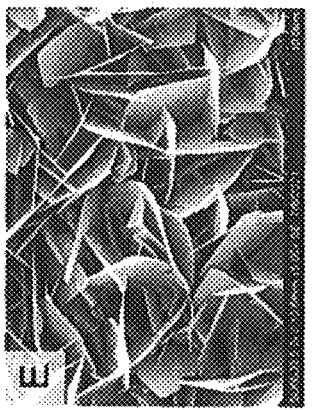
Figure 3F:
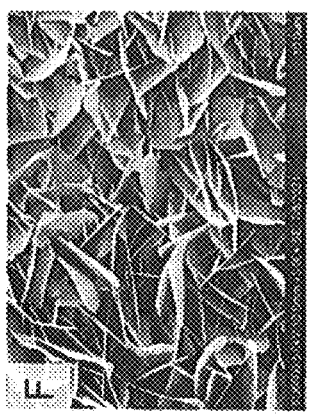
Figure 3G:
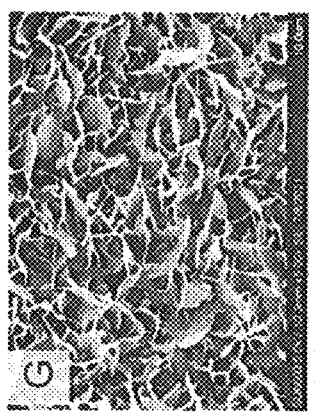
Figure 3H:
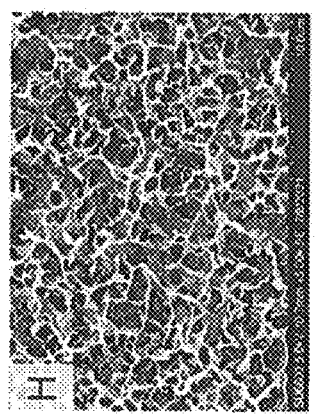
Figure 3I:
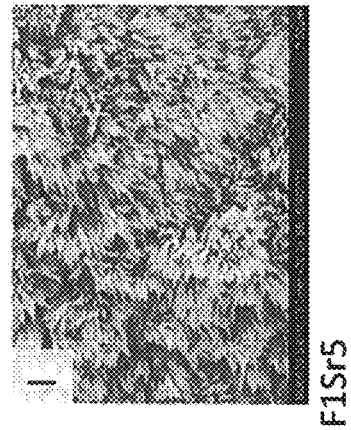
Figure 3J:
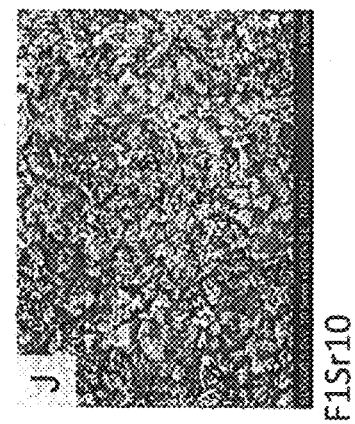
Figure 3K:
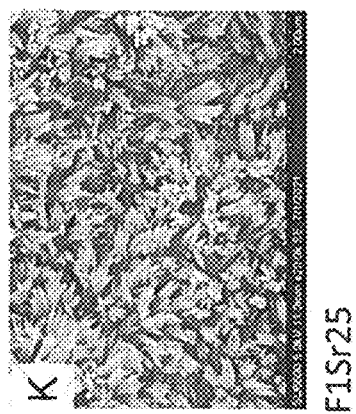
Figure 3L:
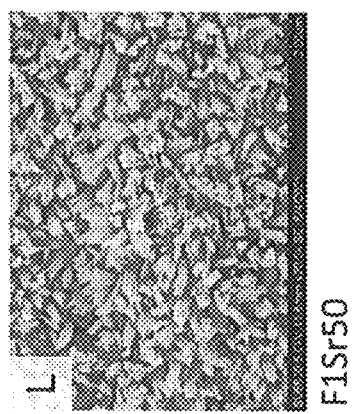
Figures 4A, 4B, 4C, 4D:
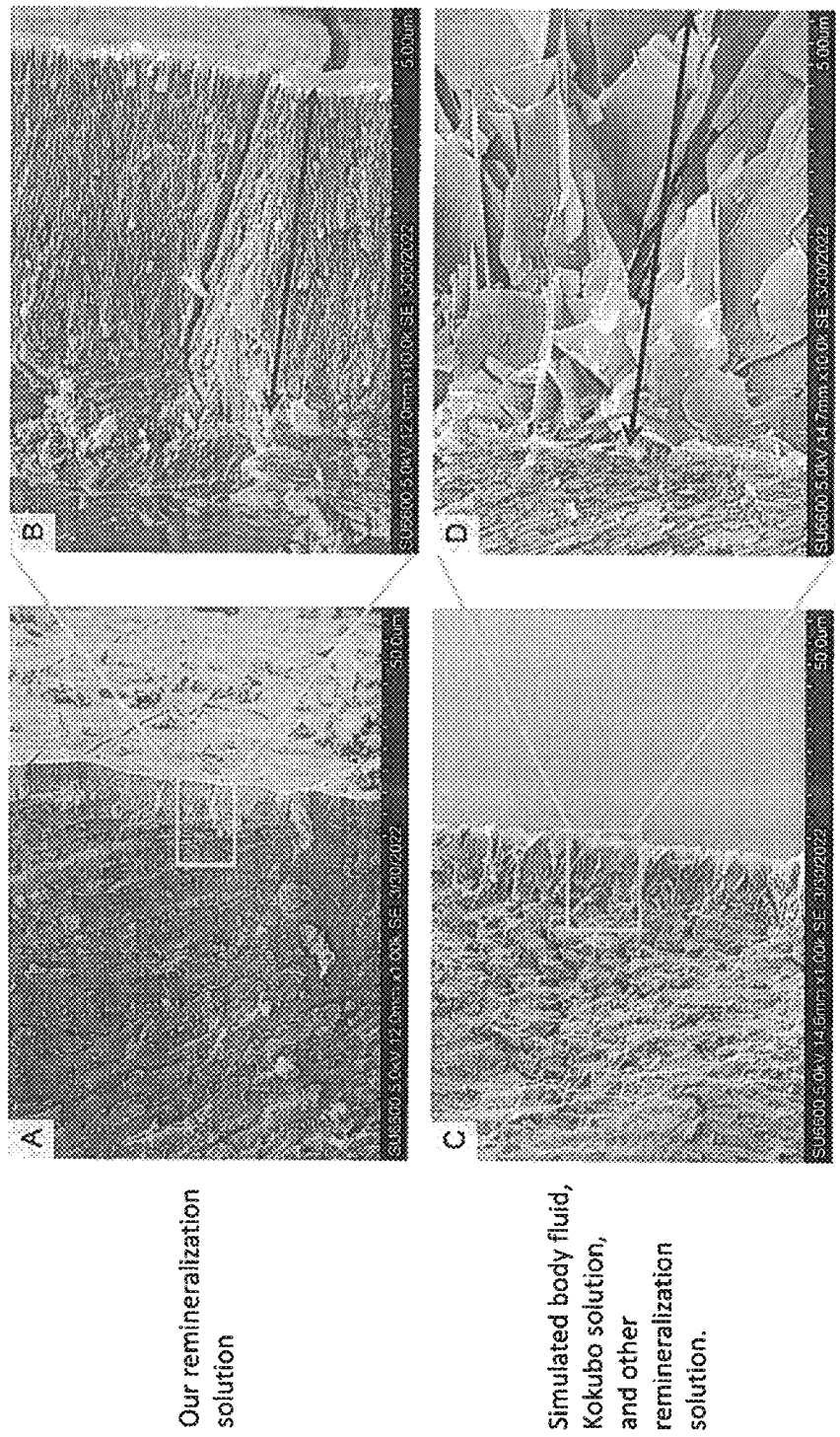
FIGS. 4A-4D show a cross-section view comparison of synthetic enamel layers prepared using a remineralization composition of the disclosure (FIGS. 4A and 4B) or from the art (FIGS. 4C and 4D). The cross-section was prepared by fracturing the specimen. Using the remineralization composition of the disclosure results in a densely packed layer of hydroxyapatite (FIGS. 4A and 4B). Using the prior art compositions result in a majority of loose structured octocalcium phosphate (FIGS. 4C and 4D).
Figure 5:
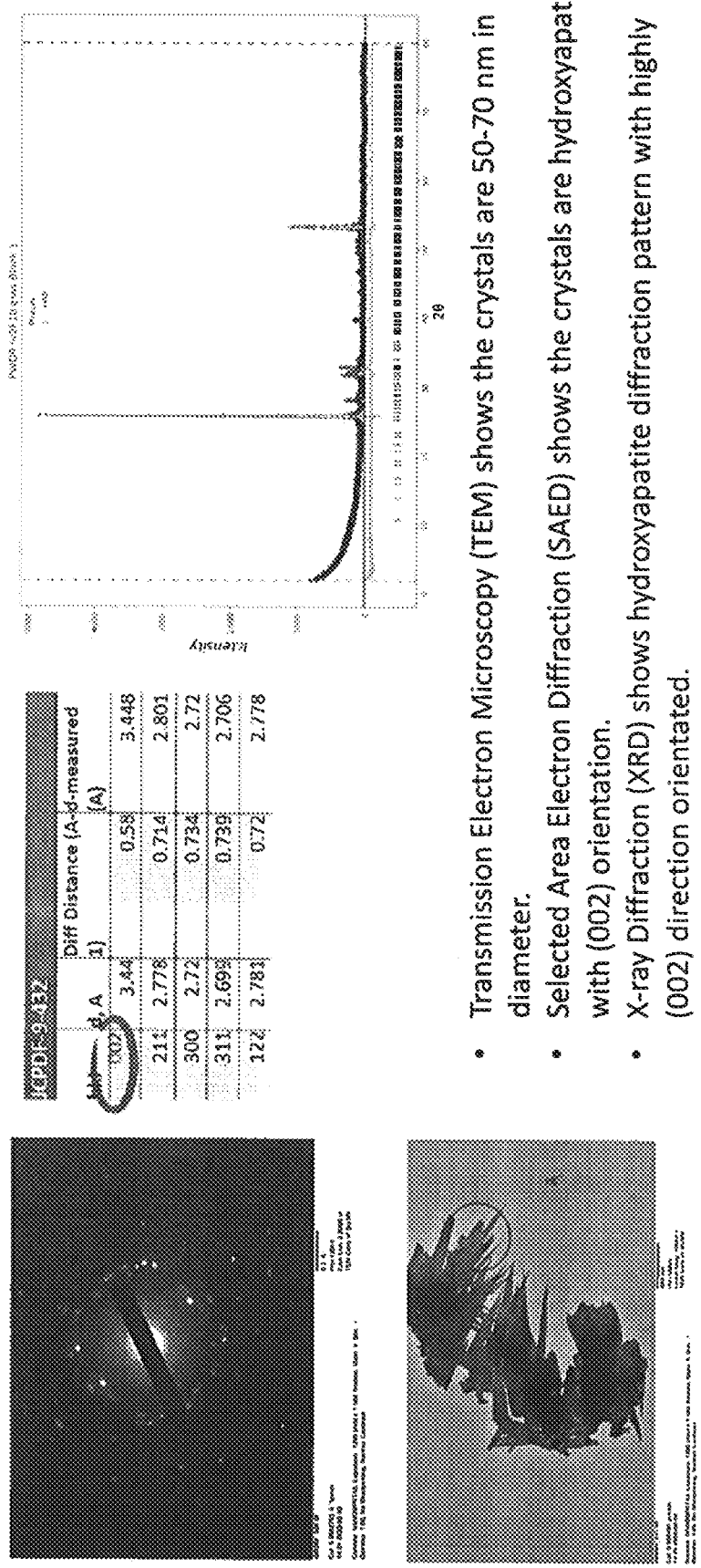
FIG. 5 shows that the crystal phase of synthetic enamel is the same as natural enamel.
Figure 6B:
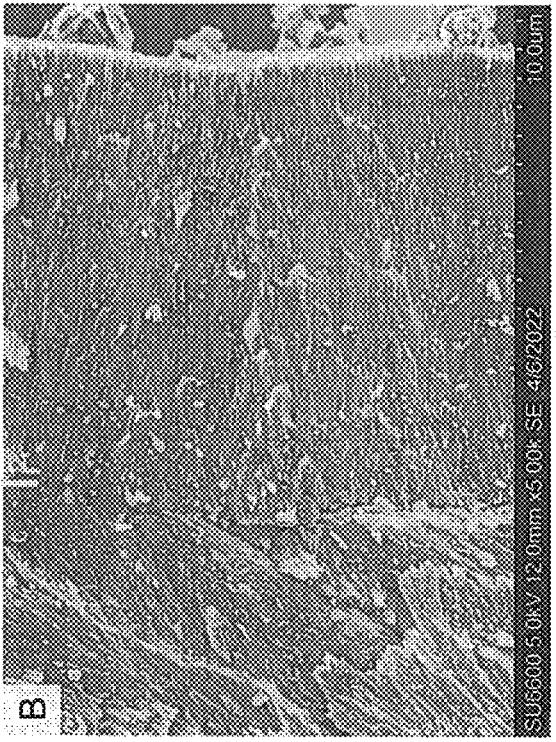
FIGS. 6A and 6B show the synthetic enamel layer grown on tooth surface for 2 days, with refreshed remineralization solution every 24 hours.
Figure 6A:
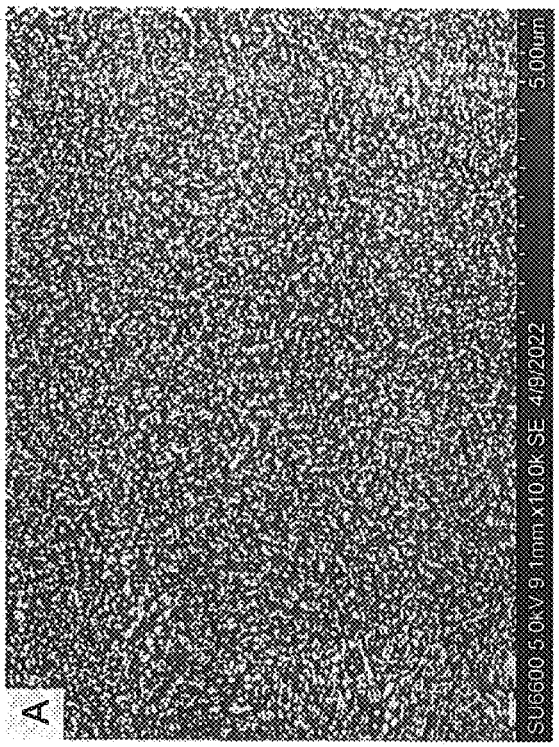
Figure 7B:
FIGS. 7A-7C show the synthetic enamel layers on a cross-section view. Tooth specimen was soaked in remineralization solution for 24 hours, rinsed with water for 10 mins, and put into fresh remineralization solution for another 24 hours, at low magnification 1,000× (FIG. 7A) and higher magnification 10,000× showing the interface between native enamel and synthetic enamel layer 1 (FIG. 7B) and between two synthetic enamel layers (FIG. 7C).
Figure 7C:
Figure 7A:
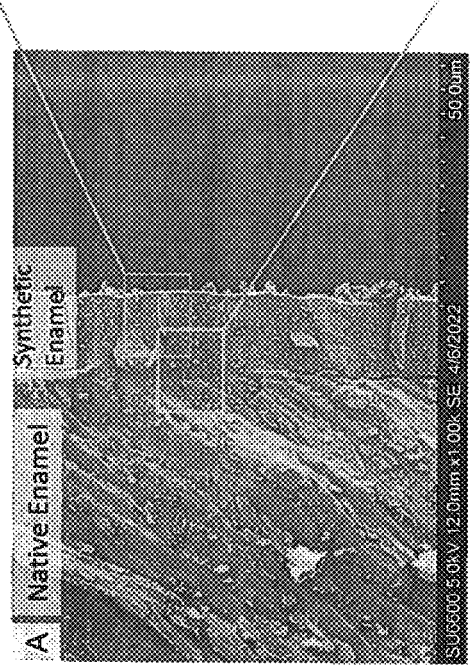
Figure 8B:
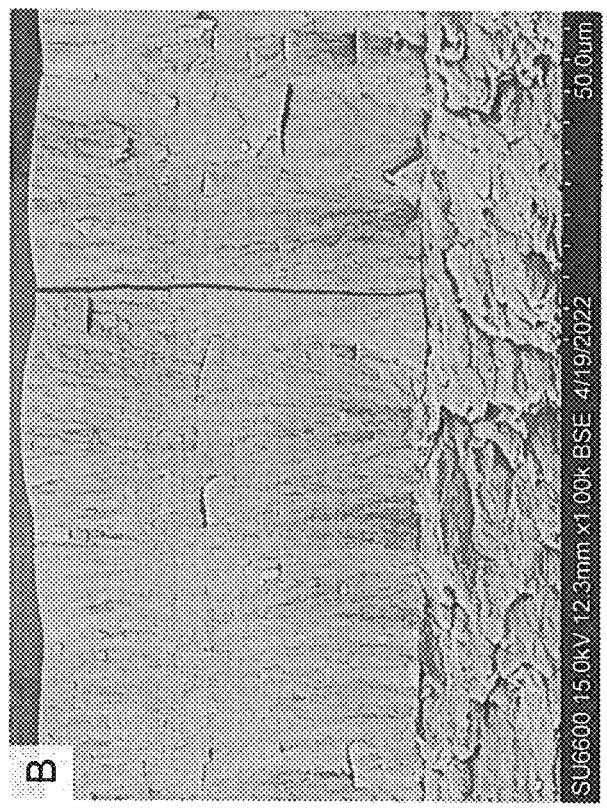
FIGS. 8A and 8B depict a cross-section of the synthetic enamel after continuous crystal growth for 6 days with refreshing remineralization solution every 24 hours. The cross-section was prepared by fracturing the tooth specimen.
Figure 8A:
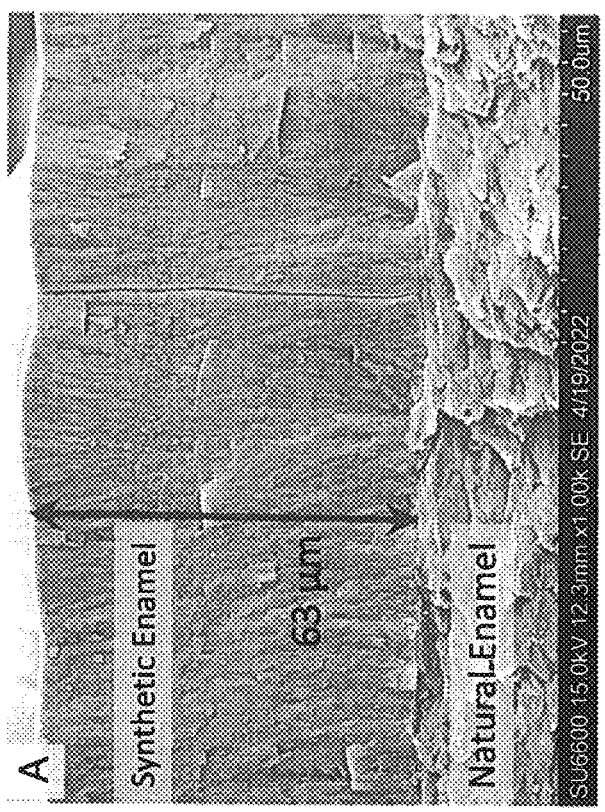
Figure 9B:
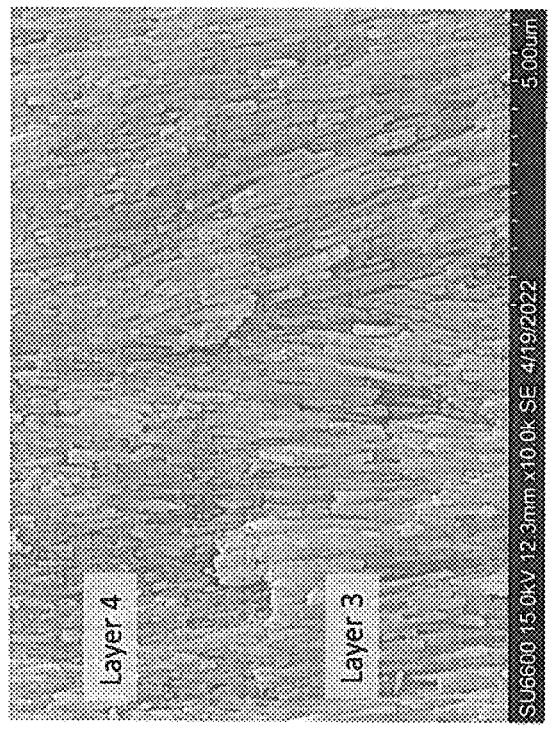
FIGS. 9A and 9B depict a higher magnification of FIG. 8A-8B.
Figure 9A:
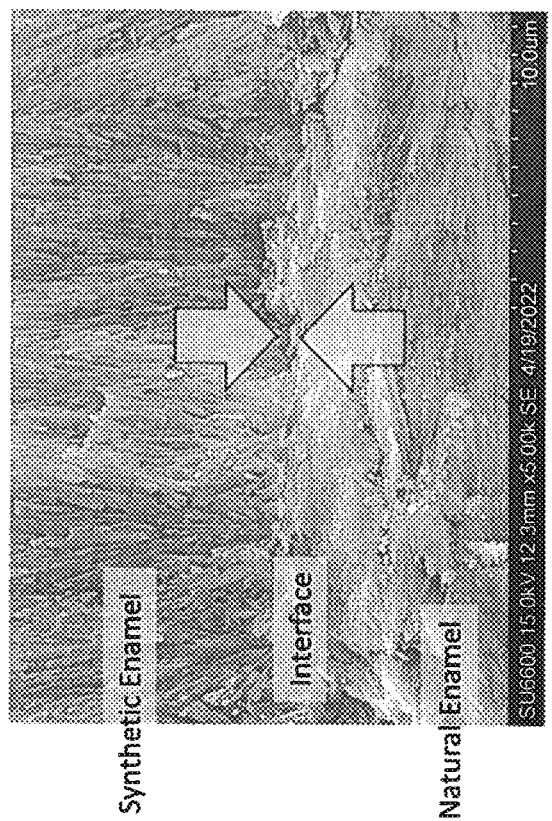
Figures 10A, 10B:
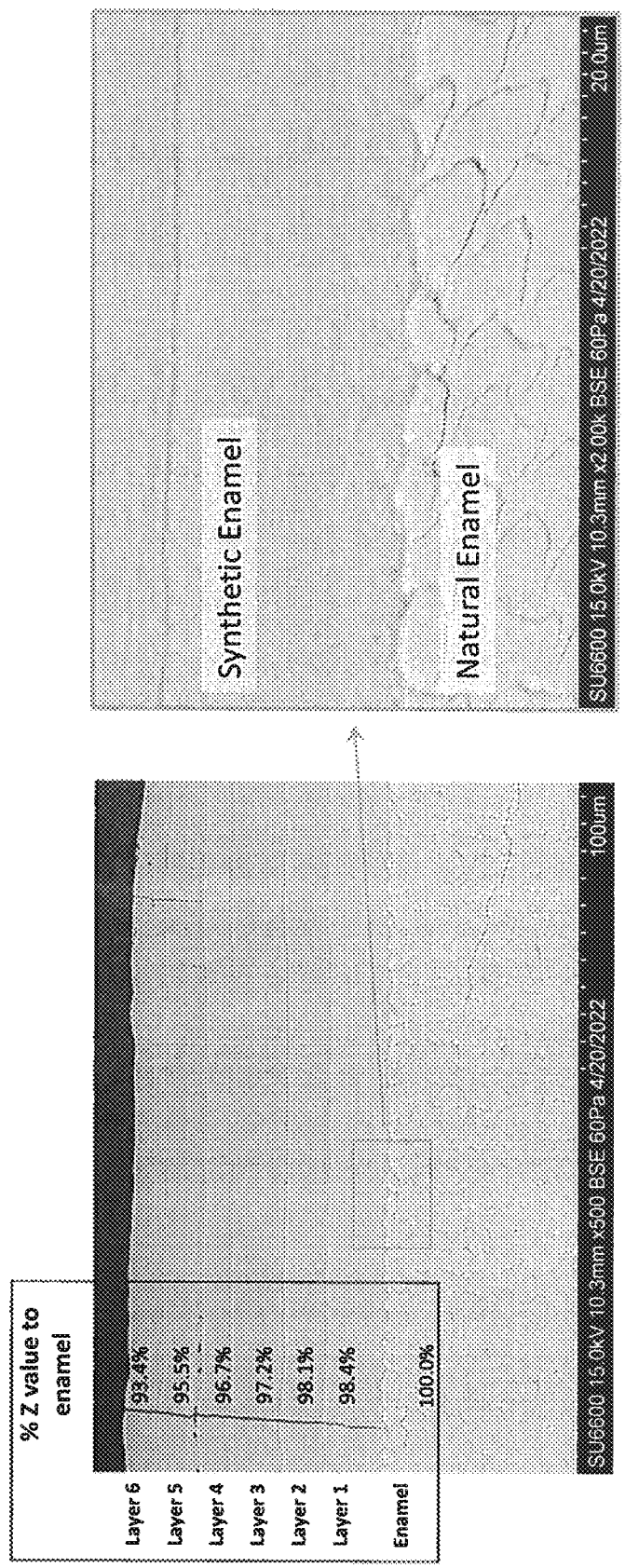
FIGS. 10A and 10B depict the backscattering electron images of the same specimen in FIG. 8 after fine polishing.
Figure 11B:
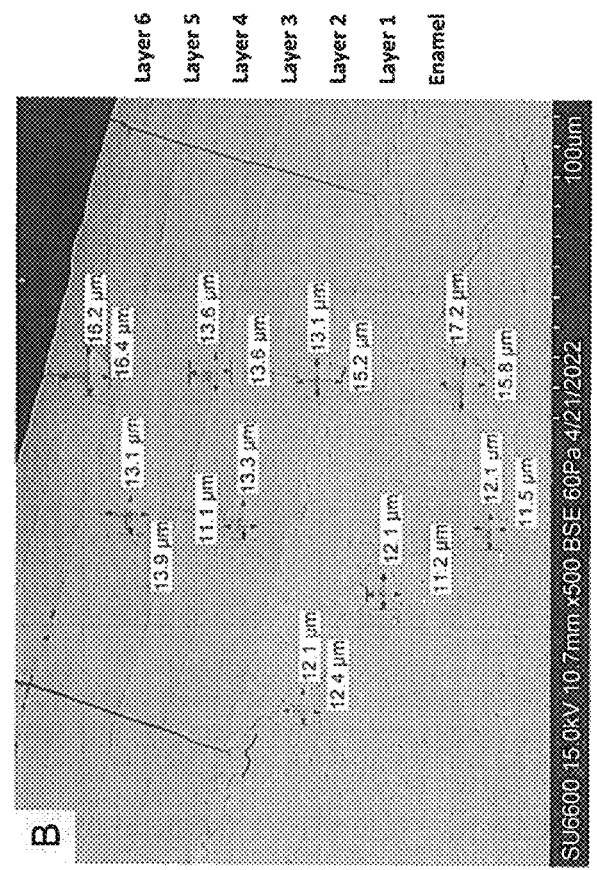
FIGS. 11A and 11B show the Vicker's microhardness test on polished cross section specimen in FIG. 10.
Figure 11A:
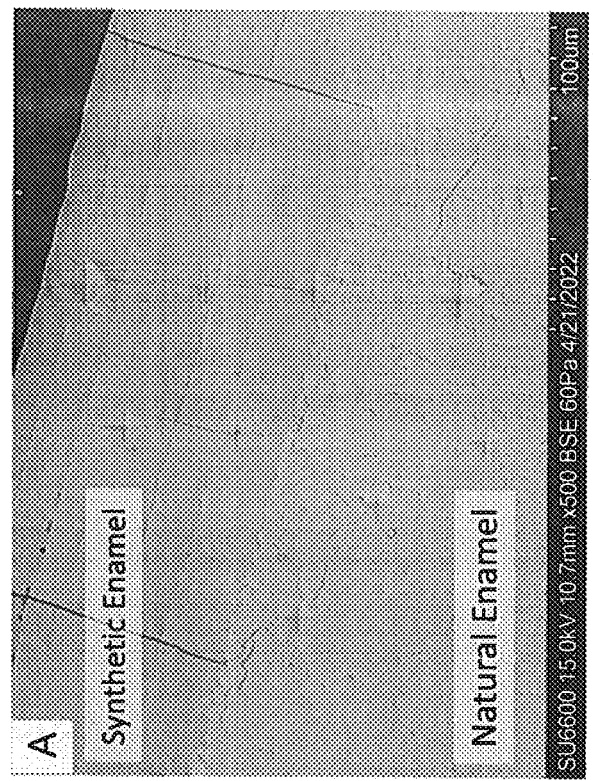
Figure 12B:
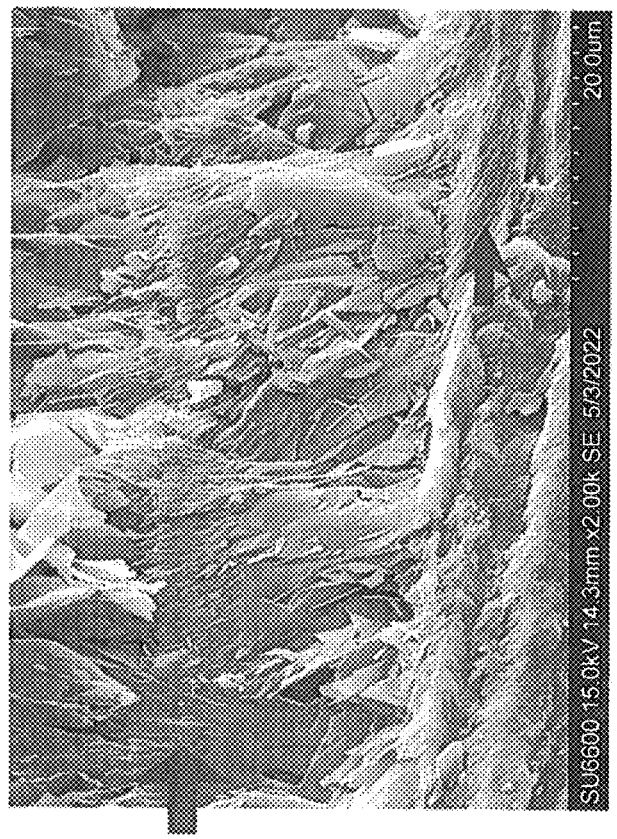
FIGS. 12A and 12B show controlled crystal growth forming hybrid multiple layers using different combinations of remineralization solution ingredients.
Figure 12A:
Figure 13:
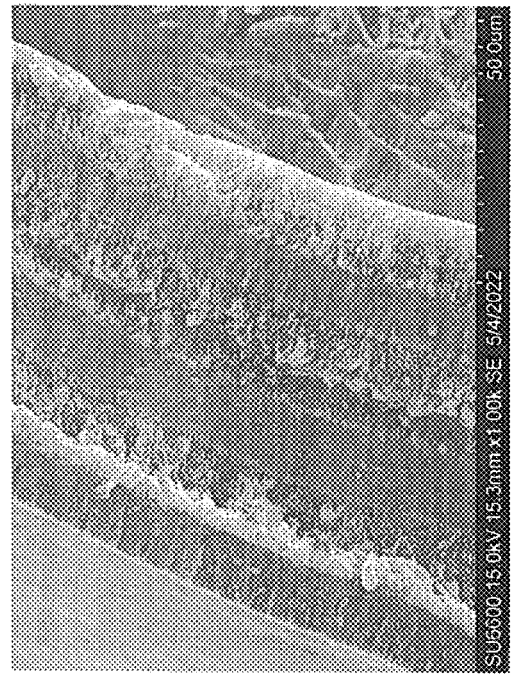
FIG. 13 depicts two other samples of controlled crystal growth forming hybrid multiple layers with different crystal structures using different combinations of remineralization solution ingredients.
Figure 13:
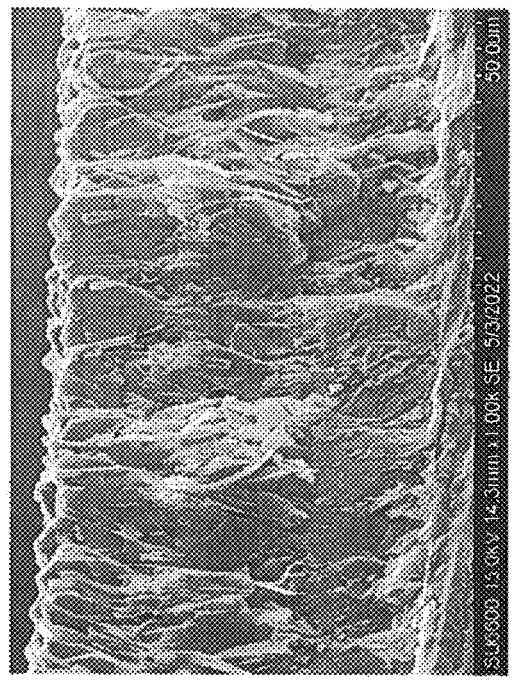
Figure 14:
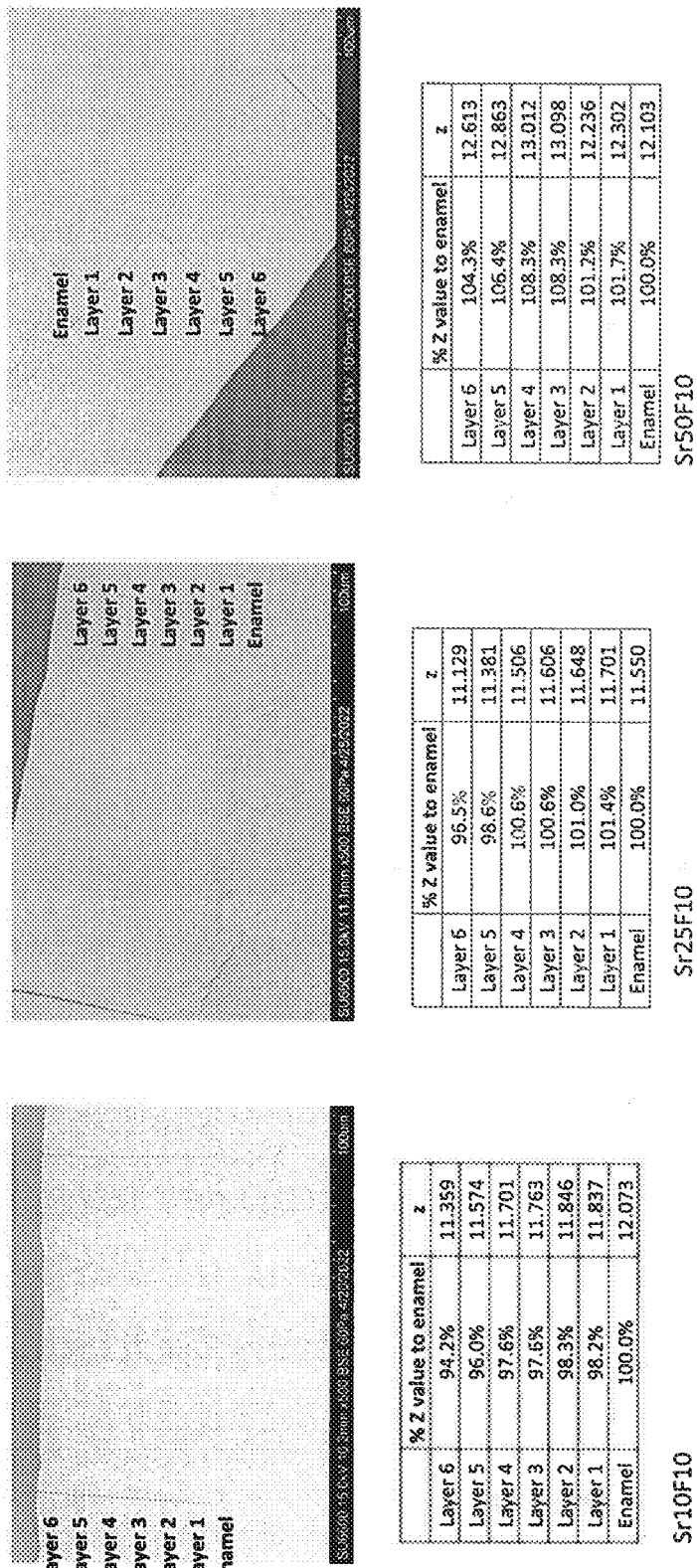
FIG. 14 depicts the quantitative back scattering analysis (qBSE) of the different synthetic enamel layers and the natural enamel. qBSE analysis provides information of the average atomic number of the specimen. It is directly associated with mineral density. Tested Z number was calibrated with carbon and aluminum.
Figure 15:
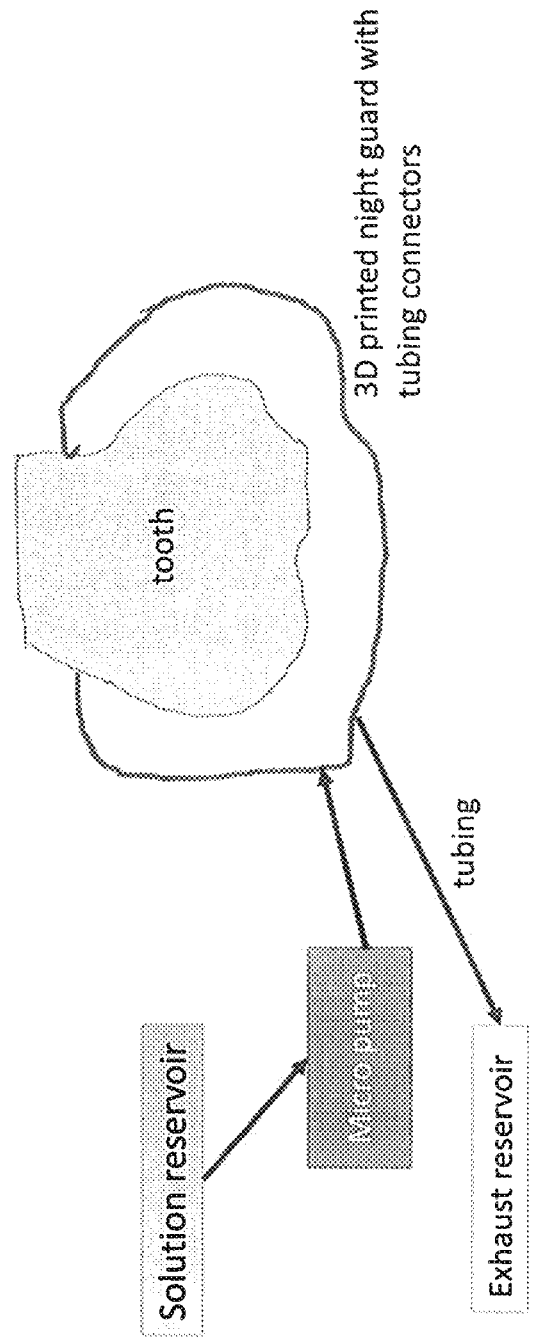
FIG. 15 is a schematic diagram of an exemplary apparatus for intra-oral synthetic enamel growth treatment via delivering remineralization solution.
Figures 16A, 16B:
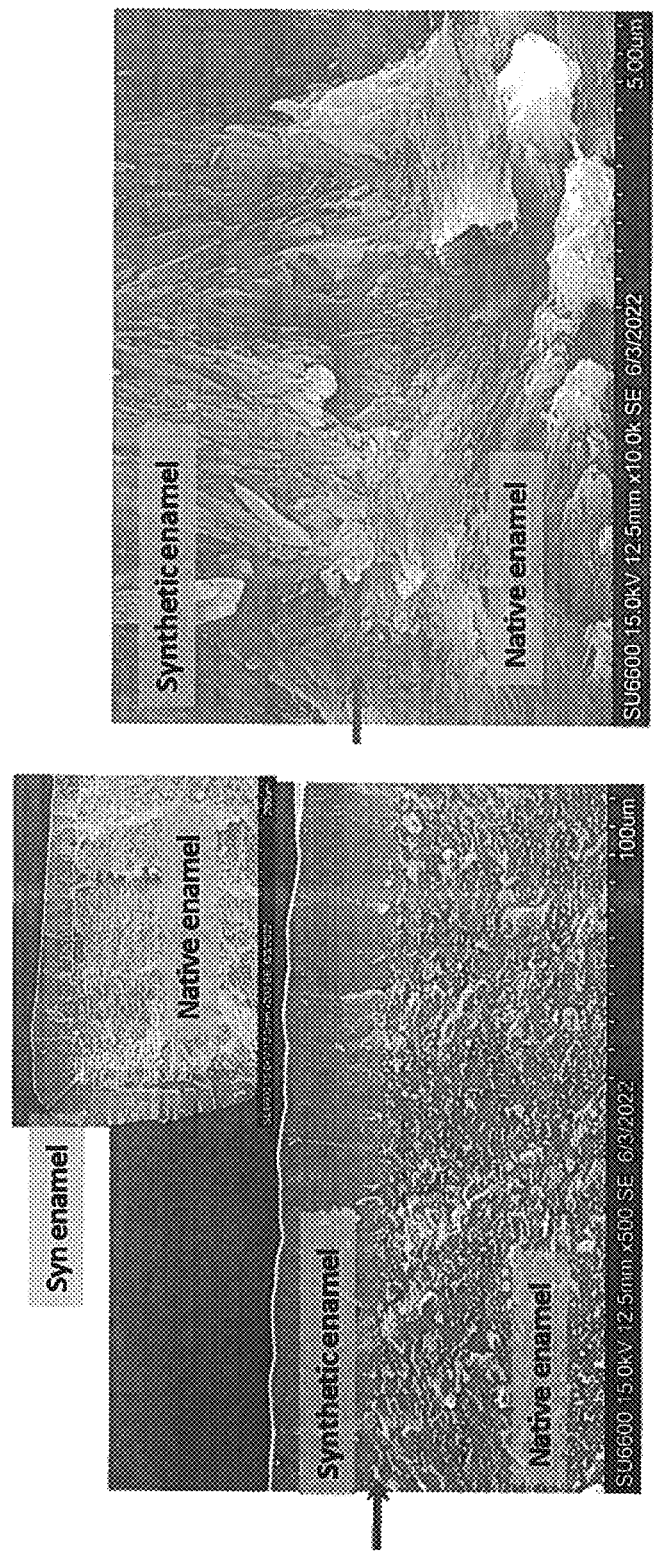
FIG. 16A and FIG. 16B show the interface (indicated by the arrow) of the natural enamel and the synthetic enamel. The newly formed synthetic enamel layer covers all the exposed enamel surface with a uniform thickness as seen at 500× magnification (FIG. 16A) and at 10,000× magnification (FIG. 16B).
Figure 17B:
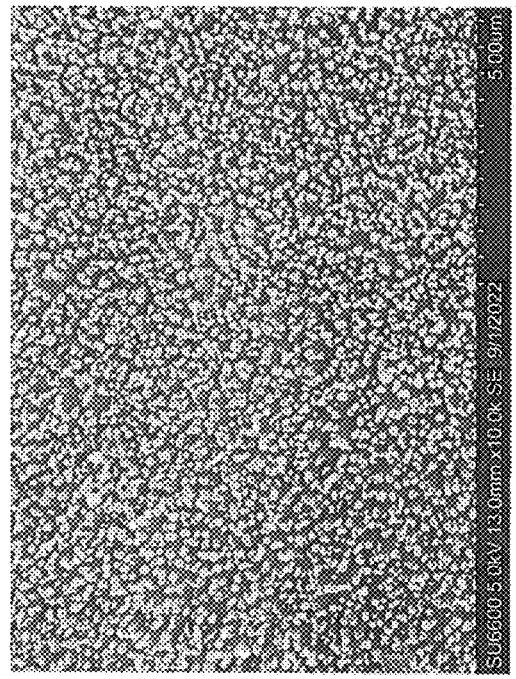
FIGS. 17A and 17B are top views at 200× magnification (FIG. 17A) and at 10,000× magnification (FIG. 17B) of the synthetic enamel on the etched natural dentin showing synthetic enamel comprises needle-like crystals that fully occlude the exposed dentin tubules after treatment in remineralization solution with refreshing three times every three days.
Figure 17A:
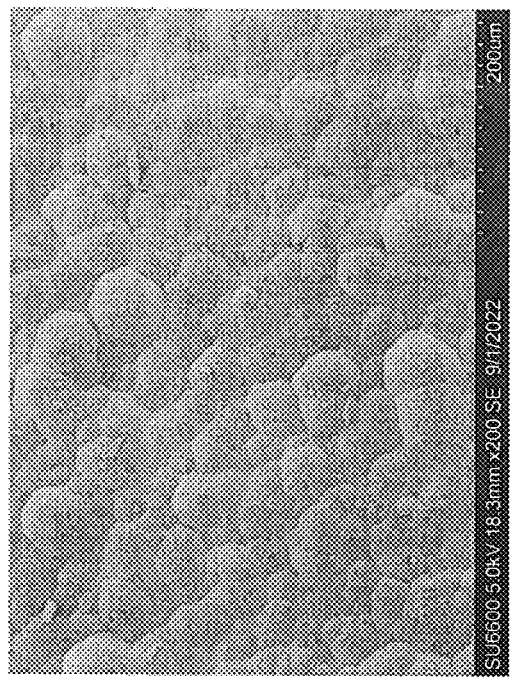
Figure 18C:
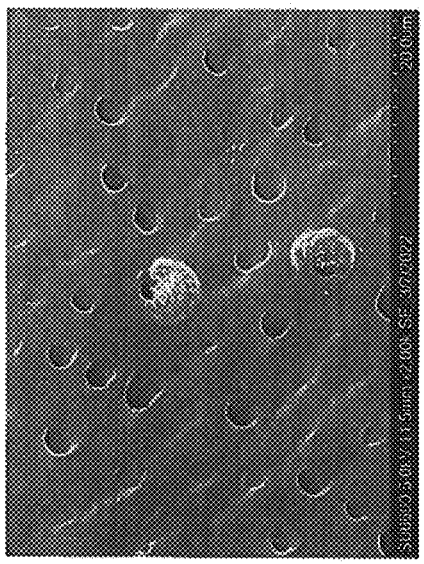
FIGS. 18A-18C show a new layer of synthetic enamel formed on dentin surface at 2,000× magnification.
Figure 18B:
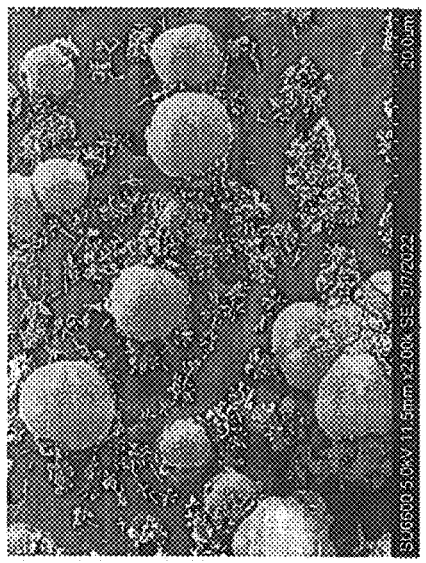
Figure 18A:
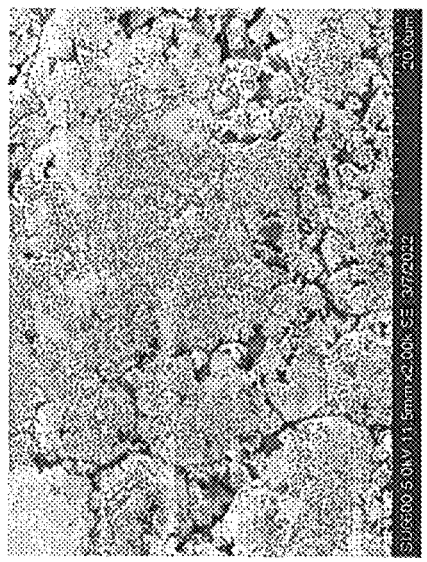
Figures 19A, 19B, 19C:
FIGS. 19A-19C show a new layer of synthetic enamel formed on dentin surface.
Figure 20B:
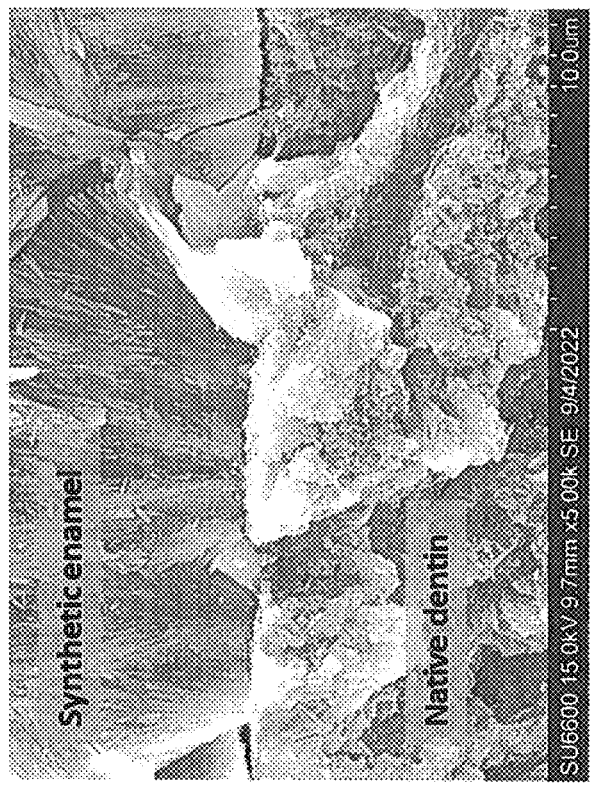
FIGS. 20A and 20B are a low magnification (FIG. 20A) and a higher magnification (FIG. 20B) image showing the synthetic enamel on the etched tooth dentin is uniform and about 50 micrometers in thickness. The synthetic enamel integrated with native dentin with a seamless interface at 5,000× magnification (FIG. 20B).
Figure 20A:
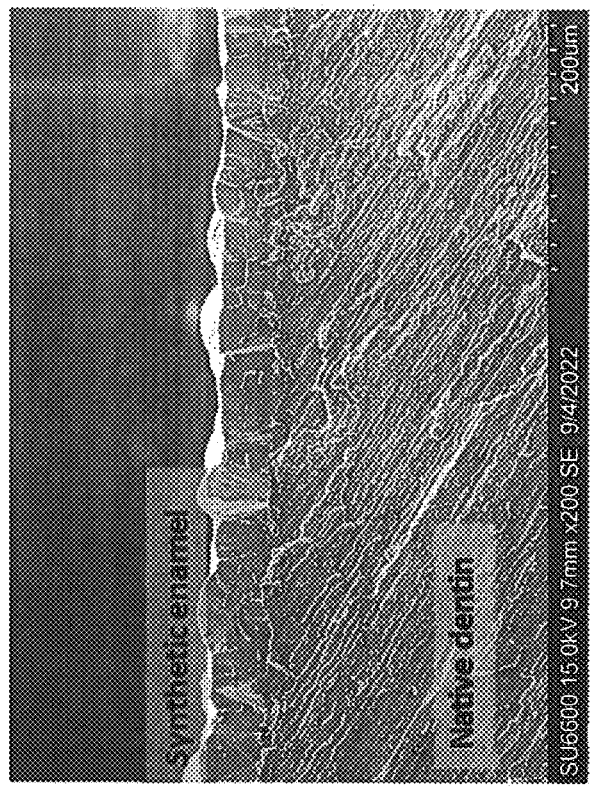
Figure 21B:
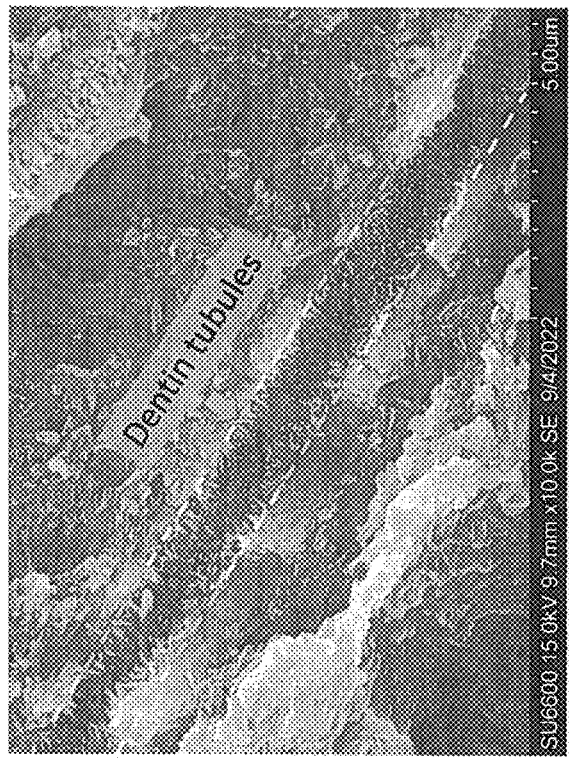
FIGS. 21A and 21B show the integration (indicated by arrow in FIG. 21A) of the natural dentin and the synthetic enamel.
Figure 21A:
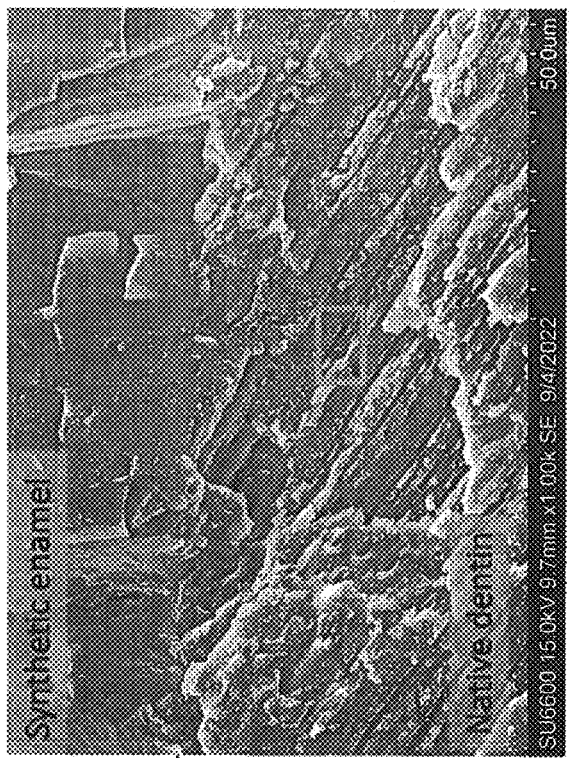
Figure 22:
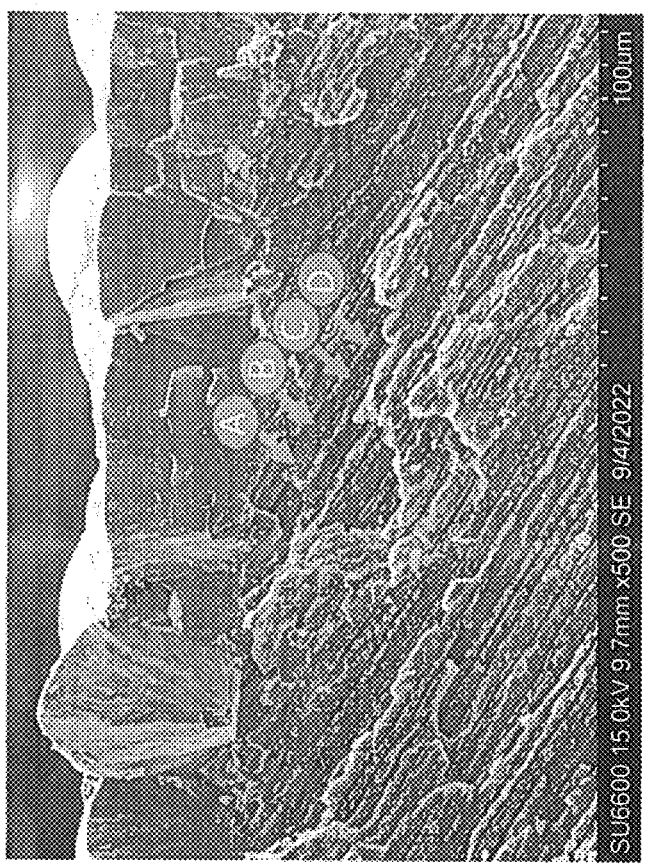
FIG. 22 depicts continuous growth of synthetic enamel in dentin tubules and on dentin surface (500×). Synthetic enamel crystals can be found at 50 m depth inside dentin tubules after being treated for nine days by remineralization solution doped with 10 ppm strontium and 10 ppm fluoride ions and the solution was refreshed every three days.
Figure 23A:
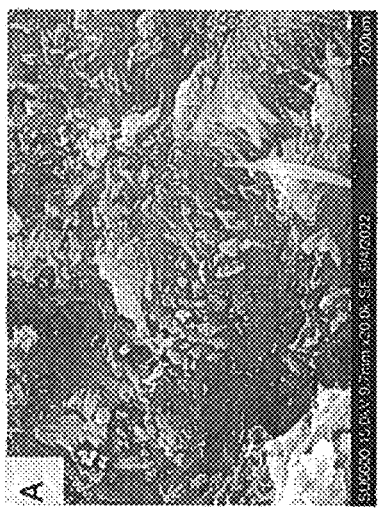
FIGS. 23A-23D show a higher magnification (20,000×) of 4 different depths of synthetic enamel formed in dentin tubules shown in FIG. 22.
Figure 23B:
Figure 23C:
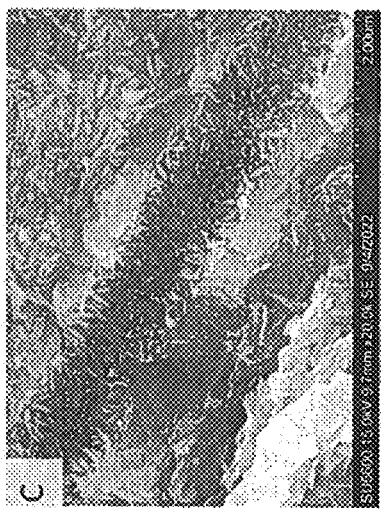
Figure 23D:
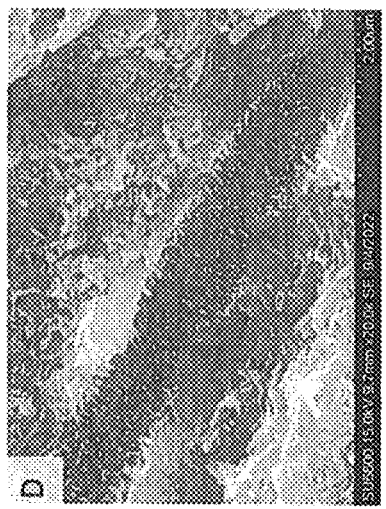
Figure 24A:
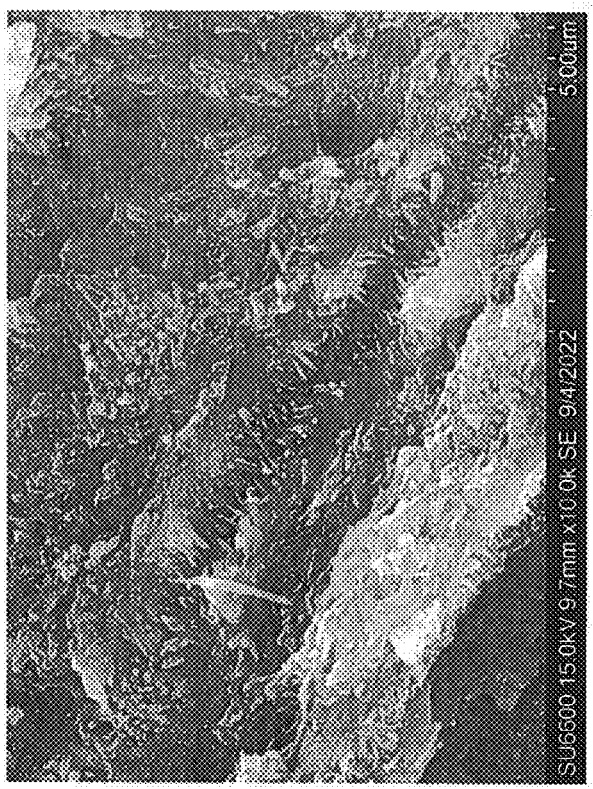
FIGS. 24A and 24B show occlusion of a dentin tubule after treatment (FIG. 24A, a higher magnification of FIG. 22 near arrows of A and B) versus an open dentin tubule in the native dentin (FIG. 24B).
Figure 24B:
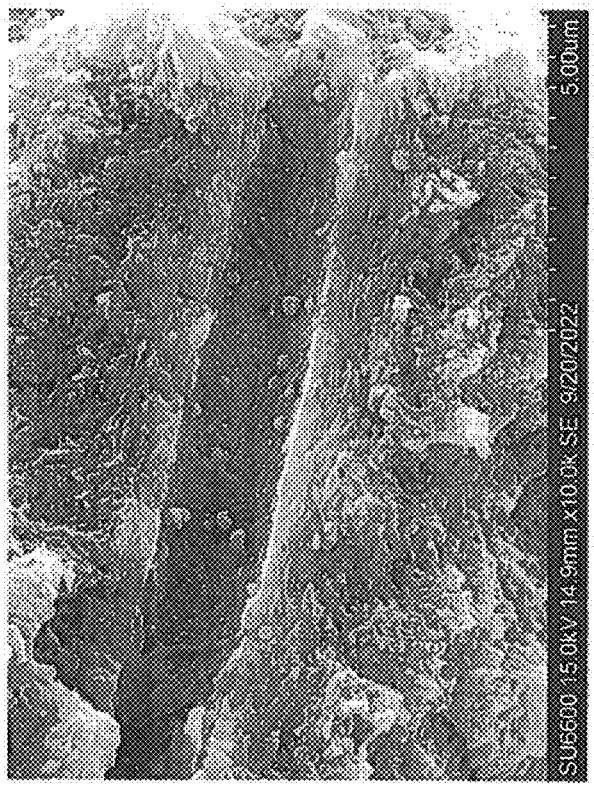
Figure 25B:
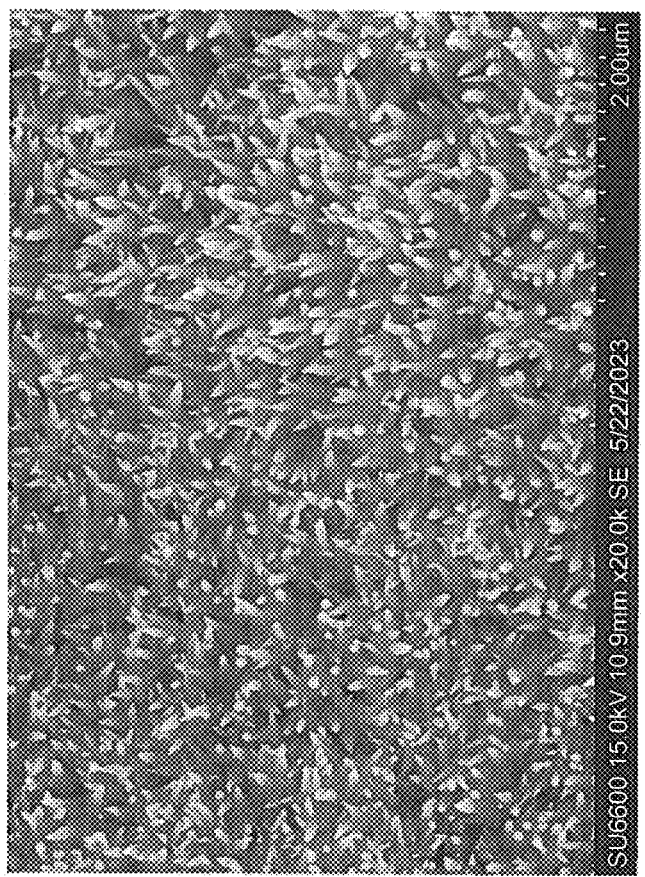
FIGS. 25A-25D depict the synergistic effect of Tin (II) and fluoride ions on synthetic enamel formation. The crystal density is much higher in the presence of Tin (II) ion.
Figure 25A:
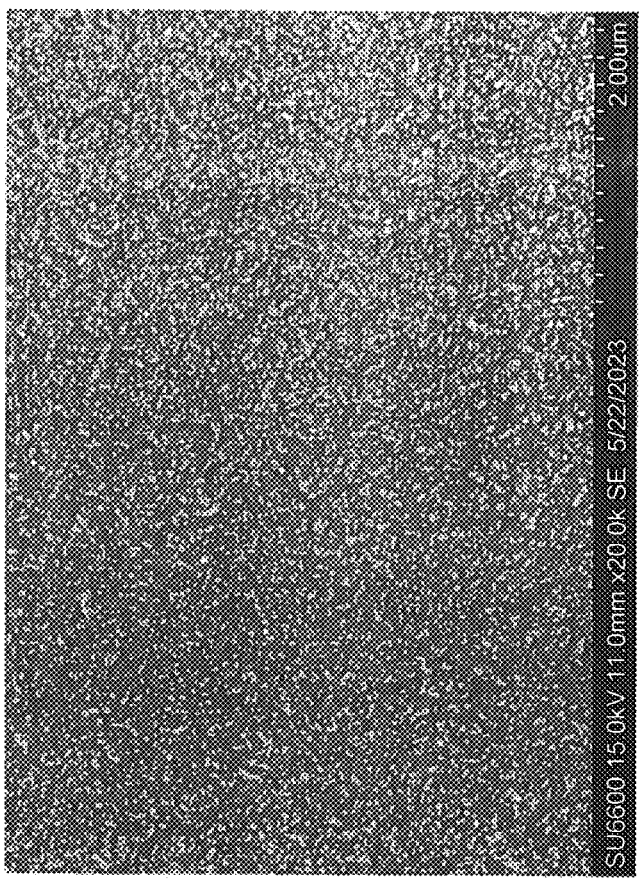
Figures 25C, 25D:
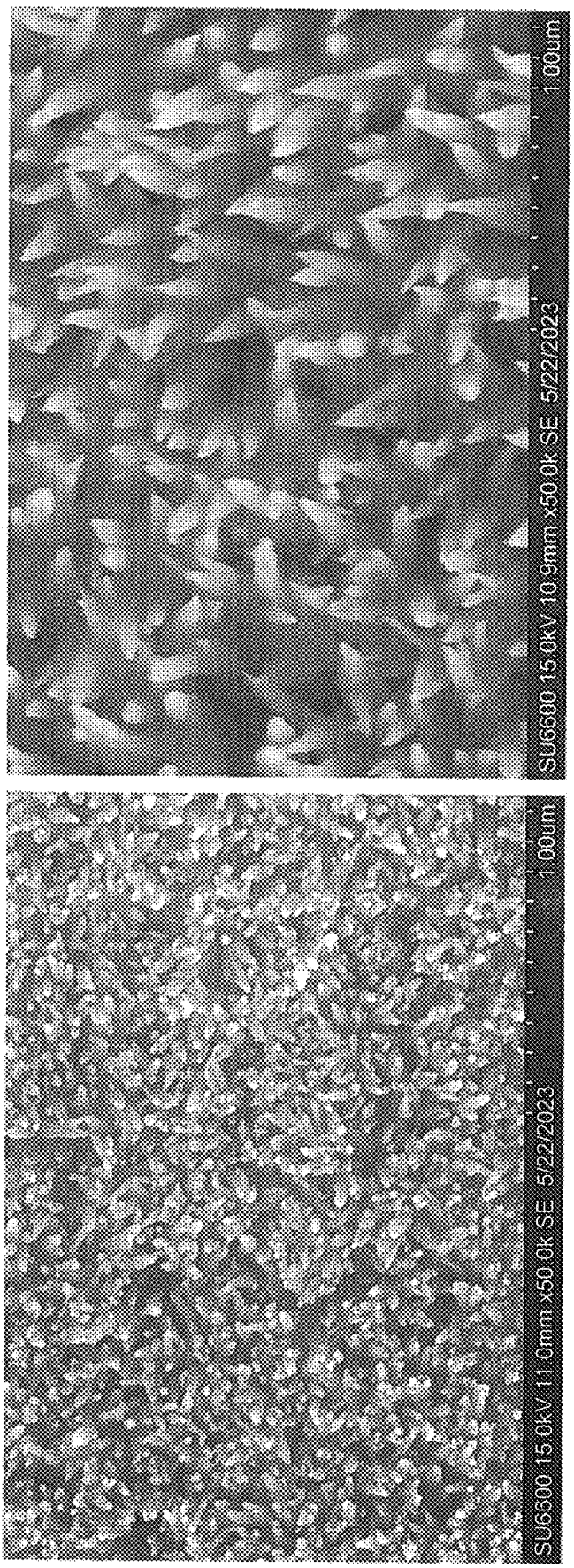

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Generally, remineralization compositions comprise calcium ions, phosphate ions, and fluoride ions. Inventors have discovered inter alia that doping remineralization compositions with strontium ions or stannous ions provides a synergistic effect and have a synergistic remineralization activity. Accordingly, in one aspect provided herein is a remineralization composition comprising calcium ions, phosphate ions, and fluoride ions. In some embodiments of any one of the aspects, the remineralization composition is doped with strontium ions or stannous ions. In other words, the remineralization composition comprises strontium ions or stannous ions.

Generally, the calcium ions in the remineralization composition are form of a calcium salt. Exemplary calcium salts amenable to the various aspects described herein include, but are not limited to, calcium chloride, calcium acetate, calcium bromide, calcium fluoride, calcium iodide, calcium gluconate, calcium sulfate, calcium phosphate, calcium glycerophosphate, calcium hydrogen phosphate, hydroxyapatite, calcium phosphonate, calcium borate, calcium carbonate, calcium oxalate, calcium citrate, calcium formate, calcium fumarate, calcium lactate, calcium sulfate, calcium tartrate, calcium hydride, calcium nitrite, calcium molybdate, calcium butyrate, calcium isobutyrate, calcium malate, calcium maleate, calcium benzoate, calcium lactate, calcium propionate, calcium carbonate, and the like. In some preferred embodiments of the various aspects described herein, the calcium salt is calcium chloride. In other words, remineralization composition comprises calcium chloride.

In some embodiments of the various aspects described herein, the remineralization composition can comprise calcium ions at a concentration up to 500 mM. For example, the calcium ions can be present at a concentration from about 0.1 mM to about 500 mM. In some embodiments of any one of the aspects described herein, the remineralization composition comprises calcium ions at a concentration from about 0.2 mM to about 200 mM, from about 0.5 mM to about 150 mM, from about 0.75 mM to about 100 mM or from about 1 mM to about 50 mM. In some embodiments of any one of the aspects described herein, the remineralization composition comprises calcium ions at a concentration from about 0.2 mM to about 50 mM, about 0.25 mM to about 40 mM, from about 0.5 mM to about 25 mM, from about 0.75 mM to about 20 mM, from about 1 mM to about 15 mM or 1.5 mM to about 10 mM. For example, the remineralization composition comprises calcium ions at a concentration from about 2 mM to about 5 mM.

In some embodiments of any one of the aspects described herein, the remineralization composition comprises calcium ions at a concentration of about 0.5 mM, about 1 mM, about 1.25 mM, about 1.5 mM, about 1.75 mM, about 2 mM, about 2.25 mM, about 2.5 mM, about 2.75 mM, about 3 mM, about 3.25 mM, about 3.5 mM, about 3.75 mM, about 4 mM, about 4.25 mM, about 4.5 mM, about 4.75 mM, about 5 mM, about 5.25 mM, about 5.5 mM, about 5.75 mM, about 6 mM, about 6.25 mM, about 6.5 mM, about 6.75 mM, about 7 mM, about 7.25 mM, about 7.5 mM, about 7.75 mM, about 8 mM, about 8.25 mM, about 8.5 mM, about 8.75 mM, about 9 mM, about 9.25 mM, about 9.5 mM, about 9.75 mM, or about 10 mM. In some preferred embodiments, the remineralization composition comprises calcium ions at a concentration of between 2 mM to 5 mM, between 2.5 mM to 5 mM, between 3 mM to 5 mM, between 3.5 mM to 5 mM, between 4 mM to 5 mM, between 2 mM and 4.5 mM, between 2 mM and 4 mM, between 2 mM and 3.5 mM, between 2 mM and 3 mM.

In some embodiments of the various aspects described herein, the phosphate ions in the remineralization composition can be in form of a phosphate salt. Exemplary phosphate salts amenable to the various aspects described herein include, but are not limited to, potassium phosphate, sodium phosphate, calcium phosphate, ammonium phosphate, magnesium phosphate, zinc phosphate, copper phosphate, and the like. In some preferred embodiments of the various aspects described herein, the phosphate salt is potassium phosphate. In other words, remineralization composition comprises potassium phosphate.

The phosphate ions can be present in the remineralization composition at a concentration up to about 100 mM. For example, the phosphate ions can be present at concentration from about 0.1 mM to about 90 mM. In some embodiments of any one of the aspects described herein, the remineralization composition comprises phosphate ions at a concentration from about 0.2 mM to about 200 mM, from about 0.5 mM to about 150 mM, from about 1 mM to about 100 mM, from about 1.5 mM to about 50 mM, from about 2 mM to about 25 mM or from about 2.5 mM to about 20 mM. For example, the remineralization composition comprises phosphate ions at a concentration from about 3 mM to about 9 mM.

In some embodiments of any one of the aspects described herein, the remineralization composition comprises phosphate ions at a concentration of about 0.25 mM, about 0.5 mM, about 0.75 mM, about 1 mM, about 1.25 mM, about 1.5 mM, about 1.75 mM, about 2 mM, about 2.25 mM, about 2.5 mM, about 2.75 mM, about 3 mM, about 3.25 mM, about 3.5 mM, about 3.75 mM, about 4 mM, about 4.25 mM, about 4.5 mM, about 4.75 mM, about 5 mM, about 5.25 mM, about 5.5 mM, about 5.75 mM, about 6 mM, about 6.25 mM, about 6.5 mM, about 6.75 mM, about 7 mM, about 7.25 mM, about 7.5 mM, about 7.75 mM, about 8 mM, about 8.25 mM, about 8.5 mM, about 8.75 mM, about 9 mM, about 9.25 mM, about 9.5 mM, about 9.75 mM, about 10 mM, about 10 mM, about 10.25 mM, about 10.5 mM, about 10.75 mM, 11 mM, about 11.25 mM, about 11.5 mM, about 11.75 mM, about 12 mM, about 12.25 mM, about 12.5 mM, about 12.75 mM, about 13 mM, about 13.25 mM, about 13.5 mM, about 13.75 mM, about 14 mM, about 14.25 mM, about 14.5 mM, about 14.75 mM, about 15 mM, about 15.25 mM, about 15.5 mM, about 15.75 mM, about 16 mM, about 16.25 mM, about 16.5 mM, about 16.75 mM, about 17 mM, about 17.25 mM, about 17.5 mM, about 17.75 mM, about 18 mM, about 18.25 mM, about 18.5 mM, about 18.75 mM, about 19 mM, about 19.25 mM, about 19.5 mM, about 19.75 mM, or about 20 mM. In some preferred embodiments, the remineralization composition comprises phosphate ions at a concentration of between 1 mM and 1.75 mM, between 1 mM and 1.7 mM, between 1 mM and 1.65 mM, between 1 mM and 1.6 mM, between 1 mM and 1.55 mM, between 1 mM and 1.5 mM, between 1 mM and 1.45 mM, between 1 mM and 1.4 mM, between 1 mM and 1.35 mM, between 1 mM and 1.3 mM, between 1 mM and 1.25 mM, between 1 mM and 1.2 mM, between 1 mM and 1.15 mM, between 1 mM and 1.1 mM, between 1 mM and 1.05 mM.

In embodiments of the various aspects described herein, the fluoride ions in the remineralization composition can be in form of a fluoride salt. Exemplary fluoride salts amenable to the various aspects described herein include, but are not limited to, sodium fluoride, potassium fluoride, cesium fluoride, silver fluoride, ammonium fluoride, sodium monofluorophosphate, sodium fluorosilicate, ammonium fluorosilicate, amine fluoride, ammonium fluoride, silver diamine fluoride, zinc fluoride, magnesium fluoride, titanium tetrafluoride, zirconium fluoride, and the like. In some preferred embodiments of the various aspects described herein, the fluoride salt is sodium fluoride. In other words, remineralization composition comprises sodium fluoride.

The fluoride ions can be doped into the remineralization composition at a concentration up to about 500 ppm. For example, the fluoride ions can be present at concentration from about 0.2 ppm to about 300 ppm. In some embodiments of any one of the aspects described herein, the remineralization composition comprises fluoride ions at a concentration from about 0.5 ppm to about 150 ppm, from about 1 ppm to about 125 ppm, from about 1.5 ppm to about 100 ppm, from about 2 ppm to about 75 ppm, or from about 2.5 ppm to about 50 ppm. For example, the fluoride ions can be present in the remineralization composition in a concentration from about 2 ppm to about 30 ppm.

In some embodiments, the remineralization composition comprises fluoride ions at a concentration about 0.25 ppm, about 0.5 ppm, about 0.75 ppm, about 1 ppm, about 1.25 ppm, about 1.5 ppm, about 1.75 ppm, about 2 ppm, about 2.25 ppm, about 2.5 ppm, about 2.75 ppm, about 3 ppm, about 3.25 ppm, about 3.5 ppm, about 3.75 ppm, about 4 ppm, about 4.25 ppm, about 4.5 ppm, about 4.75 ppm, about 5 ppm, about 5.25 ppm, about 5.5 ppm, about 5.75 ppm, about 6 ppm, about 6.25 ppm, about 6.5 ppm, about 6.75 ppm, about 7 ppm, about 7.25 ppm, about 7.5 ppm, about 7.75 ppm, about 8 ppm, about 8.25 ppm, about 8.5 ppm, about 8.75 ppm, about 9 ppm, about 9.25 ppm, about 9.5 ppm, about 9.75 ppm, about 10 ppm, about 10.25 ppm, about 10.5 ppm, about 10.75 ppm, about 11 ppm, about 11.25 ppm, about 11.5 ppm, about 11.75 ppm, about 12 ppm, about 12.25 ppm, about 12.5 ppm, about 12.75 ppm, about 13 ppm, about 13.25 ppm, about 13.5 ppm, about 13.75 ppm, about 14 ppm, about 14.25 ppm, about 14.5 ppm, about 14.75 ppm, about 15 ppm, about 15.25 ppm, about 15.5 ppm, about 15.75 ppm, about 16 ppm, about 16.25 ppm, about 16.5 ppm, about 16.75 ppm, about 17 ppm, about 17.25 ppm, about 17.5 ppm, about 17.75 ppm, about 18 ppm, about 18.25 ppm, about 18.5 ppm, about 18.75 ppm, about 19 ppm, about 19.25 ppm, about 19.5 ppm, about 19.75 ppm, about 20 ppm, about 20.25 ppm, about 20.5 ppm, about 20.75 ppm, about 21 ppm, about 21.25 ppm, about 21.5 ppm, about 21.75 ppm, about 22 ppm, about 22.25 ppm, about 22.5 ppm, about 22.75 ppm, about 23 ppm, about 23.25 ppm, about 23.5 ppm, about 23.75 ppm, about 24 ppm, about 24.25 ppm, about 24.5 ppm, about 24.75 ppm, about 25 ppm, about 25.25 ppm, about 25.5 ppm, about 25.75 ppm, about 26 ppm, about 26.25 ppm, about 26.5 ppm, about 26.75 ppm, about 27 ppm, about 27.25 ppm, about 27.5 ppm, about 27.75 ppm, about 28 ppm, about 28.25 ppm, about 28.5 ppm, about 28.75 ppm, about 29 ppm, about 29.25 ppm, about 29.5 ppm, about 29.75 ppm, about 30 ppm, about 30.25 ppm, about 30.5 ppm, about 30.75 ppm, about 31 ppm, about 31.25 ppm, about 31.5 ppm, about 31.75 ppm, about 32 ppm, about 32.25 ppm, about 32.5 ppm, about 32.75 ppm, about 33 ppm, about 33.25 ppm, about 33.5 ppm, about 33.75 ppm, about 34 ppm, about 34.25 ppm, about 34.5 ppm, about 34.75 ppm, about 35 ppm, about 35.25 ppm, about 35.5 ppm, about 35.75 ppm, about 36 ppm, about 36.25 ppm, about 36.5 ppm, about 36.75 ppm, about 37 ppm, about 37.25 ppm, about 37.5 ppm, about 37.75 ppm, about 38 ppm, about 38.25 ppm, about 38.5 ppm, about 38.75 ppm, about 39 ppm, about 39.25 ppm, about 39.5 ppm, about 39.75 ppm, about 40 ppm, about 40.25 ppm, about 40.5 ppm, about 40.75 ppm, about 41 ppm, about 41.25 ppm, about 41.5 ppm, about 41.75 ppm, about 42 ppm, about 42.25 ppm, about 42.5 ppm, about 42.75 ppm, about 43 ppm, about 43.25 ppm, about 43.5 ppm, about 43.75 ppm, about 44 ppm, about 44.25 ppm, about 44.5 ppm, about 44.75 ppm, about 45 ppm, about 45.25 ppm, about 45.5 ppm, about 45.75 ppm, about 46 ppm, about 46.25 ppm, about 46.5 ppm, about 46.75 ppm, about 47 ppm, about 47.25 ppm, about 47.5 ppm, about 47.75 ppm, about 48 ppm, about 48.25 ppm, about 48.5 ppm, about 48.75 ppm, about 49 ppm, about 49.25 ppm, about 49.5 ppm, about 49.75 ppm, or about 50 ppm. In some embodiments, the remineralization composition comprises fluoride ions at a concentration from about 2 ppm to about 10 ppm. In some preferred embodiments, the remineralization composition comprises fluoride ions at a concentration from about 2 ppm to about 10 ppm, from about 2 ppm to about 2.25 ppm, from about 2 ppm to about 2.5 ppm, from about 2 ppm to about 2.75 ppm, from about 2 ppm to about 3 ppm, from about 2 ppm to about 3.25 ppm, from about 2 ppm to about 3.5 ppm, from about 2 ppm to about 3.75 ppm, from about 2 ppm to about 4 ppm, from about 2 ppm to about 4.25 ppm, from about 2 ppm to about 4.5 ppm, from about 2 ppm to about 4.75 ppm, from about 2 ppm to about 5 ppm, from about 2 ppm to about 5.25 ppm, from about 2 ppm to about 5.5 ppm, from about 2 ppm to about 5.75 ppm, from about 2 ppm to about 6 ppm, from about 2 ppm to about 6.25 ppm, from about 2 ppm to about 6.5 ppm, from about 2 ppm to about 6.75 ppm, from about 2 ppm to about 7 ppm, from about 2 ppm to about 7.25 ppm, from about 2 ppm to about 7.5 ppm, from about 2 ppm to about 7.75 ppm, from about 2 ppm to about 8 ppm, from about 2 ppm to about 8.25 ppm, from about 2 ppm to about 8.5 ppm, from about 2 ppm to about 8.75 ppm, from about 2 ppm to about 9 ppm, from about 2 ppm to about 9.25 ppm, from about 2 ppm to about 9.5 ppm, from about 2 ppm to about 9.75 ppm.

Inventors have discovered inter alia that remineralization compositions doped with strontium ions or stannous ions have a synergistic remineralization activity. As used herein, the term "synergistic", when used in conjunction with a description of the remineralization activity, is any combination of the components of the remineralization composition that is greater than the remineralization activity predicted from the sum of the effects of the individual components.

Accordingly, in some embodiments of any one of the aspects described herein, the remineralization composition comprises strontium ions or stannous ions. The strontium ions in the remineralization composition can be in form of a strontium salt. Exemplary strontium salts amenable to the various aspects described herein include, but are not limited to, strontium acetate, strontium chloride, strontium bromide, strontium nitrate, strontium citrate, strontium formate, strontium hydrogen phosphate, strontium gluconate, strontium ascorbate, strontium lactate, strontium glycinate, strontium carbonate, strontium sulfate, strontium hydroxide, and the like. In some preferred embodiments of the various aspects described herein, the strontium salt is strontium acetate. In other words, remineralization composition comprises strontium acetate.

The strontium ions can be doped into the remineralization composition at a concentration up to about 500 ppm. For example, the strontium ions can be present at concentration from about 0.05 ppm to about 300 ppm. In some embodiments of any one of the aspects described herein, the remineralization composition comprises strontium ions at a concentration from about 0.1 ppm to about 150 ppm, from about 0.2 ppm to about 125 ppm, from about 0.25 ppm to about 100 ppm, from about 0.5 ppm to about 75 ppm, or from about 0.75 ppm to about 50 ppm. For example, the strontium ions can be present in the remineralization composition in a concentration from about 1 ppm to about 20 ppm. In some embodiments of any one of the aspects described herein, the remineralization composition comprises strontium ions at a concentration from about 5 ppm to about 100 ppm. In some embodiments of any one of the aspects described herein, the remineralization composition comprises strontium ions at a concentration from about 10 ppm to about 50 ppm. In some embodiments, the remineralization composition comprises strontium ions at a concentration from about 20 ppm to about 150 ppm.

In some embodiments, the remineralization composition comprises strontium ions at a concentration about 0.1 ppm, about 0.15 ppm, about 0.2 ppm, about 0.25 ppm, about 0.5 ppm, about 0.75 ppm, about 1 ppm, about 1.25 ppm, about 1.5 ppm, about 1.75 ppm, about 2 ppm, about 2.25 ppm, about 2.5 ppm, about 2.75 ppm, about 3 ppm, about 3.25 ppm, about 3.5 ppm, about 3.75 ppm, about 4 ppm, about 4.25 ppm, about 4.5 ppm, about 4.75 ppm, about 5 ppm, about 5.25 ppm, about 5.5 ppm, about 5.75 ppm, about 6 ppm, about 6.25 ppm, about 6.5 ppm, about 6.75 ppm, about 7 ppm, about 7.25 ppm, about 7.5 ppm, about 7.75 ppm, about 8 ppm, about 8.25 ppm, about 8.5 ppm, about 8.75 ppm, about 9 ppm, about 9.25 ppm, about 9.5 ppm, about 9.75 ppm, about 10 ppm, about 10.25 ppm, about 10.5 ppm, about 10.75 ppm, about 11 ppm, about 11.25 ppm, about 11.5 ppm, about 11.75 ppm, about 12 ppm, about 12.25 ppm, about 12.5 ppm, about 12.75 ppm, about 13 ppm, about 13.25 ppm, about 13.5 ppm, about 13.75 ppm, about 14 ppm, about 14.25 ppm, about 14.5 ppm, about 14.75 ppm, about 15 ppm, about 15.25 ppm, about 15.5 ppm, about 15.75 ppm, about 16 ppm, about 16.25 ppm, about 16.5 ppm, about 16.75 ppm, about 17 ppm, about 17.25 ppm, about 17.5 ppm, about 17.75 ppm, about 18 ppm, about 18.25 ppm, about 18.5 ppm, about 18.75 ppm, about 19 ppm, about 19.25 ppm, about 19.5 ppm, about 19.75 ppm, about 20 ppm, about 20.25 ppm, about 20.5 ppm, about 20.75 ppm, about 21 ppm, about 21.25 ppm, about 21.5 ppm, about 21.75 ppm, about 22 ppm, about 22.25 ppm, about 22.5 ppm, about 22.75 ppm, about 23 ppm, about 23.25 ppm, about 23.5 ppm, about 23.75 ppm, about 24 ppm, about 24.25 ppm, about 24.5 ppm, about 24.75 ppm, about 25 ppm, about 25.25 ppm, about 25.5 ppm, about 25.75 ppm, about 26 ppm, about 26.25 ppm, about 26.5 ppm, about 26.75 ppm, about 27 ppm, about 27.25 ppm, about 27.5 ppm, about 27.75 ppm, about 28 ppm, about 28.25 ppm, about 28.5 ppm, about 28.75 ppm, about 29 ppm, about 29.25 ppm, about 29.5 ppm, about 29.75 ppm, about 30 ppm, about 30.25 ppm, about 30.5 ppm, about 30.75 ppm, about 31 ppm, about 31.25 ppm, about 31.5 ppm, about 31.75 ppm, about 32 ppm, about 32.25 ppm, about 32.5 ppm, about 32.75 ppm, about 33 ppm, about 33.25 ppm, about 33.5 ppm, about 33.75 ppm, about 34 ppm, about 34.25 ppm, about 34.5 ppm, about 34.75 ppm, about 35 ppm, about 35.25 ppm, about 35.5 ppm, about 35.75 ppm, about 36 ppm, about 36.25 ppm, about 36.5 ppm, about 36.75 ppm, about 37 ppm, about 37.25 ppm, about 37.5 ppm, about 37.75 ppm, about 38 ppm, about 38.25 ppm, about 38.5 ppm, about 38.75 ppm, about 39 ppm, about 39.25 ppm, about 39.5 ppm, about 39.75 ppm, about 40 ppm, about 40.25 ppm, about 40.5 ppm, about 40.75 ppm, about 41 ppm, about 41.25 ppm, about 41.5 ppm, about 41.75 ppm, about 42 ppm, about 42.25 ppm, about 42.5 ppm, about 42.75 ppm, about 43 ppm, about 43.25 ppm, about 43.5 ppm, about 43.75 ppm, about 44 ppm, about 44.25 ppm, about 44.5 ppm, about 44.75 ppm, about 45 ppm, about 45.25 ppm, about 45.5 ppm, about 45.75 ppm, about 46 ppm, about 46.25 ppm, about 46.5 ppm, about 46.75 ppm, about 47 ppm, about 47.25 ppm, about 47.5 ppm, about 47.75 ppm, about 48 ppm, about 48.25 ppm, about 48.5 ppm, about 48.75 ppm, about 49 ppm, about 49.25 ppm, about 49.5 ppm, about 49.75 ppm, about 50 ppm, about 50.25 ppm, about 50.5 ppm, about 50.75 ppm, about 51 ppm, about 51.25 ppm, about 51.5 ppm, about 51.75 ppm, about 52 ppm, about 52.25 ppm, about 52.5 ppm, about 52.75 ppm, about 53 ppm, about 53.25 ppm, about 53.5 ppm, about 53.75 ppm, about 54 ppm, about 54.25 ppm, about 54.5 ppm, about 54.75 ppm, about 55 ppm, about 55.25 ppm, about 55.5 ppm, about 55.75 ppm, about 56 ppm, about 56.25 ppm, about 56.5 ppm, about 56.75 ppm, about 57 ppm, about 57.25 ppm, about 57.5 ppm, about 57.75 ppm, about 58 ppm, about 58.25 ppm, about 58.5 ppm, about 58.75 ppm, about 59 ppm, about 59.25 ppm, about 59.5 ppm, about 59.75 ppm, about 60 ppm, about 60.25 ppm, about 60.5 ppm, about 60.75 ppm, about 61 ppm, about 61.25 ppm, about 61.5 ppm, about 61.75 ppm, about 62 ppm, about 62.25 ppm, about 62.5 ppm, about 62.75 ppm, about 63 ppm, about 63.25 ppm, about 63.5 ppm, about 63.75 ppm, about 64 ppm, about 64.25 ppm, about 64.5 ppm, about 64.75 ppm, about 65 ppm, about 65.25 ppm, about 65.5 ppm, about 65.75 ppm, about 66 ppm, about 66.25 ppm, about 66.5 ppm, about 66.75 ppm, about 67 ppm, about 67.25 ppm, about 67.5 ppm, about 67.75 ppm, about 68 ppm, about 68.25 ppm, about 68.5 ppm, about 68.75 ppm, about 69 ppm, about 69.25 ppm, about 69.5 ppm, about 69.75 ppm, about 70 ppm, about 70 ppm, about 70.25 ppm, about 80.5 ppm, about 70.75 ppm, about 71 ppm, about 71.25 ppm, about 71.5 ppm, about 71.75 ppm, about 72 ppm, about 72.25 ppm, about 72.5 ppm, about 72.75 ppm, about 73 ppm, about 73.25 ppm, about 73.5 ppm, about 73.75 ppm, about 74 ppm, about 74.25 ppm, about 74.5 ppm, about 74.75 ppm, about 75 ppm, about 75.25 ppm, about 75.5 ppm, about 75.75 ppm, about 76 ppm, about 76.25 ppm, about 76.5 ppm, about 76.75 ppm, about 77 ppm, about 77.25 ppm, about 77.5 ppm, about 77.75 ppm, about 78 ppm, about 78.25 ppm, about 78.5 ppm, about 78.75 ppm, about 79 ppm, about 79.25 ppm, about 79.5 ppm, about 79.75 ppm, about 80 ppm, about 80.25 ppm, about 80.5 ppm, about 80.75 ppm, about 81 ppm, about 81.25 ppm, about 81.5 ppm, about 81.75 ppm, about 82 ppm, about 82.25 ppm, about 82.5 ppm, about 82.75 ppm, about 83 ppm, about 83.25 ppm, about 83.5 ppm, about 83.75 ppm, about 84 ppm, about 84.25 ppm, about 84.5 ppm, about 84.75 ppm, about 85 ppm, about 85.25 ppm, about 85.5 ppm, about 85.75 ppm, about 86 ppm, about 86.25 ppm, about 86.5 ppm, about 86.75 ppm, about 87 ppm, about 87.25 ppm, about 87.5 ppm, about 87.75 ppm, about 88 ppm, about 88.25 ppm, about 88.5 ppm, about 88.75 ppm, about 89 ppm, about 89.25 ppm, about 89.5 ppm, about 89.75 ppm, about 80 ppm, about 90.25 ppm, about 90.5 ppm, about 90.75 ppm, about 91 ppm, about 91.25 ppm, about 91.5 ppm, about 91.75 ppm, about 92 ppm, about 92.25 ppm, about 92.5 ppm, about 92.75 ppm, about 93 ppm, about 93.25 ppm, about 93.5 ppm, about 93.75 ppm, about 94 ppm, about 94.25 ppm, about 94.5 ppm, about 94.75 ppm, about 95 ppm, about 95.25 ppm, about 95.5 ppm, about 95.75 ppm, about 96 ppm, about 96.25 ppm, about 96.5 ppm, about 96.75 ppm, about 97 ppm, about 97.25 ppm, about 97.5 ppm, about 97.75 ppm, about 98 ppm, about 98.25 ppm, about 98.5 ppm, about 98.75 ppm, about 99 ppm, about 99.25 ppm, about 99.5 ppm, about 99.75 ppm, or about 100 ppm.

In some preferred embodiments, the remineralization composition comprises strontium ions at a concentration from about 1 ppm to about 5 ppm. For example, the remineralization composition comprises strontium ions at a concentration from about 1 ppm to about 1.25 ppm, from about 1 ppm to about 1.5 ppm, from about 1 ppm to about 1.75 ppm, from about 1 ppm to about 2 ppm, from about 1 ppm to about 2.25 ppm, from about 1 ppm to about 2.5 ppm, from about 1 ppm to about 2.75 ppm, from about 1 ppm to about 3 ppm, from about 1 ppm to about 3.25 ppm, from about 1 ppm to about 3.5 ppm, from about 1 ppmo about 3.75 ppm, from about 1 ppm to about 4 ppm, from about 1 ppm to about 4.25 ppm, from about 1 ppm to about 4.5 ppm, from about 1 ppm to about 4.75 ppm.

In some preferred embodiments, the remineralization composition comprises strontium ions at a concentration from about 20 ppm to about 50 ppm. For example, the remineralization composition comprises strontium ions at a concentration from about 20 ppm to about 22.5 ppm, from about 20 ppm to about 25 ppm, from about 20 ppm to about 27.5 ppm, from about 20 ppm to about 30 ppm, from about 20 ppm to about 32.5 ppm, from about 20 ppm to about 35 ppm, from about 20 ppm to about 37.5 ppm, from about 20 ppm to about 40 ppm, from about 20 ppm to about 42.5 ppm, from about 20 ppm to about 45 ppm, from about 20 ppm to about 47.5 ppm.

In some embodiments of any one of the aspects described herein, the composition comprises stannous. For example, the composition can comprise stannous in form of a stannous salt, e.g., tin chloride or tin fluoride. When present the stannous ions can be present in a concentration from about 0.1 ppm to about 50 ppm, e.g., 1 ppm to 50 ppm. In some embodiments, the composition comprises stannous ions in a concentration from about 0.2 ppm to about 25 ppm. For example, the composition comprises stannous ions in a concentration from about 0.25 ppm to about 20 ppm. In some embodiments, the composition comprises stannous ions in a concentration from about 0.3 ppm to about 15 ppm. For example, the composition comprises stannous ions in a concentration from about 0.4 ppm to about 10 ppm. In some preferred embodiments, the composition comprises stannous ions in a concentration from about 0.5 ppm to about 5 ppm.

In some embodiments of any one of the aspects described herein, the remineralization composition comprises calcium chloride, potassium phosphate, sodium fluoride and strontium acetate. For example, the composition comprises the composition comprises calcium ions in a concentration from about 2 mM to about 5 mM, phosphate ions in a concentration from about 0.5 mM to about 5 mM, fluoride ions in a concentration from about 2 ppm to about 20 ppm, and strontium in a concentration from about 10 ppm to about 200 ppm or stannous in a concentration from about 0.1 ppm to about 10 ppm. In some embodiments, the remineralization composition comprises calcium ions in a concentration from about 2 mM to about 5 mM; phosphate ions in a concentration from about 3 mM to about 9 mM; fluoride ions in a concentration from about 2 ppm to about 30 ppm; and strontium in a concentration from about 1 ppm to about 20 ppm.

In some embodiments, the composition comprises calcium ions in a concentration from about 2 mM to about 5 mM, phosphate ions in a concentration from about 0.5 mM to about 5 mM, fluoride ions in a concentration from about 2 ppm to about 20 ppm, and stannous in a concentration from about 0.1 ppm to about 10 ppm.

Generally, the remineralization composition has an ionic strength of from about 100 mM to about 500 mM. The term "ionic strength" refers to a measure of the concentration of ions in a solution. Ionic strength, also known as the molar ionic strength, can be measured by the equation $$= \frac{1}{2}\sum_{i=1}^{n} c_i z_i^2,$$

where $c_i$ is the molar concentration of ion i (M, mol/L), $z_i$ is the charge number of that ion, and the sum is taken over all ions in the solution.

The ionic strength can result from any ions in solution, but preferably, the ionic strength can result from sodium chloride, potassium chloride, potassium nitrate, ammonium chloride, stannous (Tin II) ions, and/or strontium (Sr II) ions. For example, the composition can have an ionic strength from about 50 mM to about 500 mM. In some embodiments, the composition comprises an ionic strength from about 75 mM to about 400 mM. For example, the composition has an ionic strength from about 100 mM to about 300 mM. In some embodiments, the composition has an ionic strength from about 125 mM to about 250 mM. In some preferred embodiments, the composition comprises an ionic strength from about 150 mM to about 200 mM.

In some embodiments, the remineralization composition can contain strontium in a concentration from about 0.05 ppm to about 100 ppm or stannous in a concentration from about 0.1 ppm to about 50 ppm, and wherein the composition has an ionic strength of about 50 mM to about 500 mM.

In some embodiments of any one of the aspects described herein, the composition comprises sodium ions. For example, the composition comprises sodium ions in a concentration from about 100 mM to about 300 mM. In some embodiments, the composition comprises sodium ions in a concentration from about 125 mM to about 250 mM or from about 150 mM to about 200 mM. In some embodiments, the composition comprises sodium ions in a concentration from about 160 mM to about 190 mM. For example, the composition comprises sodium ions in a concentration from about 165 mM to about 180 mM. In some embodiments, the composition comprises sodium ions in a concentration from about 170 mM to about 175 mM, e.g., about 173 mM.

Sodium ions can in the form of salt, e.g., sodium chloride. Accordingly, in some embodiments, the composition further comprises sodium chloride. For example, the composition further comprises sodium chloride in a concentration from about 100 mM to about 300 mM. In some embodiments, the composition comprises sodium chloride in a concentration from about 125 mM to about 250 mM or from about 150 mM to about 200 mM. In some embodiments, the composition comprises sodium chloride in a concentration from about 160 mM to about 190 mM. For example, the composition comprises sodium chloride in a concentration from about 165 mM to about 180 mM. In some preferred embodiments, the composition comprises sodium chloride in a concentration from about 170 mM to about 175 mM, e.g., about 173 mM.

In some embodiments of the various aspects described herein, the remineralization composition has a pH of from about 6 to about 8, e.g., at room temperature. For example, the remineralization composition has a pH of from about 6.5 to about 7.5, e.g., at room temperature. In some embodiments of any one of the aspects described herein, the remineralization composition has a pH of about 6.1, about 6.2, about 6.3, about 6.4 about 6.5, about 6.6, about 6.7, about 6.8, about 6.9, about 7, about 7.1, about 7.2, about 7.3, about 7.4 about 7.5, about 7.6, about 7.7, about 7.8, about 7.9, or about 8. It is noted that pH of the remineralization composition can be adjusted by adding a pH agent or buffering agent. The term "pH agent" or "buffering agent" as used herein refers to a compound or buffer useful as a pH adjusting agent. Such can include, but is not limited to, glycerol buffer, citrate buffer, borate buffer, acetate buffer, gluconate buffer, phosphate buffer, or citrate-phosphate buffer.

Accordingly, in some embodiments of any one of the aspects described herein, the remineralization composition comprises a pH agent in an amount sufficient to adjust the pH of the remineralization composition to between from about 6 to about 8. For example, the remineralization composition comprises a pH agent in an amount sufficient to adjust the pH of the remineralization composition to between from about 6.5 to about 7.5. In some embodiments of any one of the aspects described herein, the remineralization composition comprises a pH agent in an amount sufficient to adjust the pH of the remineralization composition to a pH of about 6.1, about 6.2, about 6.3, about 6.4 about 6.5, about 6.6, about 6.7, about 6.8, about 6.9, about 7, about 7.1, about 7.2, about 7.3, about 7.4 about 7.5, about 7.6, about 7.7, about 7.8, about 7.9, or about 8.

In some embodiments of any one of the aspects described herein, the remineralization composition comprises a buffering agent. For example, the remineralization composition comprises a buffering agent in amount sufficient to adjust the pH of the remineralization composition to between from about 6 to about 8, e.g., at room temperature. In some embodiments, the remineralization composition comprises a buffering agent in an amount sufficient to adjust the pH of the remineralization composition to between from about 6.5 to about 7.5. In some embodiments of any one of the aspects described herein, the remineralization composition comprises a buffering agent in an amount sufficient to adjust the pH of the remineralization composition to a pH of about 6.1, about 6.2, about 6.3, about 6.4 about 6.5, about 6.6, about 6.7, about 6.8, about 6.9, about 7, about 7.1, about 7.2, about 7.3, about 7.4 about 7.5, about 7.6, about 7.7, about 7.8, about 7.9, or about 8.

In some embodiments of any one of the aspects described herein, the remineralization composition can comprise a buffering agent in a concentration up to about 150 mM. For example, the remineralization composition can comprise a buffering agent in a concentration from about 10 mM to about 150 mM.

Some exemplary buffering agents amenable to the various aspects described herein include, but are not limited to, 4-(2-hydroxyethyl)-1 piperazineethanesulfonic acid (HEPES), tris(hydroxymethyl) aminomethane (Tris), citrate, 2-(N 15 morpholino)ethanesulfonic acid (MES), N,N-Bis(2-hydroxyethyl)-2-aminoethanesulfonic acid (BES), 1,3-bis (tris(hydroxymethyl) methylamino)propane (Bis-Tris), 3-(N-morpholino)propanesulfonic acid (MOPS), N,N-bis(2-hydroxyethyl) glycine (Bicine), N-[tris(hydroxymethyl) methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), or any combination thereof. In some preferred embodiments, the buffering agent is HEPES.

In some embodiments of any one of the aspects described herein, the remineralization composition comprises calcium chloride, potassium phosphate, sodium fluoride and strontium acetate. For example, the remineralization composition comprises calcium ions in a concentration from about 2 mM to about 5 mM; phosphate ions in a concentration from about 3 mM to about 9 mM; fluoride ions in a concentration from about 2 ppm to about 30 ppm; and strontium in a concentration from about 1 ppm to about 20 ppm, and the composition has a pH of from about 6 to about 8.

It is noted the strontium ions in the remineralization composition can be replaced with one or more of magnesium, stannous and zinc. Alternatively, the remineralization composition can comprise, in addition to strontium ions, one or more of magnesium, stannous and zinc.

Thus, in some embodiments, the remineralization composition comprises magnesium. For example, the remineralization composition comprises magnesium ions. The magnesium ions in the remineralization composition can be in form of a magnesium salt. Exemplary magnesium salts amenable to the various aspects described herein include, but are not limited to, magnesium chloride, magnesium acetate, magnesium benzoate, magnesium citrate, magnesium formate, magnesium hexafluorosilicate, magnesium hydroxide, magnesium lactate, magnesium molybdate, magnesium nitrate, magnesium perchlorate, magnesium phosphonate, magnesium salicylate, magnesium sulfate, magnesium sulfite, and the like.

The magnesium ions can be doped into the remineralization composition at a concentration up to about 500 ppm. For example, the magnesium ions can be present at concentration from about 0.05 ppm to about 300 ppm. In some embodiments of any one of the aspects described herein, the remineralization composition comprises magnesium ions at a concentration from about 0.1 ppm to about 250 ppm, from about 0.2 ppm to about 200 ppm, from about 0.25 ppm to about 175 ppm, from about 0.5 ppm to about 150 ppm, or from about 0.75 ppm to about 100 ppm. For example, the magnesium ions can be present in the remineralization composition in a concentration from about 1 ppm to about 50 ppm. In some preferred embodiments, the remineralization composition comprises magnesium ions at a concentration from about 2 ppm to about 10 ppm, from about 2 ppm to about 9.5 ppm, from about 2 ppm to about 9 ppm, from about 2 ppm to about 8.5 ppm, from about 2 ppm to about 8 ppm, from about 2 ppm to about 7.5 ppm, from about 2 ppm to about 7 ppm, from about 2 ppm to about 6.5 ppm, from about 2 ppm to about 6 ppm, from about 2 ppm to about 5.5 ppm, from about 2 ppm to about 5 ppm, from about 2 ppm to about 4.5 ppm, from about 2 ppm to about 4 ppm, from about 2 ppm to about 3.5 ppm, from about 2 ppm to about 3 ppm, from about 2 ppm to about 2.5 ppm.

In some embodiments, the remineralization composition comprises stannous. For example, the remineralization composition comprises stannous ions. The stannous ions in the remineralization composition can be in form of a stannous salt. Exemplary stannous salts amenable to the various aspects described herein include, but are not limited to, tin fluoride, tin chloride, tin bromide, tin iodide, tin cyanide and tin isothiocyanide, tin nitrate, tin sulfate, tin phosphate, and the like.

The stannous ions can be doped into the remineralization composition at a concentration up to about 500 ppm. For example, the stannous ions can be present at concentration from about 0.05 ppm to about 300 ppm. In some embodiments of any one of the aspects described herein, the remineralization composition comprises stannous ions at a concentration from about 0.1 ppm to about 250 ppm, from about 0.2 ppm to about 200 ppm, from about 0.25 ppm to about 175 ppm, from about 0.5 ppm to about 150 ppm, or from about 0.75 ppm to about 100 ppm. For example, the stannous ions can be present in the remineralization composition in a concentration from about 1 ppm to about 50 ppm.

In some embodiments, the remineralization composition comprises zinc. For example, the remineralization composition comprises zinc ions. The zinc ions in the remineralization composition can be in form of a zinc salt. Exemplary zinc salts amenable to the various aspects described herein include, but are not limited to, zinc oxide, zinc acetate, zinc borate, zinc nitrate, zinc sulfate, zinc chloride, zinc chlorate, zinc bromide, zinc nitrate, zinc hydrophosphite, zinc oxalate, zinc oleate, zinc peroxide, zinc citrate, zinc gluconate, zinc malate, zinc tartrate, zinc carbonate, zinc phosphate, zinc molybdate, zinc chromate, zinc arsenite, zinc arsenate octahydrate), zinc bromide dehydrate, zinc citrate dihydrate, zinc cyanide, zinc fluoride, zinc hexafluorosilicate, zinc iodide, zinc methacrylate, zinc nitrate hydrate, zinc oxalate hydrate, zinc perchlorate hexahydrate, zinc selenite, zinc sulfate heptahydrate, zinc tetrafluoroborate hydrate, zinc p-toluenesulfonate hydrate, and the like.

The zinc ions can be doped into the remineralization composition at a concentration up to about 500 ppm. For example, the zinc ions can be present at concentration from about 0.05 ppm to about 300 ppm. In some embodiments of any one of the aspects described herein, the remineralization composition comprises zinc ions at a concentration from about 0.1 ppm to about 250 ppm, from about 0.2 ppm to about 200 ppm, from about 0.25 ppm to about 175 ppm, from about 0.5 ppm to about 150 ppm, or from about 0.75 ppm to about 100 ppm. For example, the zinc ions can be present in the remineralization composition in a concentration from about 1 ppm to about 50 ppm. In some preferred embodiments, the remineralization composition comprises zinc ions at a concentration from about 5 ppm to about 20 ppm, from about 5 ppm to about 19 ppm, from about 5 ppm to about 18 ppm, from about 5 ppm to about 17 ppm, from about 5 ppm to about 16 ppm, from about 5 ppm to about 15 ppm, from about 5 ppm to about 14 ppm, from about 5 ppm to about 13 ppm, from about 5 ppm to about 12 ppm, from about 5 ppm to about 11 ppm, from about 5 ppm to about 10 ppm, from about 5 ppm to about 9 ppm, from about 5 ppm to about 8 ppm, from about 5 ppm to about 7 ppm, from about 5 ppm to about 6 ppm.

The remineralization composition described herein can be a supersaturated solution. The term "supersaturated," as used herein, means having a compound in a solvent in which it is completely dissolved at a certain temperature but at which the solubility of the compound in the solvent at that certain temperature is exceeded. In other words, the term "supersaturated" refers to a solution that contains more of a dissolved material than a saturated solution.

The remineralization compositions described herein can include additional components. For example, the remineralization compositions described herein can include one or more components used in oral care compositions. Such components include, but are not limited to flavoring agents, sweeteners, surfactants, thickening agents, anti-calculus agents, dental abrasive agents, binders, coloring agents, preservatives, and humectants.

In some embodiments of any one of the aspects described herein, the remineralization composition comprises a flavoring agent. The flavoring agents in conventional oral care compositions are generally selected and dosed to overcome any unpleasant taste or mouthfeel from the active ingredients and/or carrier ingredients. Thus, generally, the remineralization composition described herein contains only sufficient amount of flavoring agent to counteract any distinctly distasteful experience that might discourage use of the composition entirely. For example, the remineralization composition described herein can comprise a flavoring agent in an amount greater than 0% and less than about 5%, by weight of the composition. In some embodiments, the remineralization composition described herein can comprise a flavoring agent in an amount from about 0.01% to about 4.5%, by weight of the composition. For example, the remineralization composition described herein can comprise a flavoring agent in an amount from about 0.05% to about 4%, or from about 0.1% to about 3.5%, or from about 0.2% to about 3%, or from about 0.3% to about 2.5%, or from about 0.4% to about 2%, or from about 0.5% to about 1.75%, or from about 1% to about 5%, by weight of the composition.

Flavoring agents can include sweeteners, natural flavors, artificial flavors, or sensates that create a sensation of coolness or warmth in the mouth, or combinations thereof. Some exemplary flavoring agents include, but are not limited to, is spearmint oil, peppermint oil, wintergreen oil, sassafras oil, clove oil, sage oil, eucalyptus oil, poplar oil, cinnamon oil, lemon oil, grape and grapefruit oil, orange peel oil, methyl salicylate and eugenol, clover oil, hay oil, anise oil, eucalyptus, vanilla, menthol, carvone, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, anethole and dihydrochalcones.

In some embodiments of any one of the aspects described herein, the remineralization composition further comprises a sweetener. For example, the remineralization composition can comprise a sweetener in an amount up to about 3%, by weight of the composition. In some embodiments of any one of the aspects described herein, the remineralization composition comprises a sweetener in an amount from about 0.1% to about 3%, from about 0.2% to about 3%, from about 0.3% to about 3%, from about 0.4% to about 3%, from about 0.5% to about 3%, from about 0.6% to about 3%, from about 0.7% to about 3%, from about 0.8% to about 3%, from about 0.9% to about 3%, from about 1% to about 3%, from about 1.1% to about 3%, from about 1.2% to about 3%, from about 1.3% to about 3%, from about 1.4% to about 3%, from about 1.5% to about 3%, from about 1.6% to about 3%, from about 1.7% to about 3%, from about 1.8% to about 3%, from about 1.9% to about 3%, from about 2% to about 3%, from about 2.1% to about 3%, from about 2.2% to about 3%, from about 2.3% to about 3%, from about 2.4% to about 3%, from about 2.5% to about 3%, from about 2.6% to about 3%, from about 2.7% to about 3%, from about 2.8% to about 3%, or from about 2.9% to about 3%, by weight of the composition.

In some embodiments of any one of the aspects described herein, the remineralization composition comprises a sweetener in an amount from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.1% to about 0.9%, from about 0.1% to about 1.0%, from about 0.1% to about 1.1%, from about 0.1% to about 1.2%, from about 0.1% to about 1.3%, from about 0.1% to about 1.4%, from about 0.1% to about 1.5%, from about 0.1% to about 1.6%, from about 0.1% to about 1.7%, from about 0.1% to about 1.8%, from about 0.1% to about 1.9%, from about 0.1% to about 2.0%, from about 0.1% to about 2.1%, from about 0.1% to about 2.2%, from about 0.1% to about 2.3%, from about 0.1% to about 2.4%, from about 0.1% to about 2.5%, from about 0.1% to about 2.6%, from about 0.1% to about 2.7%, from about 0.1% to about 2.8%, or from about 0.1% to about 2.9%, by weight of the composition.

The remineralization compositions described herein can also include surfactant, also commonly referred to as sudsing agents. For example, the remineralization composition can comprise surfactant in an amount up to about 2.5%, by weight of the composition. In some embodiments of any one of the aspects described herein, the remineralization composition comprises a surfactant in an amount from about 0.1% to about 2.5%, from about 0.2% to about 2.5%, from about 0.3% to about 2.5%, from about 0.4% to about 2.5%, from about 0.5% to about 2.5%, from about 0.6% to about 2.5%, from about 0.7% to about 2.5%, from about 0.8% to about 2.5%, from about 0.9% to about 2.5%, from about 1% to about 2.5%, from about 1.1% to about 2.5%, from about 1.2% to about 2.5%, from about 1.3% to about 2.5%, from about 1.4% to about 2.5%, from about 1.5% to about 2.5%, from about 1.6% to about 2.5%, from about 1.7% to about 2.5%, from about 1.8% to about 2.5%, from about 1.9% to about 2.5%, from about 2% to about 2.5%, from about 2.1% to about 2.5%, from about 2.2% to about 2.5%, from about 2.3% to about 2.5%, or from about 2.4% to about 2.5%, by weight of the composition.

In some embodiments of any one of the aspects described herein, the remineralization composition comprises a surfactant in an amount from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.1% to about 0.9%, from about 0.1% to about 1.0%, from about 0.1% to about 1.1%, from about 0.1% to about 1.2%, from about 0.1% to about 1.3%, from about 0.1% to about 1.4%, from about 0.1% to about 1.5%, from about 0.1% to about 1.6%, from about 0.1% to about 1.7%, from about 0.1% to about 1.8%, from about 0.1% to about 1.9%, from about 0.1% to about 2.0%, from about 0.1% to about 2.1%, from about 0.1% to about 2.2%, from about 0.1% to about 2.3%, from about 0.1% to about 2.4%, or from about 0.1% to about 2.5%, by weight of the composition.

An alternative approach to the remineralization composition is using a two-part component formulation. Each component has many years of stability when kept separate. Two components can be kept from coming into contact prior to use by usual means known to one of skill in the art. In one embodiment, each component is packaged in separate containers and mixed prior to use. In another embodiment, one component is applied to the surface first, and the second component is applied on top of the first component. Exemplary examples of surfaces include, but are not limited to dentin, a customer tray, natural enamel, and/or synthetic enamel. The order of the components can be reversed. In a further embodiment, each component is packaged together in the same container with a barrier between the two components and are mixed when the components are extracted from the container. When the components are mixed together before use, the supersaturated solution can be stable for at least one day, at least two days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days or more.

Suitable surfactants are those which are reasonably stable and foam throughout a wide pH range. It is noted the surfactant can be an anionic, nonionic, cationic, zwitterionic or amphoteric surfactant. Anionic surfactants useful in the remineralization compositions described herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Nonionic surfactants which can be used in the remineralization compositions described herein can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic®), polyoxyethylene, polyoxyethylene sorbitan esters (sold under trade name Tweens®), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the remineralization compositions described herein can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

In some embodiments of anyone of the aspects described herein, the remineralization composition comprises one or more surfactants selected independently from the group consisting of sodium lauroyl sarcosine, potassium lauroyl sarcosine, aodium coco acylsarcosinate, cocoyl flesh Propylhomoserin potassium, sodium lauroylmethyl taurate, sodium cocoyl methyl sodium taurocholate, sodium lauroyl glutamate, lauryl trimethyl ammonium chloride, stearyl trimethyl ammonium chloride, benzethonium chloride, cetyl pyridinium chloride, cetyl pyridinium chloride benzalkonium chloride, stearyl dimethyl benzyl ammonium chloride, polyoxyethylene lauryl ether sodium sulfate, sodium lauryl sulfate, sodium myristyl sulfate, sodium N-lauroyl sarcosinate, sodium N-myristol sarcosine, sodium dodecylbenzene sulfonate, sodium coconut fatty acid monoglyceride monosulfate, sodium lauryl sulfoacetate, sodium α-olefin sulfonate, sodium N-palmitoyl glutamate, sodium N-methyl-N-acyl taurate, sucrose fatty acid ester, maltose fatty acid ester, maltitol fatty acid ester, lactol fatty acid ester, sorbitan fatty acid ester, polyoxyethylene sorbitan monostearate, polyoxyethylene higher alcohol ether, polyoxyethylene cured Castor oil, polyoxyethylene polyoxypropylene copolymer, polyoxyethylene polyoxypropylene fatty acid ester, polyglycerin fatty acid ester, coconut oil fatty acid amidopropyl betaine, lauryldimethylaminoacetic acid betaine, lauryldimethylamine oxide, 2-alkyl-N-carboxymethyl-N-hydroxyethylimidazolium betaine, N-lauryldiaminoethylglycine, N-myristyldiaminoethylglycine, sodium N-alkyl-1-hydroxyethylimidazoline betaine, and any combination thereof.

In some embodiments of any one of the aspects described herein, the remineralization composition can comprise a thickening agent. For example, the remineralization composition can comprise a thickening agent in an amount up to about 5%, by weight of the composition. In some embodiments of any one of the aspects described herein, the remineralization composition can comprise a thickening agent in an amount from about 0.1% to about 5%, from about 0.2% to about 5%, from about 0.3% to about 5%, from about 0.4% to about 5%, from about 0.5% to about 5%, from about 0.6% to about 5%, from about 0.7% to about 5%, from about 0.8% to about 5%, from about 0.9% to about 5%, from about 1.0% to about 5%, from about 1.1% to about 5%, from about 1.2% to about 5%, from about 1.3% to about 5%, from about 1.4% to about 5%, from about 1.5% to about 5%, from about 1.6% to about 5%, from about 1.7% to about 5%, from about 1.8% to about 5%, from about 1.9% to about 5%, from about 2.0% to about 5%, from about 2.1% to about 5%, from about 2.2% to about 5%, from about 2.3% to about 5%, from about 2.4% to about 5%, from about 2.5% to about 5%, from about 2.6% to about 5%, from about 2.7% to about 5%, from about 2.8% to about 5%, from about 2.9% to about 5%, from about 3% to about 5%, from about 3.1% to about 5%, from about 3.2% to about 5%, from about 3.3% to about 5%, from about 3.4% to about 5%, from about 3.5% to about 5%, from about 3.6% to about 5%, from about 3.7% to about 5%, from about 3.8% to about 5%, from about 3.9% to about 5%, from about 4% to about 5%, from about 4.1% to about 5%, from about 4.2% to about 5%, from about 4.3% to about 5%, from about 4.4% to about 5%, from about 4.5% to about 5%, from about 4.6% to about 5%, from about 4.7% to about 5%, from about 4.8% to about 5%, or from about 4.9% to about 5%, by weight of the composition.

In some embodiments of any one of the aspects described herein, the remineralization composition can comprise a thickening agent in an amount from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.1% to about 0.9%, from about 0.1% to about 1.0%, from about 0.1% to about 1.1%, from about 0.1% to about 1.2%, from about 0.1% to about 1.3%, from about 0.1% to about 1.4%, from about 0.1% to about 1.5%, from about 0.1% to about 1.6%, from about 0.1% to about 1.7%, from about 0.1% to about 1.8%, from about 0.1% to about 1.9%, from about 0.1% to about 2.0%, from about 0.1% to about 2.1%, from about 0.1% to about 2.2%, from about 0.1% to about 2.3%, from about 0.1% to about 2.4%, from about 0.1% to about 2.5%, from about 0.1% to about 2.6%, from about 0.1% to about 2.7%, from about 0.1% to about 2.8%, from about 0.1% to about 2.9%, from about 0.1% to about 3%, from about 0.1% to about 3.1%, from about 0.1% to about 3.2%, from about 0.1% to about 3.3%, from about 0.1% to about 3.4%, from about 0.1% to about 3.5%, from about 0.1% to about 3.6%, from about 0.1% to about 3.7%, from about 0.1% to about 3.8%, from about 0.1% to about 3.9%, from about 0.1% to about 4%, from about 0.1% to about 4.1%, from about 0.1% to about 4.2%, from about 0.1% to about 4.3%, from about 0.1% to about 4.4%, from about 0.1% to about 4.5%, from about 0.1% to about 4.6%, from about 0.1% to about 4.7%, from about 0.1% to about 4.8%, from about 0.1% to about 4.9%, from about 0.1% to 5%, by weight of the composition.

Exemplary thickening agents include, but are not limited to, polymers (such as polyacrylic acid crosslinked with polyallyl sucrose or polyallyl pentaerythritol), hydroxyethyl cellulose, hydroxypropyl cellulose, water soluble salts of cellulose ethers (such as sodium carboxymethyl cellulose and sodium carboxymethyl hydroxyethyl cellulose), natural gums (such as carrageenan, karaya gum, guar gum, xanthan gum, gum arabic and tragacanth), finely divided silica, laponite, colloidal magnesium aluminum silicate and mixtures thereof.

In some embodiments of any one of the aspects described herein, the remineralization composition comprise a thickening agent selected from the group consisting of glycerin, sorbitol, ethylene glycol, propylene glycol, polyethylene glycol, polypropylene glycol, xylitol, maltitol, lactol, carrageenan, sodium carboxymethylcellulose, methylcellulose, sodium hydroxyethylcellulose, sodium alginate, tragacanth gum, karaya gum, arabiya gum, locust bean gum, polyvinyl alcohol, sodium polyacrylate, carboxyvinyl polymer, carbopol, silica gel, aluminum silica gel, Bee gum, laponite, thickening silica, and any combination thereof.

In some embodiments of any one of the aspects described herein, the remineralization composition can comprise an anti-calculus agent. As used herein, the term "anti-calculus agent" refers to a compound that is capable of preventing, reducing, inhibiting or removing dental calculus. Some exemplary anti-calculus agents include, but are not limited to, pyrophosphate salts, polyaminopropanesulfonic acid (AMPS), hexarnetaphosphate salts, zinc citrate trihydrate, polypeptides, polyolefin sulfonates, polyolefin phosphates, diphosphonates, and the like.

The anti-calculus agent can be included in the remineralization compositions in an amount up to 15%, by weight of the composition. For example, the remineralization composition can comprise an anti-calculus agent in an amount from about 0.1% to about 15%, from about 0.2% to about 15%, from about 0.3% to about 15%, from about 0.4% to about 15%, from about 0.5% to about 15%, from about 0.6% to about 15%, from about 0.7% to about 15%, from about 0.8% to about 15%, from about 0.9% to about 15%, from about 1.0% to about 15%, from about 1.1% to about 15%, from about 1.2% to about 15%, from about 1.3% to about 15%, from about 1.4% to about 15%, from about 1.5% to about 15%, from about 1.6% to about 15%, from about 1.7% to about 15%, from about 1.8% to about 15%, from about 1.9% to about 15%, from about 2.0% to about 15%, from about 2.1% to about 15%, from about 2.2% to about 15%, from about 2.3% to about 15%, from about 2.4% to about 15%, from about 2.5% to about 15%, from about 2.6% to about 15%, from about 2.7% to about 15%, from about 2.8% to about 15%, from about 2.9% to about 15%, from about 3% to about 15%, from about 3.1% to about 15%, from about 3.2% to about 15%, from about 3.3% to about 15%, from about 3.4% to about 15%, from about 3.5% to about 15%, from about 3.6% to about 15%, from about 3.7% to about 15%, from about 3.8% to about 15%, from about 3.9% to about 15%, from about 4% to about 15%, from about 4.1% to about 15%, from about 4.2% to about 15%, from about 4.3% to about 15%, from about 4.4% to about 15%, from about 4.5% to about 15%, from about 4.6% to about 15%, from about 4.7% to about 15%, from about 4.8% to about 15%, from about 4.9% to about 15%, from about 5% to about 15%, from about 5.1% to about 15%, from about 5.2% to about 15%, from about 5.3% to about 15%, from about 5.4% to about 15%, from about 5.5% to about 15%, from about 5.6% to about 15%, from about 5.7% to about 15%, from about 5.8% to about 15%, from about 5.9% to about 15%, from about 6.0% to about 15%, from about 6.1% to about 15%, from about 6.2% to about 15%, from about 6.3% to about 15%, from about 6.4% to about 15%, from about 6.5% to about 15%, from about 6.6% to about 15%, from about 6.7% to about 15%, from about 6.8% to about 15%, from about 6.9% to about 15%, from about 7% to about 15%, from about 7.1% to about 15%, from about 7.2% to about 15%, from about 7.3% to about 15%, from about 7.4% to about 15%, from about 7.5% to about 15%, from about 7.6% to about 15%, from about 7.7% to about 15%, from about 7.8% to about 15%, from about 7.9% to about 15%, from about 8% to about 15%, from about 8.1% to about 15%, from about 8.2% to about 15%, from about 8.3% to about 15%, from about 8.4% to about 15%, from about 8.5% to about 15%, from about 8.6% to about 15%, from about 8.7% to about 15%, from about 8.8% to about 15%, from about 8.9% to about 15%, from about 9.0% to about 15%, from about 9.1% to about 15%, from about 9.2% to about 15%, from about 9.3% to about 15%, from about 9.4% to about 15%, from about 9.5% to about 15%, from about 9.6% to about 15%, from about 9.7% to about 15%, from about 9.8% to about 15%, from about 9.9% to about 15%, from about 10.0% to about 15%, from about 10.1% to about 15%, from about 10.2% to about 15%, from about 10.3% to about 15%, from about 10.4% to about 15%, from about 10.5% to about 15%, from about 10.6% to about 15%, from about 10.7% to about 15%, from about 10.8% to about 15%, from about 10.9% to about 15%, from about 11% to about 15%, from about 11.1% to about 15%, from about 11.2% to about 15%, from about 11.3% to about 15%, from about 11.4% to about 15%, from about 11.5% to about 15%, from about 11.6% to about 15%, from about 11.7% to about 15%, from about 11.8% to about 15%, from about 11.9% to about 15%, from about 12% to about 15%, from about 12.1% to about 15%, from about 12.2% to about 15%, from about 12.3% to about 15%, from about 12.4% to about 15%, from about 12.5% to about 15%, from about 12.6% to about 15%, from about 12.7% to about 15%, from about 12.8% to about 15%, from about 12.9% to about 15%, from about 13% to about 15%, from about 13.1% to about 15%, from about 13.2% to about 15%, from about 13.3% to about 15%, from about 13.4% to about 15%, from about 13.5% to about 15%, from about 13.6% to about 15%, from about 13.7% to about 15%, from about 13.8% to about 15%, from about 13.9% to about 15%, from about 14% to about 15%, from about 14.1% to about 15%, from about 14.2% to about 15%, from about 14.3% to about 15%, from about 14.4% to about 15%, from about 14.5% to about 15%, from about 14.6% to about 15%, from about 14.7% to about 15%, from about 14.8% to about 15%, or from about 14.9% to about 15%, by weight of the composition.

In some embodiments of any one of the aspects described herein, the remineralization composition can comprise an anti-calculus agent in an amount from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.1% to about 0.9%, from about 0.1% to about 1.0%, from about 0.1% to about 1.1%, from about 0.1% to about 1.2%, from about 0.1% to about 1.3%, from about 0.1% to about 1.4%, from about 0.1% to about 1.5%, from about 0.1% to about 1.6%, from about 0.1% to about 1.7%, from about 0.1% to about 1.8%, from about 0.1% to about 1.9%, from about 0.1% to about 2.0%, from about 0.1% to about 2.1%, from about 0.1% to about 2.2%, from about 0.1% to about 2.3%, from about 0.1% to about 2.4%, from about 0.1% to about 2.5%, from about 0.1% to about 2.6%, from about 0.1% to about 2.7%, from about 0.1% to about 2.8%, from about 0.1% to about 2.9%, from about 0.1% to about 3%, from about 0.1% to about 3.1%, from about 0.1% to about 3.2%, from about 0.1% to about 3.3%, from about 0.1% to about 3.4%, from about 0.1% to about 3.5%, from about 0.1% to about 3.6%, from about 0.1% to about 3.7%, from about 0.1% to about 3.8%, from about 0.1% to about 3.9%, from about 0.1% to about 4%, from about 0.1% to about 4.1%, from about 0.1% to about 4.2%, from about 0.1% to about 4.3%, from about 0.1% to about 4.4%, from about 0.1% to about 4.5%, from about 0.1% to about 4.6%, from about 0.1% to about 4.7%, from about 0.1% to about 4.8%, from about 0.1% to about 4.9%, from about 0.1% to about 5%, from about 0.1% to about 5.1%, from about 0.1% to about 5.2%, from about 0.1% to about 5.3%, from about 0.1% to about 5.4%, from about 0.1% to about 5.5%, from about 0.1% to about 5.6%, from about 0.1% to about 5.7%, from about 0.1% to about 5.8%, from about 0.1% to about 5.9%, from about 0.1% to about 6.0%, from about 0.1% to about 6.1%, from about 0.1% to about 6.2% to about 15%, from about 6.3%, from about 0.1% to about 6.4%, from about 0.1% to about 6.5%, from about 0.1% to about 6.6%, from about 0.1% to about 6.7%, from about 0.1% to about 6.8%, from about 0.1% to about 6.9%, from about 0.1% to about 7%, from about 0.1% to about 7.1%, from about 0.1% to about 7.2%, from about 0.1% to about 7.3%, from about 0.1% to about 7.4%, from about 0.1% to about 7.5%, from about 0.1% to about 7.6%, from about 0.1% to about 7.7%, from about 0.1% to about 7.8%, from about 0.1% to about 7.9%, from about 0.1% to about 8%, from about 0.1% to about 8.1%, from about 0.1% to about 8.2%, from about 0.1% to about 8.3%, from about 0.1% to about 8.4%, from about 0.1% to about 8.5%, from about 0.1% to about 8.6%, from about 0.1% to about 8.7%, from about 0.1% to about 8.8%, from about 0.1% to about 8.9%, from about 0.1% to about 9.0%, from about 0.1% to about 9.1%, from about 0.1% to about 9.2%, from about 0.1% to about 9.3%, from about 0.1% to about 9.4%, from about 0.1% to about 9.5%, from about 0.1% to about 9.6%, from about 0.1% to about 9.7%, from about 0.1% to about 9.8%, from about 0.1% to about 9.9%, from about 0.1% to about 10.0%, from about 0.1% to about 10.1%, from about 0.1% to about 10.2%, from about 0.1% to about 10.3%, from about 0.1% to about 10.4%, from about 0.1% to about 10.5%, from about 0.1% to about 10.6%, from about 0.1% to about 10.7%, from about 0.1% to about 10.8%, from about 0.1% to about 10.9%, from about 0.1% to about 11%, from about 0.1% to about 11.1%, from about 0.1% to about 11.2%, from about 0.1% to about 11.3%, from about 0.1% to about 11.4%, from about 0.1% to about 11.5%, from about 0.1% to about 11.6%, from about 0.1% to about 11.7%, from about 0.1% to about 11.8%, from about 0.1% to about 11.9%, from about 0.1% to about 12%, from about 0.1% to about 12.1%, from about 0.1% to about 12.2%, from about 0.1% to about 12.3%, from about 0.1% to about 12.4%, from about 0.1% to about 12.5%, from about 0.1% to about 12.6%, from about 0.1% to about 12.7%, from about 0.1% to about 12.8%, from about 0.1% to about 12.9%, from about 0.1% to about 13%, from about 0.1% to about 13.1%, from about 0.1% to about 13.2%, from about 0.1% to about 13.3%, from about 0.1% to about 13.4%, from about 0.1% to about 13.5%, from about 0.1% to about 13.6%, from about 0.1% to about 13.7%, from about 0.1% to about 13.8%, from about 0.1% to about 13.9%, from about 0.1% to about 14%, from about 0.1% to about 14.1%, from about 0.1% to about 14.2%, from about 0.1% to about 14.3%, from about 0.1% to about 14.4%, from about 0.1% to about 14.5%, from about 0.1% to about 14.6%, from about 0.1% to about 14.7%, from about 0.1% to about 14.8%, from about 0.1% to about 14.9%, or from about 0.1% to about 15%, by weight of the composition.

The remineralization compositions described herein can comprise a dental abrasive. Dental abrasives are particularly valuable in oral care compositions due to the polishing action of the abrasives during mastication. As used herein, the terms "dental abrasive" and "dental abrasive agent" include all manner and form of such materials which are normally used in toothpastes, chewing gums, and the like. Some exemplary dental abrasives include, but are not limited to, silica, silicon dioxide, aluminium oxide, aluminium hydroxide, sodium aluminosilicate, sodium metaphosphate, magnesium carbonate, calcium carbonate, calcium bicarbonate, calcium phosphate, calcium sulphate, calcium hydrogen phosphate, dicalcium diphosphate dehydrate, tricalcium phosphate, calcium pyrophosphate, or any combination thereof.

The remineralization compositions described herein can comprise a dental abrasive in an amount up to about 50%, by weight of the composition. For example, the remineralization composition can comprise a dental abrasive agent in an amount from about 5% to about 50%, from about 6% to about 50%, from about 7% to about 50%, from about 8% to about 50%, from about 9% to about 50%, from about 10% to about 50%, from about 11% to about 50%, from about 12% to about 50%, from about 13% to about 50%, from about 14% to about 50%, from about 15% to about 50%, from about 16% to about 50%, from about 17% to about 50%, from about 18% to about 50%, from about 19% to about 50%, from about 20% to about 50%, from about 21% to about 50%, from about 22% to about 50%, from about 23% to about 50%, from about 24% to about 50%, from about 25% to about 50%, from about 26% to about 50%, from about 27% to about 50%, from about 28% to about 50%, from about 29% to about 50%, from about 30% to about 50%, from about 31% to about 50%, from about 32% to about 50%, from about 33% to about 50%, from about 34% to about 50%, from about 35% to about 50%, from about 36% to about 50%, from about 37% to about 50%, from about 38% to about 50%, from about 39% to about 50%, from about 40% to about 50%, from about 41% to about 50%, from about 42% to about 50%, from about 43% to about 50%, from about 44% to about 50%, from about 45% to about 50%, from about 46% to about 50%, from about 47% to about 50%, from about 48% to about 50%, or from about 49% to about 50%, by weight of the composition.

In some embodiments of any one of the aspects described herein, the remineralization composition comprises a dental abrasive agent in an amount from about from about 5% to about 6%, from about 5% to about 7%, from about 5% to about 8%, from about 5% to about 9%, from about 5% to about 10%, from about 5% to about 11%, from about 5% to about 12%, from about 5% to about 13%, from about 5% to about 14%, from about 5% to about 15%, from about 5% to about 16%, from about 5% to about 17%, from about 5% to about 18%, from about 5% to about 19%, from about 5% to about 20%, from about 5% to about 21%, from about 5% to about 22%, from about 5% to about 23%, from about 5% to about 24%, from about 5% to about 25%, from about 5% to about 26%, from about 5% to about 27%, from about 5% to about 28%, from about 5% to about 29%, from about 5% to about 30%, from about 5% to about 31%, from about 5% to about 32%, from about 5% to about 33%, from about 5% to about 34%, from about 5% to about 35%, from about 5% to about 36%, from about 5% to about 37%, from about 5% to about 38%, from about 5% to about 39%, from about 5% to about 40%, from about 5% to about 41%, from about 5% to about 42%, from about 5% to about 43%, from about 5% to about 44%, from about 5% to about 45%, from about 5% to about 46%, from about 5% to about 47%, from about 5% to about 48%, from about 5% to about 49%, or from 5% to about 50%, by weight of the composition.

The remineralization compositions described herein can comprise a binder. For example, the remineralization composition described herein can comprise a binder in an amount up to about 10%, by weight of the composition. In some embodiments of any one of the aspects described herein, the remineralization composition comprise a binder in an amount from about 0.1% to about 10%, from about 0.2% to about 10%, from about 0.3% to about 10%, from about 0.4% to about 10%, from about 0.5% to about 10%, from about 0.6% to about 10%, from about 0.7% to about 10%, from about 0.8% to about 10%, from about 0.9% to about 10%, from about 1.0% to about 10%, from about 1.1% to about 10%, from about 1.2% to about 10%, from about 1.3% to about 10%, from about 1.4% to about 10%, from about 1.5% to about 10%, from about 1.6% to about 10%, from about 1.7% to about 10%, from about 1.8% to about 10%, from about 1.9% to about 10%, from about 2.0% to about 10%, from about 2.1% to about 10%, from about 2.2% to about 10%, from about 2.3% to about 10%, from about 2.4% to about 10%, from about 2.5% to about 10%, from about 2.6% to about 10%, from about 2.7% to about 10%, from about 2.8% to about 10%, from about 2.9% to about 10%, to about 3% to about 10%, from about 3.1% to about 10%, from about 3.2% to about 10%, from about 3.3% to about 10%, from about 3.4% to about 10%, from about 3.5% to about 10%, from about 3.6% to about 10%, from about 3.7% to about 10%, from about 3.8% to about 10%, from about 3.9% to about 10%, to about 4% to about 10%, from about 4.1% to about 10%, from about 4.2% to about 10%, from about 4.3% to about 10%, from about 4.4% to about 10%, from about 4.5% to about 10%, from about 4.6% to about 10%, from about 4.7% to about 10%, from about 4.8% to about 10%, from about 4.9% to about 10%, to about 5% to about 10%, from about 5.1% to about 10%, from about 5.2% to about 10%, from about 5.3% to about 10%, from about 5.4% to about 10%, from about 5.5% to about 10%, from about 5.6% to about 10%, from about 5.7% to about 10%, from about 5.8% to about 10%, from about 5.9% to about 10%, from about 6.0% to about 10%, from about 6.1% to about 10%, from about 6.2% to about 10%, from about 6.3% to about 10%, from about 6.4% to about 10%, from about 6.5% to about 10%, from about 6.6% to about 10%, from about 6.7% to about 10%, from about 6.8% to about 10%, from about 6.9% to about 10%, to about 7% to about 10%, from about 7.1% to about 10%, from about 7.2% to about 10%, from about 7.3% to about 10%, from about 7.4% to about 10%, from about 7.5% to about 10%, from about 7.6% to about 10%, from about 7.7% to about 10%, from about 7.8% to about 10%, from about 7.9% to about 10%, to about 8% to about 10%, from about 8.1% to about 10%, from about 8.2% to about 10%, from about 8.3% to about 10%, from about 8.4% to about 10%, from about 8.5% to about 10%, from about 8.6% to about 10%, from about 8.7% to about 10%, from about 8.8% to about 10%, from about 8.9% to about 10%, from about 9.0% to about 10%, from about 9.1% to about 10%, from about 9.2% to about 10%, from about 9.3% to about 10%, from about 9.4% to about 10%, from about 9.5% to about 10%, from about 9.6% to about 10%, from about 9.7% to about 10%, from about 9.8% to about 10%, or from about 9.9% to about 10%, by weight of the composition.

In some embodiments of any one of the aspects described herein, the remineralization composition comprise a binder in an amount from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.1% to about 0.9%, from about 0.1% to about 1.0%, from about 0.1% to about 1.1%, from about 0.1% to about 1.2%, from about 0.1% to about 1.3%, from about 0.1% to about 1.4%, from about 0.1% to about 1.5%, from about 0.1% to about 1.6%, from about 0.1% to about 1.7%, from about 0.1% to about 1.8%, from about 0.1% to about 1.9%, from about 0.1% to about 2.0%, from about 0.1% to about 2.1%, from about 0.1% to about 2.2%, from about 0.1% to about 2.3%, from about 0.1% to about 2.4%, from about 0.1% to about 2.5%, from about 0.1% to about 2.6%, from about 0.1% to about 2.7%, from about 0.1% to about 2.8%, from about 0.1% to about 2.9% to about 10%, to about 3%, from about 0.1% to about 3.1%, from about 0.1% to about 3.2%, from about 0.1% to about 3.3%, from about 0.1% to about 3.4%, from about 0.1% to about 3.5%, from about 0.1% to about 3.6%, from about 0.1% to about 3.7%, from about 0.1% to about 3.8%, from about 0.1% to about 3.9% to about 10%, to about 4%, from about 0.1% to about 4.1%, from about 0.1% to about 4.2%, from about 0.1% to about 4.3%, from about 0.1% to about 4.4%, from about 0.1% to about 4.5%, from about 0.1% to about 4.6%, from about 0.1% to about 4.7%, from about 0.1% to about 4.8%, from about 0.1% to about 4.9% to about 10%, to about 5%, from about 0.1% to about 5.1%, from about 0.1% to about 5.2%, from about 0.1% to about 5.3%, from about 0.1% to about 5.4%, from about 0.1% to about 5.5%, from about 0.1% to about 5.6%, from about 0.1% to about 5.7%, from about 0.1% to about 5.8%, from about 0.1% to about 5.9%, from about 0.1% to about 6.0%, from about 0.1% to about 6.1%, from about 0.1% to about 6.2%, from about 0.1% to about 6.3%, from about 0.1% to about 6.4%, from about 0.1% to about 6.5%, from about 0.1% to about 6.6%, from about 0.1% to about 6.7%, from about 0.1% to about 6.8%, from about 0.1% to about 6.9% to about 10%, to about 7%, from about 0.1% to about 7.1%, from about 0.1% to about 7.2%, from about 0.1% to about 7.3%, from about 0.1% to about 7.4%, from about 0.1% to about 7.5%, from about 0.1% to about 7.6%, from about 0.1% to about 7.7%, from about 0.1% to about 7.8%, from about 0.1% to about 7.9% to about 10%, to about 8%, from about 0.1% to about 8.1%, from about 0.1% to about 8.2%, from about 0.1% to about 8.3%, from about 0.1% to about 8.4%, from about 0.1% to about 8.5%, from about 0.1% to about 8.6%, from about 0.1% to about 8.7%, from about 0.1% to about 8.8%, from about 0.1% to about 8.9%, from about 0.1% to about 9.0%, from about 0.1% to about 9.1%, from about 0.1% to about 9.2%, from about 0.1% to about 9.3%, from about 0.1% to about 9.4%, from about 0.1% to about 9.5%, from about 0.1% to about 9.6%, from about 0.1% to about 9.7%, from about 0.1% to about 9.8%, from about 0.1% to about 9.9%, of from about 0.1% to about 10%, by weight of the composition.

Exemplary binders include, but are not limited to, carboxyvinyl polymers (such as polyacrylic acid crosslinked with polyallyl sucrose or polyallyl pentaerythritol), hydroxyethyl cellulose, hydroxypropyl cellulose, water soluble salts of cellulose ethers (such as sodium carboxymethyl cellulose and sodium carboxymethyl hydroxyethyl cellulose), natural gums (such as carrageenan, karaya gum, guar gum, xanthan gum, gum arabic and tragacanth), finely divided silica, laponite, colloidal magnesium aluminum silicate and mixtures thereof.

In some embodiments of any one of the aspects described herein, the remineralization composition comprise a binder selected from the group consisting of carboxymethyl cellulose, hydroxyethyl cellulose, hydroxypropyl cellulose, carbopol, polyacrylate, sodium polyacrylate, carrageenan, sodium alginate, calcium alginate, sodium calcium alginate, pectin, tragant gum, Arabic gum, guar gum, carrage gum, locust bean gum, gellan gum, tamarind gum, psyllium seed gum, polyvinyl alcohol, sodium chondroitin sulfate, methoxyethylene maleic anhydride copolymer, and any combination thereof.

The remineralization compositions described herein can comprise a coloring agent. For example, the remineralization composition described herein can comprise a coloring agent in an amount up to about 0.75%, by weight of the composition. In some embodiments of any one of the aspects described herein, the remineralization composition comprise a coloring agent in an amount from about 0.01% to about 0.75%, from about 0.02% to about 0.75%, from about 0.03% to about 0.75%, from about 0.04% to about 0.75%, from about 0.05% to about 0.75%, from about 0.06% to about 0.75%, from about 0.07% to about 0.75%, from about 0.08% to about 0.75%, from about 0.09% to about 0.75%, from about 0.10% to about 0.75%, from about 0.11% to about 0.75%, from about 0.12% to about 0.75%, from about 0.13% to about 0.75%, from about 0.14% to about 0.75%, from about 0.15% to about 0.75%, from about 0.16% to about 0.75%, from about 0.17% to about 0.75%, from about 0.18% to about 0.75%, from about 0.19% to about 0.75%, from about 0.20% to about 0.75%, from about 0.21% to about 0.75%, from about 0.22% to about 0.75%, from about 0.23% to about 0.75%, from about 0.24% to about 0.75%, from about 0.25% to about 0.75%, from about 0.26% to about 0.75%, from about 0.27% to about 0.75%, from about 0.28% to about 0.75%, from about 0.29% to about 0.75%, from about 0.30% to about 0.75%, from about 0.31% to about 0.75%, from about 0.32% to about 0.75%, from about 0.33% to about 0.75%, from about 0.34% to about 0.75%, from about 0.35% to about 0.75%, from about 0.36% to about 0.75%, from about 0.37% to about 0.75%, from about 0.38% to about 0.75%, from about 0.39% to about 0.75%, from about 0.40% to about 0.75%, from about 0.41% to about 0.75%, from about 0.42% to about 0.75%, from about 0.43% to about 0.75%, from about 0.44% to about 0.75%, from about 0.45% to about 0.75%, from about 0.46% to about 0.75%, from about 0.47% to about 0.75%, from about 0.48% to about 0.75%, from about 0.49% to about 0.75%, from about 0.50% to about 0.75%, from about 0.51% to about 0.75%, from about 0.52% to about 0.75%, from about 0.53% to about 0.75%, from about 0.54% to about 0.75%, from about 0.55% to about 0.75%, from about 0.56% to about 0.75%, from about 0.57% to about 0.75%, from about 0.58% to about 0.75%, from about 0.59% to about 0.75%, from about 0.60% to about 0.75%, from about 0.61% to about 0.75%, from about 0.62% to about 0.75%, from about 0.63% to about 0.75%, from about 0.64% to about 0.75%, from about 0.65% to about 0.75%, from about 0.66% to about 0.75%, from about 0.67% to about 0.75%, from about 0.68% to about 0.75%, from about 0.69% to about 0.75%, from about 0.70% to about 0.75%, from about 0.71% to about 0.75%, from about 0.72% to about 0.75%, from about 0.73% to about 0.75%, or from about 0.74 to about 0.75%, by weight of the composition.

In some embodiments of any one of the aspects described herein, the remineralization composition comprise a coloring agent in an amount from about 0.01% to about 0.02%, from about 0.01% to about 0.03%, from about 0.01% to about 0.04%, from about 0.01% to about 0.05%, from about 0.01% to about 0.06%, from about 0.01% to about 0.07%, from about 0.01% to about 0.08%, from about 0.01% to about 0.09%, from about 0.01% to about 0.10%, from about 0.01% to about 0.11%, from about 0.01% to about 0.12%, from about 0.01% to about 0.13%, from about 0.01% to about 0.14%, from about 0.01% to about 0.15%, from about 0.01% to about 0.16%, from about 0.01% to about 0.17%, from about 0.01% to about 0.18%, from about 0.01% to about 0.19%, from about 0.01% to about 0.20%, from about 0.01% to about 0.21%, from about 0.01% to about 0.22%, from about 0.01% to about 0.23%, from about 0.01% to about 0.24%, from about 0.01% to about 0.25%, from about 0.01% to about 0.26%, from about 0.01% to about 0.27%, from about 0.01% to about 0.28%, from about 0.01% to about 0.29%, from about 0.01% to about 0.30%, from about 0.01% to about 0.31%, from about 0.01% to about 0.32%, from about 0.01% to about 0.33%, from about 0.01% to about 0.34%, from about 0.01% to about 0.35%, from about 0.01% to about 0.36%, from about 0.01% to about 0.37%, from about 0.01% to about 0.38%, from about 0.01% to about 0.39%, from about 0.01% to about 0.40%, from about 0.01% to about 0.41%, from about 0.01% to about 0.42%, from about 0.01% to about 0.43%, from about 0.01% to about 0.44%, from about 0.01% to about 0.45%, from about 0.01% to about 0.46%, from about 0.01% to about 0.47%, from about 0.01% to about 0.48%, from about 0.01% to about 0.49%, from about 0.01% to about 0.50%, from about 0.01% to about 0.51%, from about 0.01% to about 0.52%, from about 0.01% to about 0.53%, from about 0.01% to about 0.54%, from about 0.01% to about 0.55%, from about 0.01% to about 0.56%, from about 0.01% to about 0.57%, from about 0.01% to about 0.58%, from about 0.01% to about 0.59%, from about 0.01% to about 0.60%, from about 0.01% to about 0.61%, from about 0.01% to about 0.62%, from about 0.01% to about 0.63%, from about 0.01% to about 0.64%, from about 0.01% to about 0.65%, from about 0.01% to about 0.66%, from about 0.01% to about 0.67%, from about 0.01% to about 0.68%, from about 0.01% to about 0.69%, from about 0.01% to about 0.70%, from about 0.01% to about 0.71%, from about 0.01% to about 0.72%, from about 0.01% to about 0.73% to about 0.75%, from about 0.01% to about 0.74%, or from about 0.01% to about 0.75%, by weight of the composition.

Exemplary coloring agents include, but are not limited to, red, blue and green food coloring (such as FD and C-type dyes and lakes, for example D&C blue #1, D&C blue #4, D&C brown #1, D&C green #5 through #8, D&C orange #4 through #11, D&C yellow #2 through #11, D&C red #6 through #40, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3); carmine, fruit and vegetable extracts, and any combination thereof.

The remineralization compositions described herein can also comprise a preservative. Some exemplary preservatives amenable to the remineralization compositions described herein include, but are not limited to benzalkonium chloride, benzethonium chloride, benzoic acid, sodium benzoate, p-hydroxybenzoic acid, methyl p-hydroxybenzoate, benzyl alcohol, bronopol, cetrimide, cetylpyridinium chloride, chlorhexidine, chlorobutanol, chlorocresol, chlorocylenol, ethanol, glycerin, hexetidine, imidourea, phenol, phenoxyethanol, phenylethyl alcohol, phenyl mercuric nitrate, propylene glycol, sodium propionate, thimerosyl, methyl paraben, ethyl paraben, butyl paraben, isobutyl paraben, benzyl paraben, citric acid, trisodium citrate, sorbic acid, dichlorinated phenol, phumeotassium sorbate, or any combination thereof.

The preservative can be present in the remineralization composition in an amount up to about 3%, by weight of the composition. In some embodiments of any one of the aspects described herein, the remineralization composition comprises a preservative in an amount from about 0.1% to about 3%, from about 0.2% to about 3%, from about 0.3% to about 3%, from about 0.4% to about 3%, from about 0.5% to about 3%, from about 0.6% to about 3%, from about 0.7% to about 3%, from about 0.8% to about 3%, from about 0.9% to about 3%, from about 1% to about 3%, from about 1.1% to about 3%, from about 1.2% to about 3%, from about 1.3% to about 3%, from about 1.4% to about 3%, from about 1.5% to about 3%, from about 1.6% to about 3%, from about 1.7% to about 3%, from about 1.8% to about 3%, from about 1.9% to about 3%, from about 2% to about 3%, from about 2.1% to about 3%, from about 2.2% to about 3%, from about 2.3% to about 3%, from about 2.4% to about 3%, from about 2.5% to about 3%, from about 2.6% to about 3%, from about 2.7% to about 3%, from about 2.8% to about 3%, or from about 2.9% to about 3%, by weight of the composition.

In some embodiments of any one of the aspects described herein, the remineralization composition comprises a preservative in an amount from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.1% to about 0.9%, from about 0.1% to about 1.0%, from about 0.1% to about 1.1%, from about 0.1% to about 1.2%, from about 0.1% to about 1.3%, from about 0.1% to about 1.4%, from about 0.1% to about 1.5%, from about 0.1% to about 1.6%, from about 0.1% to about 1.7%, from about 0.1% to about 1.8%, from about 0.1% to about 1.9%, from about 0.1% to about 2.0%, from about 0.1% to about 2.1%, from about 0.1% to about 2.2%, from about 0.1% to about 2.3%, from about 0.1% to about 2.4%, from about 0.1% to about 2.5%, from about 0.1% to about 2.6%, from about 0.1% to about 2.7%, from about 0.1% to about 2.8%, or from about 0.1% to about 2.9%, by weight of the composition.

The remineralization compositions described herein can also comprise a humectant. Some exemplary humectants amenable to the remineralization compositions described herein include, but are not limited to, glycerol, sorbitol, propylene glycol, glycerin, 1,3-butylene glycol, 1,2-hexanediol, 1,2-octanediol, low molecular weight polyethylene glycols, and any combination thereof. The humectant can be present in the remineralization composition in an amount up to about 50%, by weight of the composition.

In some embodiments of any one of the aspects described herein, the remineralization composition comprises a humectant in an amount from about 1% to about 50%, from about 2% to about 50%, from about 3% to about 50%, from about 4% to about 50%, from about 5% to about 50%, from about 6% to about 50%, from about 7% to about 50%, from about 8% to about 50%, from about 9% to about 50%, from about 10% to about 50%, from about 11% to about 50%, from about 12% to about 50%, from about 13% to about 50%, from about 14% to about 50%, from about 15% to about 50%, from about 16% to about 50%, from about 17% to about 50%, from about 18% to about 50%, from about 19% to about 50%, from about 20% to about 50%, from about 21% to about 50%, from about 22% to about 50%, from about 23% to about 50%, from about 24% to about 50%, from about 25% to about 50%, from about 26% to about 50%, from about 27% to about 50%, from about 28% to about 50%, from about 29% to about 50%, from about 30% to about 50%, from about 31% to about 50%, from about 32% to about 50%, from about 33% to about 50%, from about 34% to about 50%, from about 35% to about 50%, from about 36% to about 50%, from about 37% to about 50%, from about 38% to about 50%, from about 39% to about 50%, from about 40% to about 50%, from about 41% to about 50%, from about 42% to about 50%, from about 43% to about 50%, from about 44% to about 50%, from about 45% to about 50%, from about 46% to about 50%, from about 47% to about 50%, from about 48% to about 50%, or from about 49% to about 50%, by weight of the composition.

In some embodiments of any one of the aspects described herein, the remineralization composition comprises a humectant in an amount from about 1% to about 2%, from about 1% to about 3%, from about 1% to about 4%, from about 1% to about 5%, from about 1% to about 6%, from about 1% to about 7%, from about 1% to about 8%, from about 1% to about 9% to about 50%, from about 10%, from about 1% to about 11%, from about 1% to about 12%, from about 1% to about 13%, from about 1% to about 14%, from about 1% to about 15%, from about 1% to about 16%, from about 1% to about 17%, from about 1% to about 18%, from about 1% to about 19%, from about 1% to about 20%, from about 1% to about 21%, from about 1% to about 22%, from about 1% to about 23%, from about 1% to about 24%, from about 1% to about 25%, from about 1% to about 26%, from about 1% to about 27%, from about 1% to about 28%, from about 1% to about 29%, from about 1% to about 30%, from about 1% to about 31%, from about 1% to about 32%, from about 1% to about 33%, from about 1% to about 34%, from about 1% to about 35%, from about 1% to about 36%, from about 1% to about 37%, from about 1% to about 38%, from about 1% to about 39%, from about 1% to about 40%, from about 1% to about 41%, from about 1% to about 42%, from about 1% to about 43%, from about 1% to about 44%, from about 1% to about 45%, from about 1% to about 46%, from about 1% to about 47%, from about 1% to about 48%, from about 1% to about 49%, or from about 1% to about 50%, by weight of the composition.

The remineralization composition can be formulated into any desire form. For example, the remineralization composition can be formulated as a solution, gel, suspension, slurry, paste, spray, paint, ready-to-dissolve packet of powdered salt, varnish, sealant or cement.

In some embodiments of any one of the aspects described herein, the remineralization composition is formulated as an oral care composition. As used herein, an "oral care composition" refers to any composition which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. Exemplary oral care compositions include, but are not limited to, toothpastes, mouthrinses, dentifrices, chewing gums and lozenges, strips (strips) and gels.

In some embodiments of any one of the aspects described herein, the oral care composition is a dentifrice. The term "dentifrice" generally refers to formulations used to clean oral surfaces. Dentifrices are oral compositions that are not intentionally swallowed for purposes of systemic administration of therapeutic agents, but are applied to the oral cavity for treatment and then expectoration. Typically, the dentifrice is used with a cleaning implement, such as a toothbrush, which is typically applied to the bristles of the toothbrush and then brushed against the accessible surfaces of the oral cavity. Preferably, the dentifrice is in the form of a paste or gel (or combination thereof). In some embodiments, the oral care composition is a toothpaste. In some other embodiments, the oral care composition is a mouthwash.

In some embodiments of any one of the aspects described herein, the remineralization composition can be included in a delivery device. For example, the remineralization composition can be included in a night guard, customer tray, or sticky stripe. In some embodiments of any one of the aspects described herein, the remineralization composition can be used as microencapsulate with a micro-pump.

The remineralization compositions described herein are useful for remineralization damaged dental surfaces. Accordingly, in another aspect, provided herein is a method for remineralizing a damaged dental surface. Generally, the method comprising applying an effective amount of a remineralization composition described herein to the damaged dental surface.

As used herein, a "damaged dental surface" refers to any weakening or damage found in the enamel. This weakening or damage can be found in either primary or permanent teeth. This weakening or damage can be due to either genetic or environmental factors, including but not limited to tooth decay, decalcification, tooth fracture, corrosion due to sugar and/or acidic exposure, bleaching, abrasion, pressure, dry mouth, oral piercings, buildup of plaque, yellowing of the tooth, tooth sensitivity, tooth cracks, tooth breaks, tooth fractures, osteoporosis, osteopenia, exposure to chemotherapy, loss of calcium, periodontal disease, poor dentures or bridgework, external injuries (e.g. impact to face or jaw), tooth misalignment, osteomyelitis, face tumors, birth defects, and bone loss due to the immune system. In some embodiments of any one of the aspects described herein, the damaged dental comprises demineralization, decay, abrasion, and/or superficial to moderate fractures.

The remineralization compositions described herein can also be used for dentin tube occlusion and sealing, tooth desensitization, root canal sealing, enamel hardening, and fissure filling. Accordingly, in another aspect, provided herein is a method for dentin tube occlusion and sealing, tooth desensitization, root canal sealing, enamel hardening, or fissure filling. The method comprises applying an effective amount of a remineralization composition described herein to a tooth in need thereof.

The remineralization compositions and methods described herein are also useful for treating a disease of the teeth, e.g., Non-Cavitated Caries Lesions disease.

Use of the composition in the context of the present disclosure typically involves applying the composition to the oral cavity for a recommended period of time prior to expectoration. With regard to the length of time of exposure to the teeth of the remineralization composition applied to, it is necessary that the period of time be great enough to allow diffusion of the ions into the damaged or demineralized subsurface. For example, at least about ten seconds are required for the remineralization diffusion. Accordingly, the remineralization composition can be contacted with or applied to the teeth for a period of at least about 10 seconds, at least about 15 seconds, at least about 20 seconds, at least about 25 seconds, at least about 30 seconds, at least about 35 seconds, at least about 40 seconds, at least about 45 seconds, at least about 50 seconds, at least about 55 seconds, at least about 60 seconds, at least about 65 seconds, at least about 70 seconds, at least about 75 seconds, at least about 80 seconds, at least about 85 seconds, at least about 90 seconds, at least about 95 seconds, at least about 100 seconds, at least about 105 seconds, at least about 110 seconds, at least about 115 seconds, at least about 2 minutes, at least 2.5 minutes, at least about 5 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours or more. In some embodiment of any one of the aspects described herein, the remineralization composition can be contacted with or applied to the teeth for a period of about 10 seconds to about 15 minutes. In some preferred embodiments, the remineralization composition can be contacted with or applied to the teeth for a period of between 16 hours to 144 hours, between 16 hours to 143 hours, between 16 hours to 142 hours, between 16 hours to 141 hours, between 16 hours to 140 hours, between 16 hours to 139 hours, between 16 hours to 138 hours, between 16 hours to 137 hours, between 16 hours to 136 hours, between 16 hours to 135 hours, between 16 hours to 134 hours, between 16 hours to 133 hours, between 16 hours to 132 hours, between 16 hours to 131 hours, between 16 hours to 130 hours, between 16 hours to 129 hours, between 16 hours to 128 hours, between 16 hours to 127 hours, between 16 hours to 126 hours, between 16 hours to 126 hours, between 16 hours to 125 hours, between 16 hours to 124 hours, between 16 hours to 123 hours, between 16 hours to 122 hours, between 16 hours to 121 hours, between 16 hours to 120 hours, between 16 hours to 119 hours, between 16 hours to 118 hours, between 16 hours to 117 hours, between 16 hours to 116 hours, between 16 hours to 115 hours, between 16 hours to 114 hours, between 16 hours to 113 hours, between 16 hours to 112 hours, between 16 hours to 111 hours, between 16 hours to 110 hours, between 16 hours to 109 hours, between 16 hours to 108 hours, between 16 hours to 107 hours, between 16 hours to 106 hours, between 16 hours to 105 hours, between 16 hours to 104 hours, between 16 hours to 103 hours, between 16 hours to 102 hours, between 16 hours to 101 hours, between 16 hours to 100 hours, between 16 hours to 99 hours, between 16 hours to 98 hours, between 16 hours to 97 hours, between 16 hours to 96 hours, between 16 hours to 95 hours, between 16 hours to 94 hours, between 16 hours to 93 hours, between 16 hours to 92 hours, between 16 hours to 91 hours, between 16 hours to 90 hours, between 16 hours to 89 hours, between 16 hours to 88 hours, between 16 hours to 87 hours, between 16 hours to 86 hours, between 16 hours to 85 hours, between 16 hours to 84 hours, between 16 hours to 83 hours, between 16 hours to 82 hours, between 16 hours to 81 hours, between 16 hours to 80 hours, between 16 hours to 79 hours, between 16 hours to 78 hours, between 16 hours to 77 hours, between 16 hours to 76 hours, between 16 hours to 75 hours, between 16 hours to 74 hours, between 16 hours to 73 hours, between 16 hours to 72 hours, between 16 hours to 71 hours, between 16 hours to 70 hours, between 16 hours to 69 hours, between 16 hours to 68 hours, between 16 hours to 67 hours, between 16 hours to 66 hours, between 16 hours to 65 hours, between 16 hours to 64 hours, between 16 hours to 63 hours, between 16 hours to 62 hours, between 16 hours to 61 hours, between 16 hours to 60 hours, between 16 hours and 59 hours, between 16 hours to 58 hours, between 16 hours to 57 hours, between 16 hours to 56 hours, between 16 hours to 55 hours, between 16 hours to 54 hours, between 16 hours to 53 hours, between 16 hours to 52 hours, between 16 hours to 51 hours, between 16 hours to 50 hours, between 16 hours to 49 hours, between 16 hours to 48 hours, between 16 hours to 47 hours, between 16 hours to 46 hours, between 16 hours to 45 hours, between 16 hours to 44 hours, between 16 hours to 43 hours, between 16 hours to 42 hours, between 16 hours to 41 hours, between 16 hours to 40 hours, between 16 hours to 39 hours, between 16 hours to 38 hours, between 16 hours to 37 hours, between 16 hours to 36 hours, between 16 hours to 35 hours, between 16 hours to 34 hours, between 16 hours to 33 hours, between 16 hours to 32 hours, between 16 hours to 31 hours, between 16 hours to 30 hours, between 16 hours to 29 hours, between 16 hours to 28 hours, between 16 hours to 27 hours, between 16 hours to 26 hours, between 16 hours to 25 hours, between 16 hours to 24 hours, between 16 hours to 23 hours, between 16 hours to 22 hours, between 16 hours to 21 hours, between 16 hours to 20 hours, between 16 hours to 19 hours, between 16 hours to 18 hours, between 16 hours to 17 hours.

Without wishing to be bound by a theory, the synthetic enamel formed using the remineralization compositions and methods described herein has the same mineral density, chemical composition, crystal phases, hierarchical structure and hardness as the natural enamel.

In some embodiments, the synthetic enamel can be grown in the presence of bacteria using the methods as described herein. The synthetic enamel can contain bacteria embedded in the synthetic enamel after the remineralization process. The bacteria can be both beneficial and harmful to the host (i.e., human). Exemplary bacterial genera and/or bacterial species include, but are not limited to *Escherichia coli, Enterococcus faecalis, Actinomyces, Bacteroides, Bifidobacterium, Eubacterium, Fusobacterium, Lactobacillus, Leptotrichia, Peptococcus, Peptostreptococcus, Propionibacterium, Selenomonas, Treponema, Veillonella*, and *Propionibacterium propionicus*. In some preferred embodiments, the synthetic enamel can be grown in the presence of *Escherichia coli* and/or *Enterococcus faecalis*.

In some embodiments, the synthetic enamel can be grown in the presence of a dentin desensitizer. As used herein, a dentin desensitizer is a composition that can cause a reduction in dentin permeability and/or suppress the stimulation of intradental nerve fibers that cause pain. Exemplary dentin desensitizers include, but are not limited to compositions containing glutaraldehyde, oxalate salts, calcium phosphates, fluoride, or light-cured resins. In some preferred embodiments, the synthetic enamel can be grown in the presence of GLUMA™, a dentin desensitizer with 5% glutaraldehyde and 35% hydroxy-ethyl methacrylate in water.

In some embodiments, the synthetic enamel can be grown in the presence of an antiseptic. As used herein, an antiseptic is a composition that is applied to living tissue to destroy or inhibit the growth of bacteria and other microorganisms. Exemplary antiseptics include, but are not limited to alcohols (i.e., ethyl alcohol and isopropyl alcohol), quaternary ammonium compounds (i.e., benzlonium chloride, centrimide, methylbenzethonium chloride, cetalkonium chloride, cetylpyridinium chloride, dofanium chloride, demiphen bromide), chlorhexidine and other diguanides (i.e., chlorhexidine gluconate, chlorhexidine acetate), antibacterial dyes (i.e., Proflavine hemisulphate, Triphenylmethane, brilliant green, crystal violet, gentian violet), chlorine and hypochlorites (i.e., sodium hypochlorite), iodine compounds (i.e., povidone), peroxide and permanganates (i.e., hydrogen peroxide solution, potassium permanganate solution, benzoyl peroxide), halogenated phenol derivatives (i.e., chlorocresol, chloroxylenol, chlorophene, hexachlorophene/hexachlorophene, triclosan), or quinolone deriviatives (hydroxyquinoline sulphate, potassium hydroxyquinoline sulphate, chlorquinaldol, dequalinium chloride, diiodohydroxyquinoline). In some preferred embodiments, the synthetic enamel can be grown in the presence of cetylpyridinium chloride (CPC).

The Vickers hardness test can be used to measure the hardness of the enamel. The required calculations are independent of the size of the indenter, and the indenter can be used for all materials, irrespective of hardness. The unit of hardness given by the test is known as the Vickers Pyramid Number (HV) or Diamond Pyramid Hardness (DPH). The hardness number is determined by the load over the surface area of the indentation.

In some embodiments of any one of the aspects described herein, the Vickers hardness of polished enamel formed using the composition and/or methods described herein can be at least 200 kg/mm$^2$, at least 210 kg/mm$^2$, at least 220 kg/mm$^2$, at least 230 kg/mm$^2$, at least 240 kg/mm$^2$, at least 250 kg/mm$^2$, at least 260 kg/mm$^2$, at least 270 kg/mm$^2$, at least 280 kg/mm$^2$, at least 290 kg/mm$^2$, at least 300 kg/mm$^2$, at least 310 kg/mm$^2$, at least 320 kg/mm$^2$, at least 330 kg/mm$^2$, at least 340 kg/mm$^2$, at least 350 kg/mm$^2$, at least 360 kg/mm$^2$, at least 370 kg/mm$^2$, at least 380 kg/mm$^2$, at least 390 kg/mm$^2$, at least 400 kg/mm$^2$, at least 410 kg/mm$^2$, at least 420 kg/mm$^2$, at least 430 kg/mm$^2$, at least 440 kg/mm$^2$, at least 450 kg/mm$^2$, at least 460 kg/mm$^2$, at least 470 kg/mm$^2$, at least 480 kg/mm$^2$, at least 490 kg/mm$^2$, at least 500 kg/mm$^2$, at least 510 kg/mm$^2$, at least 520 kg/mm$^2$, at least 530 kg/mm$^2$ or more. In some preferred embodiments, the preferred Vickers hardness of a cross-section enamel formed using the compositions and/or methods described herein can be up to 302 kg/mm$^2$.

In some embodiments of any one of the aspects described herein, the Vickers hardness of a cross-section enamel formed using the composition and/or methods described herein can be at least can be at least at least 200 kg/mm$^2$, at least 210 kg/mm$^2$, at least 220 kg/mm$^2$, at least 230 kg/mm$^2$, at least 240 kg/mm$^2$, at least 250 kg/mm$^2$, at least 260 kg/mm$^2$, at least 270 kg/mm$^2$, at least 280 kg/mm$^2$, at least 290 kg/mm$^2$, at least 300 kg/mm$^2$, at least 310 kg/mm$^2$, at least 320 kg/mm$^2$, at least 330 kg/mm$^2$, at least 340 kg/mm$^2$, at least 350 kg/mm$^2$, at least 360 kg/mm$^2$, at least 370 kg/mm$^2$, at least 380 kg/mm$^2$, at least 390 kg/mm$^2$, at least 400 kg/mm$^2$, at least 410 kg/mm$^2$, at least 420 kg/mm$^2$, at least 430 kg/mm$^2$, at least 440 kg/mm$^2$, at least 450 kg/mm$^2$, at least 460 kg/mm$^2$, at least 470 kg/mm$^2$, at least 480 kg/mm$^2$, at least 490 kg/mm$^2$, at least 500 kg/mm$^2$, at least 510 kg/mm$^2$, at least 520 kg/mm$^2$, at least 530 kg/mm$^2$ or more. In some preferred embodiments, the preferred Vickers hardness of a cross-section enamel formed using the compositions and/or methods described herein can be up to 302 kg/mm$^2$.

In some embodiments of any one of the aspects described herein, the Vickers hardness of a top-surface of continuous grown enamel layer formed using the composition and/or methods described herein can be at least 135 kg/mm$^2$, at least 135.5 kg/mm$^2$, at least 136 kg/mm$^2$, at least 136.5 kg/mm$^2$, at least 137 kg/mm$^2$, at least 137.5 kg/mm$^2$, at least 138 kg/mm$^2$, at least 138.5 kg/mm$^2$, at least 139 kg/mm$^2$, at least 139.5 kg/mm$^2$, at least 140 kg/mm$^2$, at least 140.5 kg/mm$^2$, at least 141 kg/mm$^2$, at least 141.5 kg/mm$^2$, at least 142 kg/mm$^2$, at least 142.5 kg/mm$^2$, at least 143 kg/mm$^2$, at least 143.5 kg/mm$^2$, at least 144 kg/mm$^2$, at least 144.5 kg/mm$^2$, at least 145 kg/mm$^2$, at least 145.5 kg/mm$^2$, at least 146 kg/mm$^2$, at least 146.5 kg/mm$^2$, at least 147 kg/mm$^2$, at least 147.5 kg/mm$^2$, at least 148 kg/mm$^2$, at least 148.5 kg/mm$^2$, at least 149 kg/mm$^2$, at least 149.5 kg/mm$^2$, at least 150 kg/mm$^2$, at least 150.5 kg/mm$^2$, at least 151 kg/mm$^2$, at least 151.5 kg/mm$^2$, at least 152 kg/mm$^2$, at least 152.5 kg/mm$^2$, at least 153 kg/mm$^2$, at least 153.5 kg/mm$^2$, at least 154 kg/mm$^2$, at least 154.5 kg/mm$^2$, at least 155 kg/mm$^2$, at least 155.5 kg/mm$^2$, at least 156 kg/mm$^2$, at least 156.5 kg/mm$^2$, at least 157 kg/mm$^2$, at least 157.5 kg/mm$^2$, at least 158 kg/mm$^2$, at least 158.5 kg/mm$^2$, at least 159 kg/mm$^2$, at least 159.5 kg/mm$^2$, at least 160 kg/mm$^2$, at least 160.5 kg/mm$^2$, at least 161 kg/mm$^2$, at least 161.5 kg/mm$^2$, at least 162 kg/mm$^2$, at least 162.5 kg/mm$^2$, at least 163 kg/mm$^2$, at least 163.5 kg/mm$^2$, at least 164 kg/mm$^2$, at least 164.5 kg/mm$^2$, at least 165 kg/mm$^2$, at least 165.5 kg/mm$^2$, at least 166 kg/mm$^2$, at least 166.5 kg/mm$^2$, at least 167 kg/mm$^2$, at least 167.5 kg/mm$^2$, at least 168 kg/mm$^2$, at least 168.5 kg/mm$^2$, at least 169 kg/mm$^2$, at least 169.5 kg/mm$^2$, at least 170 kg/mm$^2$, at least 170.5 kg/mm$^2$, at least 171 kg/mm$^2$, at least 171.5 kg/mm$^2$, at least 172 kg/mm$^2$, at least 172.5 kg/mm$^2$, at least 173 kg/mm$^2$, at least 173.5 kg/mm$^2$, at least 174 kg/mm$^2$, at least 174.5 kg/mm$^2$, at least 175 kg/mm$^2$, at least 175.5 kg/mm$^2$, at least 176 kg/mm$^2$, at least 176.5 kg/mm$^2$, at least 177 kg/mm$^2$, at least 177.5 kg/mm$^2$, at least 178 kg/mm$^2$, at least 178.5 kg/mm$^2$, at least 179 kg/mm$^2$, at least 179.5 kg/mm$^2$, at least 180 kg/mm$^2$, at least 180.5 kg/mm$^2$, at least 181 kg/mm$^2$, at least 181.5 kg/mm$^2$, at least 182 kg/mm$^2$, at least 182.5 kg/mm$^2$, at least 183 kg/mm$^2$, at least 183.5 kg/mm$^2$, at least 184 kg/mm$^2$, at least 184.5 kg/mm$^2$, at least 185 kg/mm$^2$, at least 185.5 kg/mm$^2$, at least 186 kg/mm$^2$, at least 186.5 kg/mm$^2$, at least 187 kg/mm$^2$, at least 187.5 kg/mm$^2$, at least 188 kg/mm$^2$, at least 189 kg/mm$^2$, at least 189.5 kg/mm$^2$, at least 190 kg/mm$^2$, at least 190.5 kg/mm$^2$, at least 191 kg/mm$^2$, at least 191.5 kg/mm$^2$, at least 192 kg/mm$^2$, at least 192.5 kg/mm$^2$, at least 193 kg/mm$^2$, at least 193.5 kg/mm$^2$, at least 194 kg/mm$^2$, at least 194.5 kg/mm$^2$, at least 195 kg/mm$^2$, at least 195.5 kg/mm$^2$, at least 196 kg/mm$^2$, at least 196.5 kg/mm$^2$, at least 197 kg/mm$^2$, at least 197.5 kg/mm$^2$, at least 198 kg/mm$^2$, at least 198.5 kg/mm$^2$, at least 199 kg/mm$^2$, at least 199.5 kg/mm$^2$, at least 200 kg/mm$^2$, at least 200.5 kg/mm$^2$, at least 201 kg/mm$^2$, at least 201.5 kg/mm$^2$, at least 202 kg/mm$^2$, at least 202.5 kg/mm$^2$, at least 203 kg/mm$^2$, at least 203.5 kg/mm$^2$, at least 204 kg/mm$^2$, at least 204.5 kg/mm$^2$, at least 205 kg/mm$^2$, at least 205.5 kg/mm$^2$, at least 206 kg/mm$^2$, at least 206.5 kg/mm$^2$, at least 207 kg/mm$^2$, at least 207.5 kg/mm$^2$, at least 208 kg/mm$^2$, at least 208.5 kg/mm$^2$, at least 209 kg/mm$^2$, at least 209.5 kg/mm$^2$, at least 210 kg/mm$^2$, at least 210.5 kg/mm$^2$, at least 211 kg/mm$^2$, at least 211.5 kg/mm$^2$, at least 212 kg/mm$^2$, at least 212.5 kg/mm$^2$, at least 213 kg/mm$^2$, at least 213.5 kg/mm$^2$, at least 214 kg/mm$^2$, at least 214.5 kg/mm$^2$, at least 215 kg/mm$^2$, at least 215.5 kg/mm$^2$, at least 216 kg/mm$^2$, at least 216.5 kg/mm$^2$, at least 217 kg/mm$^2$, at least 217.5 kg/mm$^2$, at least 218 kg/mm$^2$, at least 218.5 kg/mm$^2$, at least 219 kg/mm$^2$, at least 219.5 kg/mm$^2$, at least 220 kg/mm$^2$, at least 220.5 kg/mm$^2$, at least 221 kg/mm$^2$, at least 221.5 kg/mm$^2$, at least 222 kg/mm$^2$, at least 222.5 kg/mm$^2$, at least 223 kg/mm$^2$, at least 223.5 kg/mm$^2$, at least 224 kg/mm$^2$, at least 224.5 kg/mm$^2$, at least 225 kg/mm$^2$, at least 225.5 kg/mm$^2$, at least 226 kg/mm$^2$, at least 226.5 kg/mm$^2$, at least 227 kg/mm$^2$, at least 227.5 kg/mm$^2$, at least 228 kg/mm$^2$, at least 228.5 kg/mm$^2$, at least 229 kg/mm$^2$, at least 229.5 kg/mm$^2$, at least 230 kg/mm$^2$, at least 230.5 kg/mm$^2$, at least 231 kg/mm$^2$, at least 231.5 kg/mm$^2$, at least 232 kg/mm$^2$, at least 232.5 kg/mm$^2$, at least 233 kg/mm$^2$ or more. In some preferred embodiments, the preferred Vickers hardness of a cross-section enamel formed using the compositions and/or methods described herein can be up to 302 kg/mm$^2$.

In some embodiments of any one of the aspects described herein, the Vickers hardness of synthetic enamel formed using the composition and/or methods described herein can be between 2.0 GPa and 4.0 GPa, between 2.0 GPa and 3.9 GPa, between 2.0 GPa and 3.8 GPa, between 2.0 GPa and 3.7 GPa, between 2.0 GPa and 3.6 GPa, between 2.0 GPa and 3.5 GPa, between 2.0 GPa and 3.4 GPa, between 2.0 GPa and 3.3 GPa, between 2.0 GPa and 3.2 GPa, between 2.0 GPa and 3.1 GPa, between 2.0 GPa and 3.0 GPa, between 2.0 GPa and 2.9 GPa, between 2.0 GPa and 2.8 GPa, between 2.0 GPa and 2.7 GPa, between 2.0 GPa and 2.6 GPa, between 2.0 GPa and 2.5 GPa, between 2.0 GPa and 2.4 GPa, between 2.0 GPa and 2.3 GPa, between 2.0 GPa and 2.2 GPa, between 2.1 GPa and 4.0 GPa, between 2.2 GPa and 4.0 GPa, between 2.3 GPa and 4.0 GPa, between 2.4 GPa and 4.0 GPa, between 2.5 GPa and 4.0 GPa, between 2.6 GPa and 4.0 GPa, between 2.7 GPa and 4.0 GPa, between 2.8 GPa and 4.0 GPa, between 2.9 GPa and 4.0 GPa, between 3.0 GPa and 4.0 GPa, between 3.1 GPa and 4.0 GPa, between 3.2 GPa and 4.0 GPa, between 3.3 GPa and 4.0 GPa, between 3.4 GPa and 4.0 GPa, between 3.5 GPa and 4.0 GPa, between 3.6 GPa and 4.0 GPa, between 3.7 GPa and 4.0 GPa, between 3.8 GPa and 4.0 GPa, between 3.9 GPa and 4.0 GPa, between 2.5 GPa and 3.5 GPa, between 2.2 GPa and 3.2 GPa, between 2.8 GPa and 3.8 GPa, between 3.0 GPa and 3.5 GPa, between 2.5 GPa and 3.0 GPa.

Some Selected Definitions

Unless otherwise defined herein, scientific, and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20$^{th}$ Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149x); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338x, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

Other than in the operating examples, or where otherwise indicated, all numbers expressing quantities of ingredients or reaction conditions used herein should be understood as modified in all instances by the term "about." The term "about" when used in connection with percentages can mean±1%. In some embodiments of the various aspects described herein, the term "about" when used in connection with percentages can mean±5%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) or greater difference.

In some embodiments of any one of the aspects described herein, the remineralization composition has anti-carries activity. The term "anti-caries" refers to any compound or substance that is able to prevent, reduce, or eliminate caries, or cavities, from human teeth. A compound, substance or composition that has anti-caries activity can have a reduction of caries from human teeth that is at least a 5% reduction, at least a 10% reduction, at least a 15% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, at least a 99% reduction, or more.

The phrase "effective amount" as used herein means that amount of a remineralization composition which is effective to achieve a desired result, e.g., growth of enamel. As used herein, the term "subject" refers to any living organism which can be administered compound and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult, child and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc.

In some embodiments, the subject is a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of a fibrotic disease or disorder.

It is noted that a human subject can be of any age, gender, race or ethnic group, e.g., Caucasian (white), Asian, African, black, African American, African European, Hispanic, Middle eastern, etc.

In addition, the methods described herein can be used to treat domesticated animals and/or pets. A subject can be male or female. A subject can be one who has been previously diagnosed with or identified as suffering from or having a disease or disorder needing treatment, but need not have already undergone treatment. For example, the subject can be one who has been previously diagnosed with or identified as suffering from or having a microbial infection, e.g., a fungal infection.

In some embodiments of any one of the aspects, the subject is human.

Aspects of the present technology can be defined in any of the following numbered embodiments:

Embodiment 1: A remineralization composition comprising: a) calcium in a concentration from about 0.1 mM to about 500 mM; b) phosphate in a concentration from about 0.1 mM to about 100 mM; c) fluoride in a concentration from about 0.2 ppm to about 300 ppm; d) strontium in a concentration from about 0.05 ppm to about 100 ppm, wherein the composition has a pH of from about 6 to about 8.

Embodiment 2: The remineralization composition of Embodiment 1, wherein the composition further comprises magnesium, stannous and/or zinc, optionally in a concentration from about 1 ppm to about 50 ppm.

Embodiment 3: The remineralization composition of Embodiment 2, wherein the magnesium is in form of a salt selected from the group consisting of magnesium chloride, magnesium acetate, magnesium benzoate, magnesium citrate, magnesium formate, magnesium hexafluorosilicate, magnesium hydroxide, magnesium lactate, magnesium molybdate, magnesium nitrate, magnesium perchlorate, magnesium phosphonate, magnesium salicylate, magnesium sulfate, magnesium sulfite, and any combination thereof; or stannous is in form of a salt selected from the group consisting of tin fluoride, tin chloride, tin bromide, tin iodide, tin cyanide and tin isothiocyanide, tin nitrate, tin sulfate, tin phosphate, and any combination thereof; or zinc is in form of a salt selected from the group consisting of zinc oxide, zinc acetate, zinc borate, zinc nitrate, zinc sulfate, zinc chloride, zinc chlorate, zinc bromide, zinc nitrate, zinc hydrophosphite, zinc oxalate, zinc oleate, zinc peroxide, zinc citrate, zinc gluconate, zinc malate, zinc tartrate, zinc carbonate, zinc phosphate, zinc molybdate, zinc chromate, zinc arsenite, zinc arsenate octahydrate), zinc bromide dehydrate, zinc citrate dihydrate, zinc cyanide, zinc fluoride, zinc hexafluorosilicate, zinc iodide, zinc methacrylate, zinc nitrate hydrate, zinc oxalate hydrate, zinc perchlorate hexahydrate, zinc selenite, zinc sulfate heptahydrate, zinc tetrafluoroborate hydrate, zinc p-toluenesulfonate hydrate, and any combination thereof.

Embodiment 4: The remineralization composition of any one of Embodiments 1-3, wherein the composition is supersaturated.

Embodiment 5: The remineralization composition of any one of Embodiments 1-4, wherein the composition exhibits synergistic remineralization activity.

Embodiment 6: The remineralization composition of any one of Embodiments 1-4, wherein the calcium is in form of a salt selected from the group consisting of calcium chloride, calcium acetate, calcium bromide, calcium fluoride, calcium iodide, calcium gluconate, calcium sulfate, calcium phosphate, calcium glycerophosphate, calcium borate, calcium carbonate, calcium oxalate, calcium citrate, calcium formate, calcium fumarate, calcium lactate, calcium sulfate, calcium tartrate, calcium hydride, calcium nitrite, calcium molybdate, calcium butyrate, calcium isobutyrate, calcium malate, calcium maleate, calcium benzoate, calcium lactate, calcium propionate, calcium carbonate, and any combination thereof.

Embodiment 7: The remineralization composition of any one of Embodiments 1-6, wherein the phosphate is in form of a salt selected from the group consisting of potassium phosphate, sodium phosphate, calcium phosphate and ammonium phosphate.

Embodiment 8: The remineralization composition of any one of Embodiments 1-7, wherein the fluoride is in form of a salt selected from the group consisting of sodium fluoride, potassium fluoride, cesium fluoride, silver fluoride, ammonium fluoride, sodium monofluorophosphate, sodium fluorosilicate, ammonium fluorosilicate, amine fluoride, ammonium fluoride, and any combination thereof.

Embodiment 9: The remineralization composition of any one of Embodiments 1-8, wherein the strontium is in form of a salt selected from the group consisting of strontium acetate, strontium chloride, strontium bromide, strontium nitrate, strontium citrate, strontium formate, strontium acetate, strontium gluconate, strontium ascorbate, strontium lactate, strontium glycinate, strontium carbonate, strontium sulfate, strontium hydroxide, and any combination thereof.

Embodiment 10: The remineralization composition of any one of Embodiments 1-9, wherein the remineralization composition further comprises a buffering agent, optionally in a concentration up to about 150 mM.

Embodiment 11: The remineralization composition of Embodiment 10, wherein the buffering agent is 4-(2-hydroxyethyl)-1 piperazineethanesulfonic acid (HEPES), tris (hydroxymethyl) aminomethane (Tris), citrate, 2-(N 15 morpholino)ethanesulfonic acid (MES), N,N-Bis(2-hydroxyethyl)-2-aminoethanesulfonic acid (BES), 1,3-bis (tris(hydroxymethyl) methylamino)propane (Bis-Tris), 3-(N-morpholino)propanesulfonic acid (MOPS), N,N-bis(2-hydroxyethyl) glycine (Bicine), N-[tris(hydroxymethyl) methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), or any combination thereof.

Embodiment 12: The remineralization composition of any one of Embodiments 1-11, wherein the remineralization composition further comprises a flavoring agent, optionally in an amount up to about 5%, by weight of the composition.

Embodiment 13: The remineralization composition of Embodiment 10, wherein the flavoring agent is spearmint oil, peppermint oil, wintergreen oil, sassafras oil, clove oil, sage oil, eucalyptus oil, poplar oil, cinnamon oil, lemon oil, grape and grapefruit oil, orange peel oil, methyl salicylate and eugenol, clover oil, hay oil, anise oil, eucalyptus, vanilla, menthol, carvone, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones, anethole, or any combination thereof.

Embodiment 14: The remineralization composition of any one of Embodiments 1-13, wherein the remineralization composition further comprises a sweetener, optionally in an amount up to about 3%, by weight of the composition.

Embodiment 15: The remineralization composition of Embodiment 14, wherein the sweetener is sucrose, dextrose, maltose, dextrin, dried invert sugar, fructose, levulose, galactose, corn syrup solids, tagatose, trehalose, sorbitol, mannitol, xylitol, erythritol, glucose, maltose, isomalt, hydrogenated starch hydrolysates, maltitol, sucralose, palatinose, aspartame, NAPM derivatives such as neotame, salts of acesulfame, altitame, saccharin and its salts, cyclamic acid and its salts, glycyrrhizinate, dihydrochalcones, thaumatin, monellin, stevioside, or any combination thereof.

Embodiment 16: The remineralization composition of any one of Embodiments 1-15, wherein the remineralization composition further comprises a surfactant, optionally in an amount up to about 2.5%, by weight of the composition.

Embodiment 17: The remineralization composition of Embodiment 16, wherein the surfactant is an anionic, nonionic, cationic, zwitterionic or amphoteric surfactant.

Embodiment 18: The remineralization composition of Embodiment 17, wherein the surfactant is sodium lauroyl sarcosine, potassium lauroyl sarcosine, aodium coco acylsarcosinate, cocoyl flesh Propylhomoserin potassium, sodium lauroylmethyl taurate, sodium cocoyl methyl sodium taurocholate, sodium lauroyl glutamate, lauryl trimethyl ammonium chloride, stearyl trimethyl ammonium chloride, benzethonium chloride, cetyl pyridinium chloride, cetyl pyridinium chloride benzalkonium chloride, stearyl dimethyl benzyl ammonium chloride, polyoxyethylene lauryl ether sodium sulfate, sodium lauryl sulfate, sodium myristyl sulfate, sodium N-lauroyl sarcosinate, sodium N-myristol sarcosine, sodium dodecylbenzene sulfonate, sodium coconut fatty acid monoglyceride monosulfate, sodium lauryl sulfoacetate, sodium α-olefin sulfonate, sodium N-palmitoyl glutamate, sodium N-methyl-N-acyl taurate, sucrose fatty acid ester, maltose fatty acid ester, maltitol fatty acid ester, lactol fatty acid ester, sorbitan fatty acid ester, polyoxyethylene sorbitan monostearate, polyoxyethylene higher alcohol ether, polyoxyethylene cured Castor oil, polyoxyethylene polyoxypropylene copolymer, polyoxyethylene polyoxypropylene fatty acid ester, polyglycerin fatty acid ester, coconut oil fatty acid amidopropyl betaine, lauryldimethylaminoacetic acid betaine, lauryldimethylamine oxide, 2-alkyl-N-carboxymethyl-N-hydroxyethylimidazolium betaine, N-lauryldiaminoethylglycine, N-myristyldiaminoethylglycine, sodium N-alkyl-1-hydroxyethylimidazoline betaine, or any combination thereof.

Embodiment 19: The remineralization composition of any one of claims 1-18, wherein the remineralization composition further comprises a thickening agent, optionally in an amount up to about 5%, by weight of the composition.

Embodiment 20: The remineralization composition of Embodiment 19, wherein the thickening agent is glycerin, sorbitol, ethylene glycol, propylene glycol, polyethylene glycol, polypropylene glycol, xylitol, maltitol, lactol, carrageenan, sodium carboxymethylcellulose, methylcellulose, sodium hydroxyethylcellulose, sodium alginate, tragacanth gum, karaya gum, arabiya gum, locust bean gum, polyvinyl alcohol, sodium polyacrylate, carboxyvinyl polymer, carbopol, silica gel, aluminum silica gel, Bee gum, laponite, thickening silica, or any combination thereof.

Embodiment 21: The remineralization composition of any one of Embodiments 1-20, wherein the remineralization composition further comprises an anti-calculus agent, optionally in an amount up to about 15%, by weight of the composition.

Embodiment 22: The remineralization composition of Embodiment 21, wherein the anti-calculus agent is selected from the group consisting of pyrophosphate salts, polyaminopropanesulfonic acid (AMPS), hexametaphosphate salts, zinc citrate trihydrate, polypeptides, polyolefin sulfonates, polyolefin phosphates, diphosphonates, and any combination thereof.

Embodiment 23: The remineralization composition of any one of Embodiments 1-22, wherein the remineralization composition further comprises a dental abrasive agent, optionally in an amount up to about 50%, by weight of the composition.

Embodiment 24: The remineralization composition of Embodiment 23, wherein the dental abrasive agent is silica, silicon dioxide, aluminium oxide, aluminium hydroxide, sodium aluminosilicate, sodium metaphosphate, magnesium carbonate, calcium carbonate, calcium bicarbonate, calcium phosphate, calcium sulphate, calcium hydrogen phosphate, dicalcium diphosphate dehydrate, tricalcium phosphate, calcium pyrophosphate, or any combination thereof.

Embodiment 25: The remineralization composition of any one of Embodiments 1-24, wherein the remineralization composition further comprises a binder, optionally in an amount up to about 10%, by weight of the composition.

Embodiment 26: The remineralization composition of claim 25, wherein the binder is carboxymethyl cellulose, hydroxyethyl cellulose, hydroxypropyl cellulose, carbopol, polyacrylate, sodium polyacrylate, carrageenan, sodium alginate, calcium alginate, sodium calcium alginate, pectin, tragant gum, Arabic gum, guar gum, carrage gum, locust bean gum, gellan gum, tamarind gum, psyllium seed gum, polyvinyl alcohol, sodium chondroitin sulfate, methoxyethylene maleic anhydride copolymer, or any combination thereof.

Embodiment 27: The remineralization composition of any one of Embodiments 1-26, wherein the remineralization composition further comprises a coloring agent, optionally in an amount up to about 0.75%, by weight of the composition.

Embodiment 28: The remineralization composition of Embodiment 27, wherein the coloring agent is selected from the group consisting of red, blue and green food coloring (such as FD and C-type dyes and lakes, for example D&C blue #1, D&C blue #4, D&C brown #1, D&C green #5 through #8, D&C orange #4 through #11, D&C yellow #2 through #11, D&C red #6 through #40, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3); carmine, fruit and vegetable extracts, and any combination thereof.

Embodiment 29: The remineralization composition of any one of Embodiments 1-28, wherein the remineralization composition further comprises a preservative, optionally in an amount up to about 3%, by weight of the composition.

Embodiment 30: The remineralization composition of Embodiment 29, wherein the preservative is selected from the group consisting of benzalkonium chloride, benzethonium chloride, benzoic acid, sodium benzoate, p-hydroxybenzoic acid, methyl p-hydroxybenzoate, benzyl alcohol, bronopol, cetrimide, cetylpyridinium chloride, chlorhexidine, chlorobutanol, chlorocresol, chlorocylenol, ethanol, glycerin, hexetidine, imidourea, phenol, phenoxyethanol, phenylethyl alcohol, phenyl mercuric nitrate, propylene glycol, sodium propionate, thimerosyl, methyl paraben, ethyl paraben, butyl paraben, isobutyl paraben, benzyl paraben, citric acid, trisodium citrate, sorbic acid, dichlorinated phenol, phumeotassium sorbate, and any combination thereof.

Embodiment 31: The remineralization composition of any one of Embodiments 1-30, wherein the remineralization composition further comprises a humectant, optionally in an amount up to about 50%, by weight of the composition.

Embodiment 32: The remineralization composition of Embodiment 31, wherein the humectant is selected from the group consisting of glycerol, sorbitol, propylene glycol, glycerin, 1,3-butylene glycol, 1,2-hexanediol, 1,2-octanediol, low molecular weight polyethylene glycols, and any combination thereof.

Embodiment 33: The remineralization composition of any one of Embodiments 1-32, wherein the remineralization composition further comprises a pH adjusting agent in an amount sufficient to adjust the pH of the composition to between from about 6 to about 8.

Embodiment 34: The remineralization composition of any one of Embodiments 1-33, wherein the calcium is a calcium chloride salt, the phosphate is a potassium phosphate salt, the fluoride is a sodium fluoride salt, and the strontium is a strontium acetate salt.

Embodiment 35: The remineralization composition of any one of Embodiments 1-34, wherein the remineralization composition is formulated as a solution, gel, suspension, slurry, paste, or varnish.

Embodiment 36: The remineralization composition of any one of Embodiments 1-35, wherein the remineralization composition is formulated as an oral care composition.

Embodiment 37: The remineralization composition of any one of Embodiments 1-36, wherein the remineralization composition is formulated as a mouthrinse, toothpaste, chewing gum or lozenge.

Embodiment 38: The remineralization composition of any one of Embodiments 1-37, wherein the remineralization composition is present in a delivery device.

Embodiment 39: The remineralization composition of Embodiment 38, wherein the delivery device is a night guard, bleach tray, sticky stripe, or microencapsulate with micro-pump.

Embodiment 40: A method of remineralizing a damaged dental surface, the method comprising applying to the damaged dental surface an effective amount of a remineralization composition of any one of Embodiments 1-37.

Embodiment 41: Use of a remineralization composition of any one of Embodiments 1-37 for remineralization a damaged dental surface.

Embodiment 42: The method of Embodiment 40 or use of Embodiment 41, wherein the damaged dental surface comprises demineralization, decay, abrasion, superficial to moderate fractures, and/or Non-Cavitated Caries Lesions (NCCL).

Embodiment 43: A method for dentin tube occlusion or sealing, tooth desensitization, root canal sealing, enamel hardening, or fissure filling, the method comprising applying and effective amount of a remineralization composition of any one of Embodiments 1-37 to a tooth in need thereof.

Embodiment 44: Use of a remineralization composition of any one of Embodiments 1-37 for dentin tube occlusion or sealing, tooth desensitization, root canal sealing, enamel hardening, and/or fissure filling.

Aspects of the present technology can be defined in any of the following lettered embodiments:

Embodiment A: A remineralization composition comprising: (a) calcium in a concentration from about 0.1 mM to about 500 mM; (b) phosphate in a concentration from about 0.1 mM to about 100 mM; and (c) fluoride in a concentration from about 0.2 ppm to about 300 ppm, wherein the composition has a pH of from about 6 to about 8, and an ionic strength of from about 50 mM to about 500 mM, and wherein the remineralization composition further comprises: (i) strontium in a concentration about 0.05 ppm to about 300 ppm; or (ii) stannous in a concentration from about 0.1 ppm to about 50 ppm.

Embodiment B: The remineralization composition of Embodiment A, wherein the remineralization composition comprises sodium ions.

Embodiment C: The remineralization composition of Embodiment B, wherein the remineralization composition comprises sodium ions in a concentration from about 100 mM to about 300 mM.

Embodiment D: The remineralization composition of any one of Embodiments A-C, wherein the remineralization composition further comprises magnesium and/or zinc, optionally in a concentration from about 1 ppm to about 50 ppm.

Embodiment E: The remineralization composition of Embodiment D, wherein the magnesium is in form of a salt selected from the group consisting of magnesium chloride, magnesium acetate, magnesium benzoate, magnesium citrate, magnesium formate, magnesium hexafluorosilicate, magnesium hydroxide, magnesium lactate, magnesium molybdate, magnesium nitrate, magnesium perchlorate, magnesium phosphonate, magnesium salicylate, magnesium sulfate, magnesium sulfite, and any combination thereof, or zinc is in form of a salt selected from the group consisting of zinc oxide, zinc acetate, zinc borate, zinc nitrate, zinc sulfate, zinc chloride, zinc chlorate, zinc bromide, zinc nitrate, zinc hydrophosphite, zinc oxalate, zinc oleate, zinc peroxide, zinc citrate, zinc gluconate, zinc malate, zinc tartrate, zinc carbonate, zinc phosphate, zinc molybdate, zinc chromate, zinc arsenite, zinc arsenate octahydrate), zinc bromide dehydrate, zinc citrate dihydrate, zinc cyanide, zinc fluoride, zinc hexafluorosilicate, zinc iodide, zinc methacrylate, zinc nitrate hydrate, zinc oxalate hydrate, zinc perchlorate hexahydrate, zinc selenite, zinc sulfate heptahydrate, zinc tetrafluoroborate hydrate, zinc p-toluenesulfonate hydrate, and any combination thereof.

Embodiment F: The remineralization composition of any one of Embodiments A-E, wherein the composition is supersaturated.

Embodiment G: The remineralization composition of any one of Embodiments A-F, wherein the composition exhibits synergistic remineralization activity.

Embodiment H: The remineralization composition of any one of Embodiments A-G, wherein the calcium is in form of a salt selected from the group consisting of calcium chloride, calcium acetate, calcium bromide, calcium fluoride, calcium iodide, calcium gluconate, calcium sulfate, calcium phosphate, calcium glycerophosphate, calcium borate, calcium carbonate, calcium oxalate, calcium citrate, calcium formate, calcium fumarate, calcium lactate, calcium sulfate, calcium tartrate, calcium hydride, calcium nitrite, calcium molybdate, calcium butyrate, calcium isobutyrate, calcium malate, calcium maleate, calcium benzoate, calcium lactate, calcium propionate, calcium carbonate, and any combination thereof.

Embodiment I: The remineralization composition of any one of Embodiments A-H, wherein the phosphate is in form of a salt selected from the group consisting of potassium phosphate, sodium phosphate, calcium phosphate and ammonium phosphate.

Embodiment J: The remineralization composition of any one of Embodiments A-I, wherein the fluoride is in form of a salt selected from the group consisting of sodium fluoride, potassium fluoride, cesium fluoride, silver fluoride, ammonium fluoride, sodium monofluorophosphate, sodium fluorosilicate, ammonium fluorosilicate, amine fluoride, ammonium fluoride, and any combination thereof.

Embodiment K: The remineralization composition of any one of Embodiments A-J, wherein the strontium is in form of a salt selected from the group consisting of strontium acetate, strontium chloride, strontium bromide, strontium nitrate, strontium citrate, strontium formate, strontium acetate, strontium gluconate, strontium ascorbate, strontium lactate, strontium glycinate, strontium carbonate, strontium sulfate, strontium hydroxide, and any combination thereof, or the stannous is in form of a salt selected from the group consisting of tin fluoride, tin chloride, tin bromide, tin iodide, tin cyanide and tin isothiocyanide, tin nitrate, tin sulfate, tin phosphate, and any combination thereof.

Embodiment L: The remineralization composition of any one of Embodiments A-K, wherein the remineralization composition comprises strontium in a concentration from about 20 ppm to about 150 ppm or the remineralization composition comprises stannous in a concentration from about 0.5 ppm to about 5 ppm.

Embodiment M: The remineralization composition of any one of Embodiments A-L, wherein the remineralization composition further comprises a buffering agent, optionally in a concentration up to about 150 mM.

Embodiment N: The remineralization composition of Embodiment M, wherein the buffering agent is 4-(2-hydroxyethyl)-1 piperazineethanesulfonic acid (HEPES), tris (hydroxymethyl) aminomethane (Tris), citrate, 2-(N 15 morpholino)ethanesulfonic acid (MES), N,N-Bis(2-hydroxyethyl)-2-aminoethanesulfonic acid (BES), 1,3-bis (tris(hydroxymethyl) methylamino)propane (Bis-Tris), 3-(N-morpholino)propanesulfonic acid (MOPS), N,N-bis(2-hydroxyethyl) glycine (Bicine), N-[tris(hydroxymethyl) methyl]glycine (Tricine), N-2-acetamido-2-iminodiacetic acid (ADA), N-(2-acetamido)-2-aminoethanesulfonic acid 20 (ACES), piperazine-1,4-bis(2-ethanesulfonic acid) (PIPES), or any combination thereof.

Embodiment 0: The remineralization composition of any one of Embodiments A-O: wherein the remineralization composition further comprises a flavoring agent, optionally in an amount up to about 5%, by weight of the composition.

Embodiment P: The remineralization composition of Embodiment 0, wherein the flavoring agent is spearmint oil, peppermint oil, wintergreen oil, sassafras oil, clove oil, sage oil, eucalyptus oil, poplar oil, cinnamon oil, lemon oil, grape and grapefruit oil, orange peel oil, methyl salicylate and eugenol, clover oil, hay oil, anise oil, eucalyptus, vanilla, menthol, carvone, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones, anethole, or any combination thereof.

Embodiment Q: The remineralization composition of any one of Embodiments A-P, wherein the remineralization composition further comprises a sweetener, optionally in an amount up to about 3%, by weight of the composition.

Embodiment R: The remineralization composition of Embodiment Q, wherein the sweetener is sucrose, dextrose, maltose, dextrin, dried invert sugar, fructose, levulose, galactose, corn syrup solids, tagatose, trehalose, sorbitol, mannitol, xylitol, erythritol, glucose, maltose, isomalt, hydrogenated starch hydrolysates, maltitol, sucralose, palatinose, aspartame, NAPM derivatives such as neotame, salts of acesulfame, altitame, saccharin and its salts, cyclamic acid and its salts, glycyrrhizinate, dihydrochalcones, thaumatin, monellin, stevioside, or any combination thereof.

Embodiment 5: The remineralization composition of any one of Embodiments A-R, wherein the remineralization composition further comprises a surfactant, optionally in an amount up to about 2.5%, by weight of the composition.

Embodiment T: The remineralization composition of Embodiment 5, wherein the surfactant is an anionic, non-ionic, cationic, zwitterionic or amphoteric surfactant.

Embodiment U: The remineralization composition of Embodiment T, wherein the surfactant is sodium lauroyl sarcosine, potassium lauroyl sarcosine, sodium coco acyl-sarcosinate, cocoyl flesh Propylhomoserin potassium, sodium lauroylmethyl taurate, sodium cocoyl methyl sodium taurocholate, sodium lauroyl glutamate, lauryl trimethyl ammonium chloride, stearyl trimethyl ammonium chloride, benzethonium chloride, cetyl pyridinium chloride, cetyl pyridinium chloride benzalkonium chloride, stearyl dimethyl benzyl ammonium chloride, polyoxyethylene lauryl ether sodium sulfate, sodium lauryl sulfate, sodium myristyl sulfate, sodium N-lauroyl sarcosinate, sodium N-myristol sarcosine, sodium dodecylbenzene sulfonate, sodium coconut fatty acid monoglyceride monosulfate, sodium lauryl sulfoacetate, sodium α-olefin sulfonate, sodium N-palmitoyl glutamate, sodium N-methyl-N-acyl taurate, sucrose fatty acid ester, maltose fatty acid ester, maltitol fatty acid ester, lactol fatty acid ester, sorbitan fatty acid ester, polyoxyethylene sorbitan monostearate, polyoxyethylene higher alcohol ether, polyoxyethylene cured Castor oil, polyoxyethylene polyoxypropylene copolymer, polyoxyethylene polyoxypropylene fatty acid ester, polyglycerin fatty acid ester, coconut oil fatty acid amidopropyl betaine, lauryldimethylaminoacetic acid betaine, lauryldimethylamine oxide, 2-alkyl-N-carboxymethyl-N-hydroxyethylimidazolium betaine, N-lauryldiaminoethylglycine, N-myristyl-diaminoethylglycine, sodium N-alkyl-1-hydroxyethylimidazoline betaine, or any combination thereof.

Embodiment V: The remineralization composition of any one of Embodiments A-U, wherein the remineralization composition further comprises a thickening agent, optionally in an amount up to about 5%, by weight of the composition.

Embodiment W: The remineralization composition of Embodiment V, wherein the thickening agent is glycerin, sorbitol, ethylene glycol, propylene glycol, polyethylene glycol, polypropylene glycol, xylitol, maltitol, lactol, carrageenan, sodium carboxymethylcellulose, methylcellulose, sodium hydroxyethylcellulose, sodium alginate, tragacanth gum, karaya gum, arabiya gum, locust bean gum, polyvinyl alcohol, sodium polyacrylate, carboxyvinyl polymer, carbopol, silica gel, aluminum silica gel, Bee gum, laponite, thickening silica, or any combination thereof.

Embodiment X: The remineralization composition of any one of Embodiments A-W, wherein the remineralization composition further comprises an anti-calculus agent, optionally in an amount up to about 15%, by weight of the composition.

Embodiment Y: The remineralization composition of Embodiment X, wherein the anti-calculus agent is selected from the group consisting of pyrophosphate salts, polyaminopropanesulfonic acid (AMPS), hexarnetaphosphate salts, zinc citrate trihydrate, polypeptides, polyolefin sulfonates, polyolefin phosphates, diphosphonates, and any combination thereof.

Embodiment Z: The remineralization composition of any one of Embodiments A-Y, wherein the remineralization composition further comprises a dental abrasive agent, optionally in an amount up to about 50%, by weight of the composition.

Embodiment AA: The remineralization composition of Embodiment Z, wherein the dental abrasive agent is silica, silicon dioxide, aluminum oxide, aluminum hydroxide, sodium aluminosilicate, sodium metaphosphate, magnesium carbonate, calcium carbonate, calcium bicarbonate, calcium phosphate, calcium sulphate, calcium hydrogen phosphate, dicalcium diphosphate dehydrate, tricalcium phosphate, calcium pyrophosphate, or any combination thereof.

Embodiment AB: The remineralization composition of any one of Embodiments A-AA, wherein the remineralization composition further comprises a binder, optionally in an amount up to about 10%, by weight of the composition.

Embodiment AC: The remineralization composition of Embodiment AB, wherein the binder is carboxymethyl cellulose, hydroxyethyl cellulose, hydroxypropyl cellulose, carbopol, polyacrylate, sodium polyacrylate, carrageenan, sodium alginate, calcium alginate, sodium calcium alginate, pectin, tragant gum, Arabic gum, guar gum, carrage gum, locust bean gum, gellan gum, tamarind gum, psyllium seed gum, polyvinyl alcohol, sodium chondroitin sulfate, methoxyethylene maleic anhydride copolymer, or any combination thereof.

Embodiment AD: The remineralization composition of any one of Embodiments A-AC, wherein the remineralization composition further comprises a coloring agent, optionally in an amount up to about 0.75%, by weight of the composition.

Embodiment AE: The remineralization composition of Embodiment AD, wherein the coloring agent is selected from the group consisting of red, blue and green food coloring (such as FD and C-type dyes and lakes, for example D&C blue #1, D&C blue #4, D&C brown #1, D&C green #5 through #8, D&C orange #4 through #11, D&C yellow #2 through #11, D&C red #6 through #40, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3); carmine, fruit and vegetable extracts, and any combination thereof.

Embodiment AF: The remineralization composition of any one of Embodiments A-AE, wherein the remineralization composition further comprises a preservative, optionally in an amount up to about 3%, by weight of the composition.

Embodiment AG: The remineralization composition of Embodiment AF, wherein the preservative is selected from the group consisting of benzalkonium chloride, benzethonium chloride, benzoic acid, sodium benzoate, p-hydroxybenzoic acid, methyl p-hydroxybenzoate, benzyl alcohol, bronopol, cetrimide, cetylpyridinium chloride, chlorhexidine, chlorobutanol, chlorocresol, chlorocylenol, ethanol, glycerin, hexetidine, imidourea, phenol, phenoxyethanol, phenylethyl alcohol, phenyl mercuric nitrate, propylene glycol, sodium propionate, thimerosyl, methyl paraben, ethyl paraben, butyl paraben, isobutyl paraben, benzyl paraben, citric acid, trisodium citrate, sorbic acid, dichlorinated phenol, phumeotassium sorbate, and any combination thereof.

Embodiment AH: The remineralization composition of any one of Embodiments A-AG, wherein the remineralization composition further comprises a humectant, optionally in an amount up to about 50%, by weight of the composition.

Embodiment AI: The remineralization composition of Embodiment AH, wherein the humectant is selected from the group consisting of glycerol, sorbitol, propylene glycol, glycerin, 1,3-butylene glycol, 1,2-hexanediol, 1,2-octanediol, low molecular weight polyethylene glycols, and any combination thereof.

Embodiment AJ: The remineralization composition of any one of Embodiments A-AI, wherein the remineralization composition further comprises a pH adjusting agent in an amount sufficient to adjust the pH of the composition to between from about 6 to about 8.

Embodiment AK: The remineralization composition of any one of Embodiments A-AI, wherein the calcium is a calcium chloride salt, the phosphate is a potassium phosphate salt, the fluoride is a sodium fluoride salt, and the strontium is a strontium acetate salt; or the calcium is a calcium chloride salt, the phosphate is a potassium phosphate salt, the fluoride is a sodium fluoride salt, and the stannous is a stannous fluoride salt.

Embodiment AL: The remineralization composition of any one of Embodiments A-AJ, wherein the composition comprises calcium ions in a concentration from about 2 mM to about 5 mM, phosphate ions in a concentration from about 0.5 mM to about 5 mM, fluoride ions in a concentration from about 2 ppm to about 20 ppm, and sodium ions in a concentration from about 150 mM to about 200, and wherein the composition has a pH of from about 6.5 to about 7.5 and an ionic strength of from about 150 mM to about 200 mM, and wherein the composition comprises strontium in a concentration from about 10 ppm to about 200 ppm or stannous in a concentration from about 0.1 ppm to about 10 ppm.

Embodiment AM: The composition of any one of Embodiments A-AL, wherein the comprises from about 2 mM to about 3 mM calcium chloride, and about 1 mM to about 2 mM potassium dihydrogen phosphate, and from about 165 mM to about 175 mM sodium chloride, and wherein the composition has a pH of about 7.1 to about 7.4, and the composition further comprises: (a) from about 20 ppm to about 50 ppm strontium acetate and from about 5 ppm to about 15 ppm sodium fluoride; (b) from about 20 ppm to about 30 ppm strontium acetate and from about 5 ppm to about 15 ppm sodium fluoride; or (c) from about 0.1 ppm to about 1 ppm stannous fluoride and from about 1 ppm to about 3 ppm sodium fluoride.

Embodiment AN: The composition of any one of Embodiments A-AM, wherein the comprises from about 2.5 mM calcium chloride, about 1.5 mM potassium dihydrogen phosphate, and from about 170 mM sodium chloride, and wherein the composition has a pH of about 7.3, and the composition further comprises: (a) about 25 ppm strontium acetate and from about 10 ppm sodium fluoride; (b) about 0.5 ppm stannous fluoride and 2 ppm sodium fluoride; (c) about 5 ppm strontium acetate and about 10 ppm sodium fluoride; (d) about 10 ppm strontium acetate and about 5 ppm sodium fluoride; (e) about 10 ppm strontium acetate and about 10 ppm sodium fluoride; (f) about 25 ppm strontium acetate and about 10 ppm sodium fluoride; (g) about 50 ppm strontium acetate and about 10 ppm sodium fluoride; (h) about 10 ppm strontium acetate and about 5 ppm sodium fluoride; (i) about 1 ppm strontium acetate and about 10 ppm sodium fluoride; (j) about 2 ppm strontium acetate and about 5 ppm sodium fluoride; (k) about 2 ppm strontium acetate and about 10 ppm sodium fluoride; (l) about 5 ppm strontium acetate and about 10 ppm sodium fluoride; (m) about 10 ppm strontium acetate and about 10 ppm sodium fluoride; or (n) about 2 ppm strontium acetate and about 5 ppm sodium fluoride.

Embodiment AO: The remineralization composition of any one of Embodiments A-AN, wherein the remineralization composition is formulated as a solution, gel, suspension, slurry, paste, varnish, sealant or cement.

Embodiment AP: The remineralization composition of any one of Embodiments A-AO, wherein the remineralization composition is formulated as an oral care composition.

Embodiment AQ: The remineralization composition of any one of Embodiments A-AP, wherein the remineralization composition is formulated as a mouthrinse, toothpaste, chewing gum or lozenge.

Embodiment AR: The remineralization composition of any one of Embodiments A-AQ, wherein the remineralization composition is formulated for application by a tooth brushing device.

Embodiment AS: The remineralization composition of any one of Embodiments A-AR, wherein the remineralization composition anti-caries activity.

Embodiment AT: The remineralization composition of any one of Embodiments A-AS, wherein the remineralization composition is present in a delivery device.

Embodiment AU: The remineralization composition of Embodiment AT, wherein the delivery device is a night guard, customer tray, sticky stripe, or microencapsulate with micro-pump.

Embodiment AV: A method of remineralizing a damaged dental surface, the method comprising applying to the damaged dental surface an effective amount of a remineralization composition of any one of Embodiments A-AR.

Embodiment AW: Use of a remineralization composition of any one of Embodiments A-AR for remineralization a damaged dental surface.

Embodiment AX: The method of Embodiment AV or use of Embodiment AW, wherein the damaged dental surface comprises demineralization, decay, abrasion, superficial to moderate fractures, Non-Cavitated Caries Lesions (NCCL), tooth fracture and/or tooth discoloration.

Embodiment AY: A method for dentin tube occlusion or sealing, tooth desensitization, root canal sealing, enamel hardening, or fissure filling, the method comprising applying and effective amount of a remineralization composition of any one of Embodiments A-AR to a tooth in need thereof.

Embodiment AZ: Use of a remineralization composition of any one of Embodiments A-AR for dentin tube occlusion or sealing, tooth desensitization, root canal sealing, enamel hardening, and/or fissure filling.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Example 1: Method for Synthetic Enamel Remineralization

The remineralization experimental groups were classified as follows: Enamel remineralization group (Single, Continuous, and Multiple crystal layer), Dentin remineralization group.

Teeth Specimen Preparation: Freshly extracted natural human teeth were used in this study, soaked in 3% sodium hypochlorite at 4° C. Crowns were sectioned longitudinally into 0.5 mm thick slices for enamel and dentin remineralization experimental groups. Buehler Isomet 5000 with a diamond blade was used to section the tooth specimens. Ecomet 250 grinding-polishing machine with 75 um grinding disk was used for polishing the tooth surface. After sectioning and polishing, the teeth specimens were ultrasonic cleaned in water for 5 minutes, and stored in 0.1M phosphate-buffered saline (PBS, pH=7.2) prior use. To mimic early carious lesion, slices were etched using 5% nitric acid (HNO3) or 35% phosphoric acid (H3PO4) for 30-40 seconds and then rinsed thoroughly with deionized water.

Biomimetic Mineralizing Solution (BMS) Preparation: The BMS was prepared using the following formula. Dissolve 174 mM sodium chloride (NaCl, >=99.5%, Fisher), 2.5 mM calcium chloride (CaCl$_2$·2H2O, >=99% Sigma), 1.5 mM potassium dihydrogen phosphate (KH2PO4, >=99%, Sigma), and 50 mM of HEPES (>99%, Sigma) with a final volume of 500 mL and pH of 7.3 adjusted using 1 M hydrochloric (HCl) acid and 1M potassium hydroxide (KOH) at room temperature. The solution was stored in a sealed Pyrex glass bottle for a few hours before use to allow the mineral precursor formation in the supersaturated solution. The solution was stable for up to 30 days under room temperature (18-25 degree Celsius) without precipitation.

Additive ions Stock solution: Fluoride stock solution was 1000 ppm F$^-$ solution made from sodium fluoride (>=99%, Sigma). Strontium stock solution was 5000 ppm Sr$^{2+}$ solution made from strontium acetate (>=40.5% Sr, Sigma).

Remineralization Solution:

The remineralization experimental groups were coded according to the ionic concentration (1, 2, 5, and 10 ppm by weight) added into the BMS follows:

Control group: BMS and PBS

Sr group: Sr5, Sr10, Sr25, and Sr50 (SrX means X ppm of Sr in BMS)

F group F1, F2, F5, and F10 (FX means X ppm of F in BMS)

Sn group Sn 0.2, Sn 0.5, Sn1, Sn2, Sn5 (SnX means X ppm of Sn in BMS)

Sr—F group: Sr10F10, Sr10F5, Sr50F5, Sr10F10, Sr15F10, Sr50F10 (SrXFY means X ppm of Sr and Y ppm of F in BMS)

Sn—F group: Sr0.5F1, Sn1F1, Sn2F2, Sr0.5F2, Sn1F2 (SnXFY means X ppm of Sn and Y ppm of F in BMS)

Prior to enamel growth experiment the desired concentration of the Sr and F ions was added in each BMS from the stock solution. Such remineralization solution was stable for 6-10 days.

Synthetic enamel growth through remineralization process: Tooth slice specimens with acid etched surface were submerged into 12 mL enamel growth solution and stored in the sealed vial under 37° C. Celsius then retrieved after 24 hrs or other designated intervals, and rinsed with deionized water. For the multiple layered crystal growth, remineralizing solution was refreshed every 24 hrs for 6 days. For the continuous crystal growth, the remineralization was in a large volume (30 mL or 60 mL) of remineralizing solution for 3-6 days, but not refreshed daily.

Analysis

Microstructure analysis: Specimens were mounted on aluminum stubs using graphite double-sided tape and gold-palladium sputter coated, then observed by a Hitachi SU6600 Scanning Electron Microscopy (SEM) using secondary electron and backscattering electron detectors.

Tooth slice specimens were prepared in two orientations. 1) Horizontal view (top view) was used to study crystal layer top structure, packing density, morphology, as well as the horizontal coverage of crystal layer. Tooth slice were mounted horizontally, facing the treated surface up. 2) Cross-section view (vertical view) was used to observe the thickness of the layer, interface between the tooth substrate and continuous grown layers, density of the synthetic layer, and crystal orientation. For the observation of the thickness of crystal growth on the tooth substrate, a notch on the tooth slice were made by a diamond bur, and the mechanical facture was made to form a vertical fracture surface through substrate and regrown layers. Then the facture surface was mounted on SEM stub facing up. The cross-section view on dentin substrate also provided the information on sealing, occlusion, and crystal penetration depth within the dentinal tubules.

Elemental Composition Microanalysis: Specimens without sputter coating was analyzed under the variable pressure mode of SEM. The elemental compositions of the crystals were analyzed by EDS (energy dispersive spectrometer). The atomic ratio of calcium (Ca) and phosphorus (P) were calculated to match the theoretical ratio of different calcium phosphates minerals.

Mineral density: The crystal mineral density was analyzed by a qualitative Backscattering Electron (qBSE) technique. Tooth slice specimens with regrown enamel layer were mounted vertically and embedded in epoxy resin together with a pure aluminum and graphite parallel references. The embedded specimens were polished using an Ecomet 250 grinding-polishing machine to expose the testing surface of tooth slice alongside with aluminum and graphite surfaces. The specimen surface was polished down to 0.5 micrometer with diamond grinding disks, and analyzed by backscattering detector under variable pressure mode without a sputter coating. The BSE images were obtained on the specimens and reference materials under exactly same imaging condition. The grayscales of aluminum and graphite on images were measured using Image-J and plotted against the theoretical z-values of graphite and aluminum. Then the z values of different regions of the teeth were then calculated and compared. The grayscale and z-values from qBSE techniques represents the mineral density similar to that of X-ray transmission radiography.

Microhardness: For the cross-section surface hardness, tooth specimens after treatment were embedded, polished, and then analyzed for Vicker's hardness values using a Buehler Micromet 2003 hardness tester using 25 grams load with 15-second loading time. Seven to ten indentations were made on each interested areas, native enamel, etched enamel and remineralized enamel.

For the top surface hardness test, the tooth slabs were embedded in epoxy resin and polished to expose enamel surface. After acid etching as previous described, the specimens were submerged in designated solution with proper ionic concentration. After 3 days' incubation, the specimens were taken out and the hardness were tested on the treated surface.

Nanoindentation test: Tooth specimens with synthetic enamel layer after treatment were embedded, polished, and then tested with a Bruker Hystron Nanoindenter using a Berkovich 10 um radius conospherical tip with 1 mN load for 10 seconds. The nanoindentation hardness and elastic modulus was then calculated from the loading and unloading curve.

Crystallography: The crystallography of the regrown crystals were determined by X-ray diffraction (XRD) and selected area electron diffraction (SAED) under transmission electron microscope (TEM).

The X-ray diffraction (XRD) on uncoated tooth surface were analyzed by a diffractometer (D8 discover, Bruker AXS GmbH., Karlsruhe, Germany) with Cu-K$\alpha$1 radiation ($\lambda$=1.5405981 Å, 40 kV and 40 mA). The XRD patterns were obtained in the 2θ angle range between 3° and 50°. The crystallographic phases were determined by the Rietveld refinement employing GSAS-II software. The full-profile fitting was implemented by referencing the standard data of $Ca_5(PO_4)_3OH$ (hydroxyapatite, HAP, JCPDS No. 9-432) and $Ca_8H_2(PO_4)_6(H_2O)_5$ (octocalcium phosphate, OCP, JCPDS No. 26-1056).

For TEM specimen preparation, the regrown crystals were scraped by a razor blade from a remineralized tooth surface and grinded with agar pestle and mortar with 2 mL 200 proof ethanol, then transferred into Eppendorf tube and ultra-sonicated for two minutes to disperse crystal aggregation, then the suspension was dropped on a carbon Formvar supported TEM copper grid. The SAED analysis were performed using a TEM (JEOL JEM 1400 Flash TEM) under 120 kV. The diffraction rings were measured using Image J and match the d-spacing with standard data of $Ca_5(PO_4)_3OH$ (HAP, JCPDS No. 9-432).

Results are shown in FIGS. 3-14 and 16A-24B. The results in FIGS. 3-14 and 16A-24B show the characterizations of the synthetic enamel prepared from the novel mineralization composition. The results indicate the synthetic enamel layer can be formed on either natural enamel, or dentin surface. The microstructure and composition of needle like densely packed nano-hydroaxapatite crystals are very close to the natural enamel. The newly formed synthetic enamel layer shows no gap to enamel and dentin substrate, indicating the potential of rebuilding enamel and dentin-enamel junction. The needle-like crystals form and penetrate in the dentin tubules. The elongated hydroxyapatite nanocrystals grown inside the dentin tubules at the near-surface area are inter-crossed and occlude the dentin tubules completely. The synthetic enamel layer shows a high mineral density and hardness similar to natural enamel, and shows the capability of continuous growth with extended thickness.

The synthetic enamel formed using the exemplary remineralization composition has one or more of the following characteristics:

a. the very similar mineral density as the substrate enamel shown from backscattering electron micrographic imaging;

b. the same hierarchical structure as the natural enamel with densely packed nanorod crystals shown under secondary electron micrographic imaging;

c. the similar elemental composition with a similar calcium phosphate ratio to natural enamel;
d. a seamless interface fully integrated with substrate structure of enamel and dentin, and continuous growth;
e. highly-orientated hydroxyapatite phases, the same as the natural enamel crystal analyzed by X-ray diffraction; and
f. similar to or higher hardness than natural enamel analyzed by Vickers and nanoindentation microhardness.

Figure 29A:
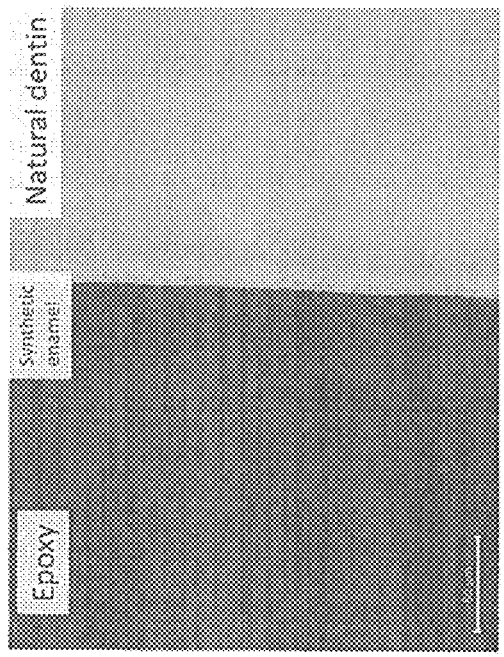
FIGS. 29A-29B examine the nanoidentation hardness of synthetic enamel layer.
Figure 29B:
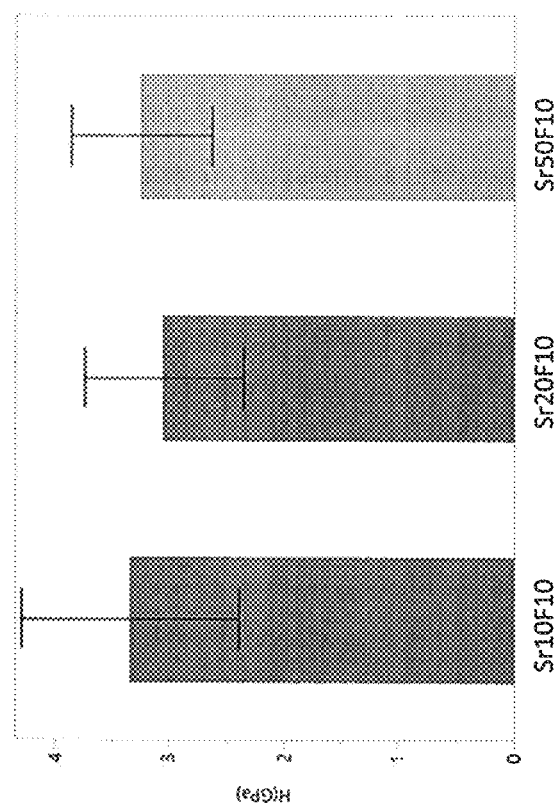
Figure 30F:
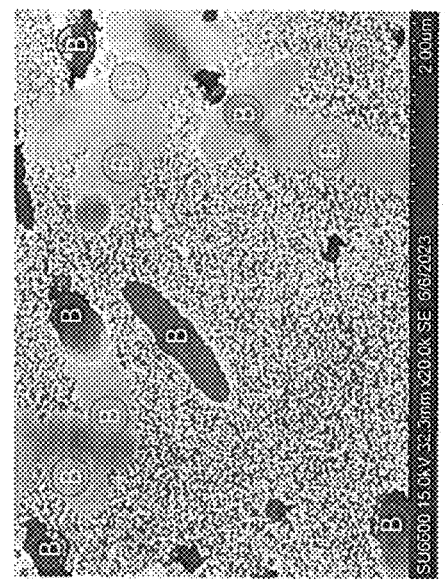
FIGS. 30D-30F show higher magnification 20,000× of the same samples in FIG. 30A-30C. Circle with B indicates the dried bacteria and circle with B indicates the void space left by bacteria.
Figure 30E:
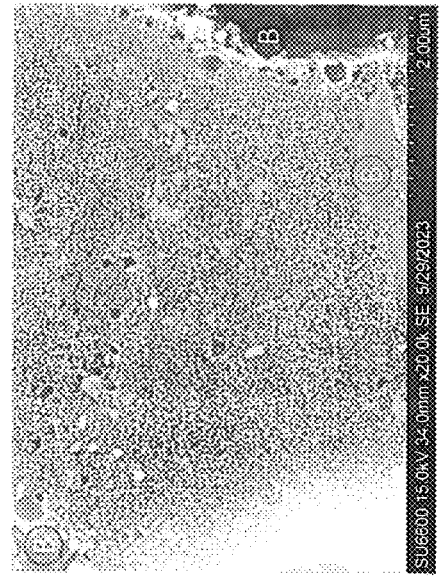
Figure 30D:
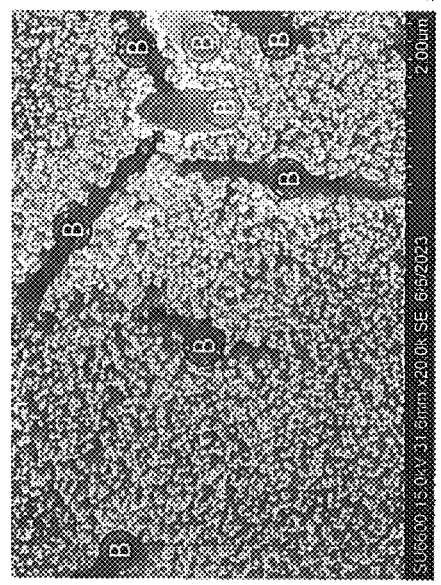
Figure 31:
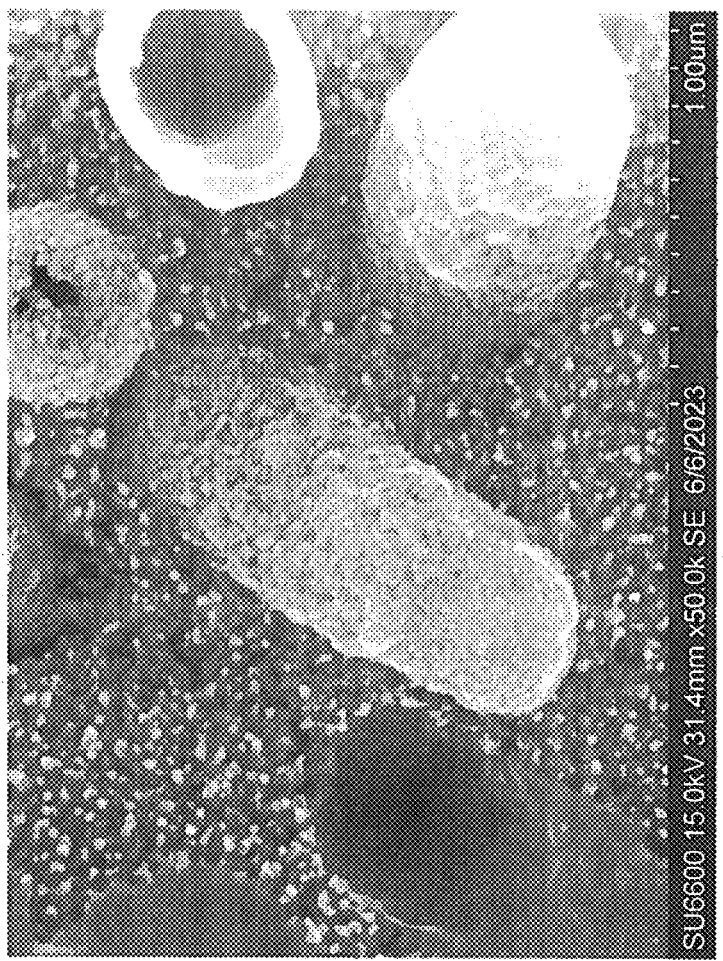
FIG. 31 shows higher magnification 50,000× of *Escherichia coli* bacteria embedded in synthetic enamel crystals after the remineralization process in the presences of 10$^5$/mL bacteria.
Figure 32B:
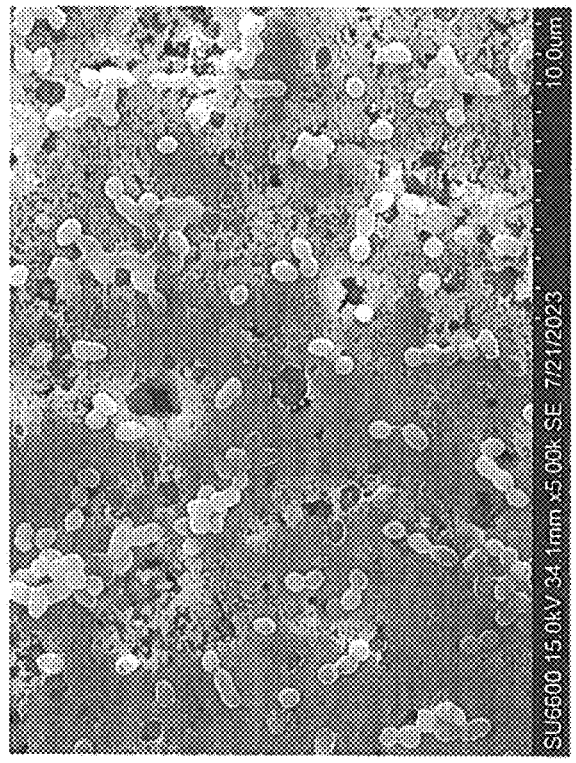
FIGS. 32A-32B examine synthetic enamel crystal growth in the presence of *Enterococcus faecalis* bacteria on dentin surface.
Figure 32A:
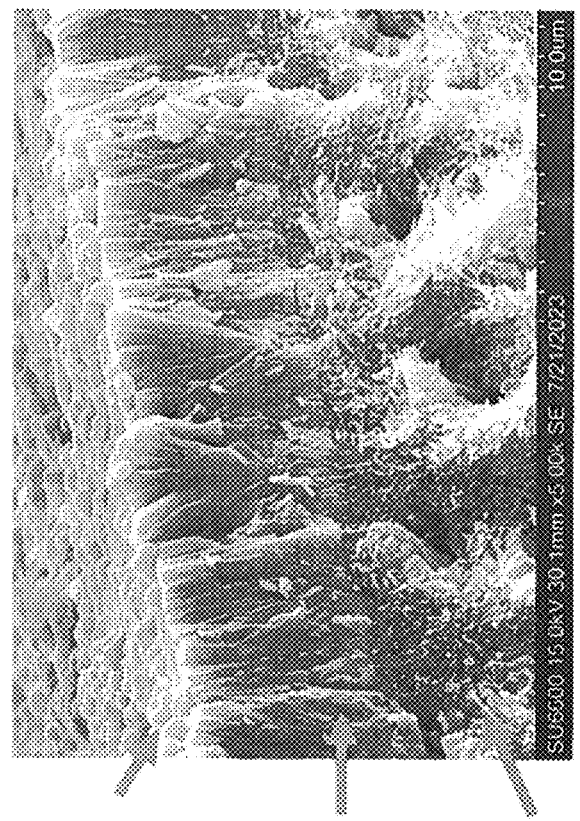

Additionally, using an exemplary composition with strontium and fluoride, the interface hardness by nanoindenter of synthetic enamel and natural dentin was tested as 3.63±1.28 GPa, the interface hardness of synthetic enamel and natural enamel was 3.27±0.27 GPa, synthetic enamel layer over dentin was 2.99±0.30 GPa, and synthetic enamel over enamel was 3.66±0.79 GPa (FIGS. 29A-29B). The natural healthy human enamel hardness our lab tested is 3.32±1.17 GPa and dentin harness is 0.78±0.19 GPa.

Example 2

Synthetic enamel layer can be grown on top of enamel and dentin in the presence of Tin (II) and fluoride ions (FIGS. 25A-25D). The base solution composition is 2.5 mM $CaCl_2$) and 1.5 mM $KH_2PO_4$ in 50 mM HEPES and 170 mM NaCl at pH=7.3. For FIGS. 25A and 25C, 0.5 ppm $SnF_2$ and 2 ppm NaF were added in the base solution. In other experiments (FIGS. 25B and 25D), the specimens were made from a mixed solution with added 25 ppm Strontium (Strontium Acetate) and 10 ppm Fluoride (NaF).

Figure 26B:
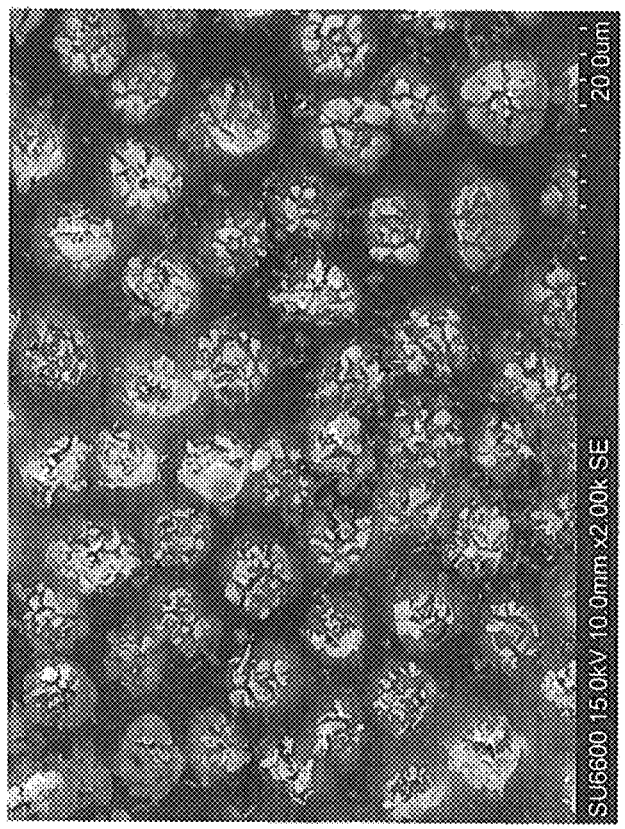
FIGS. 26A-26B examine dentin tubule occlusion.
Figure 26A:
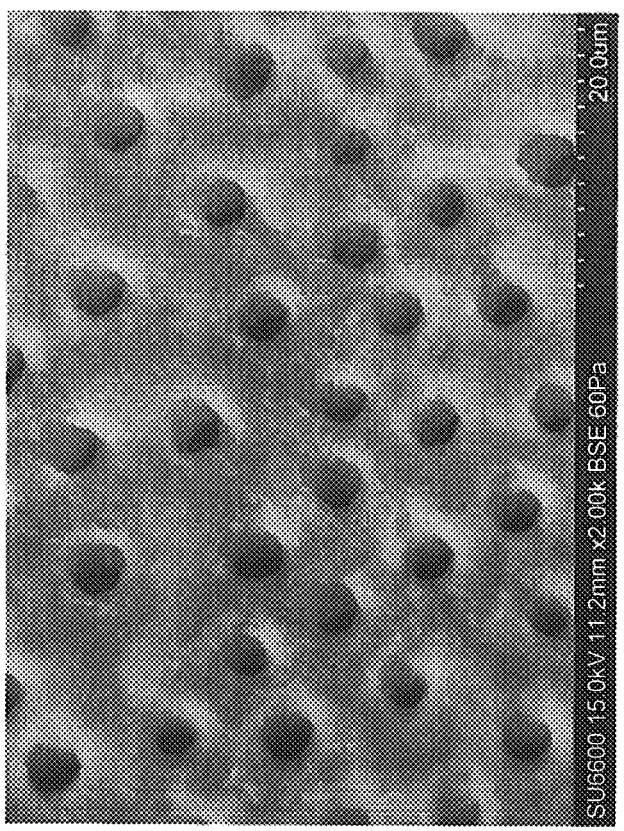
Figure 27B:
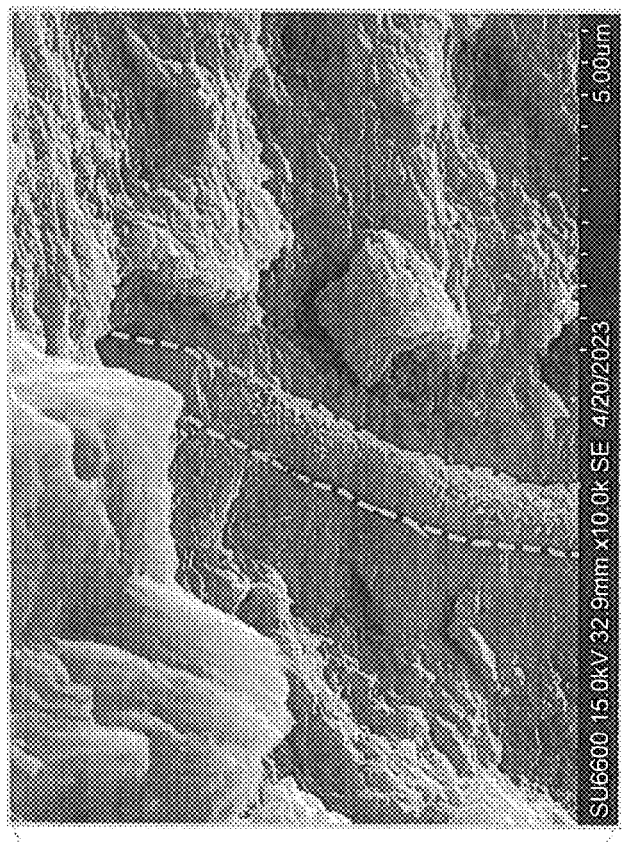
FIGS. 27A-27B depict crystal tags plugs formed into dentin tubules on cross-section surface at 1,000× magnification (FIG. 27A) and 10,000× magnification (FIG. 27B). The dotted line indicates a crystal plug formed in a dentin tubule.
Figure 27A:
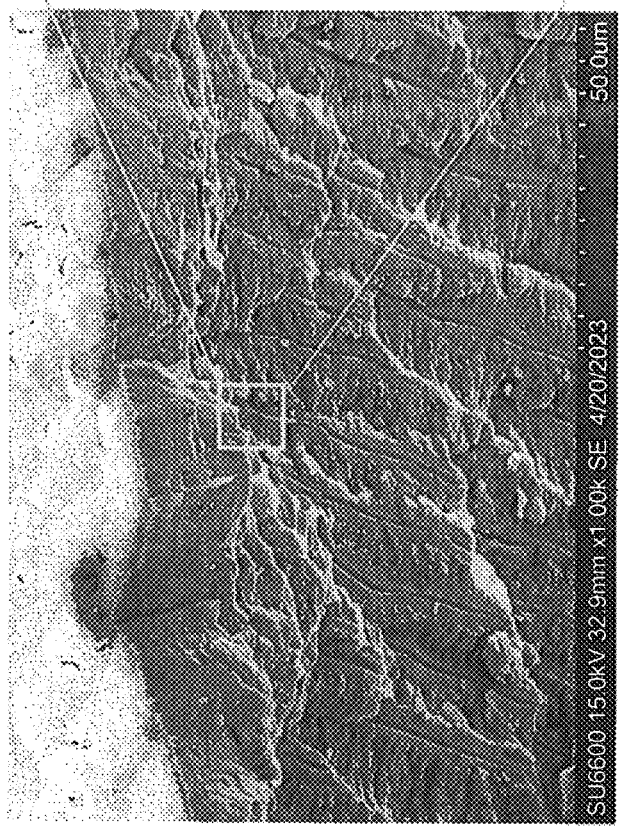
Figure 28:
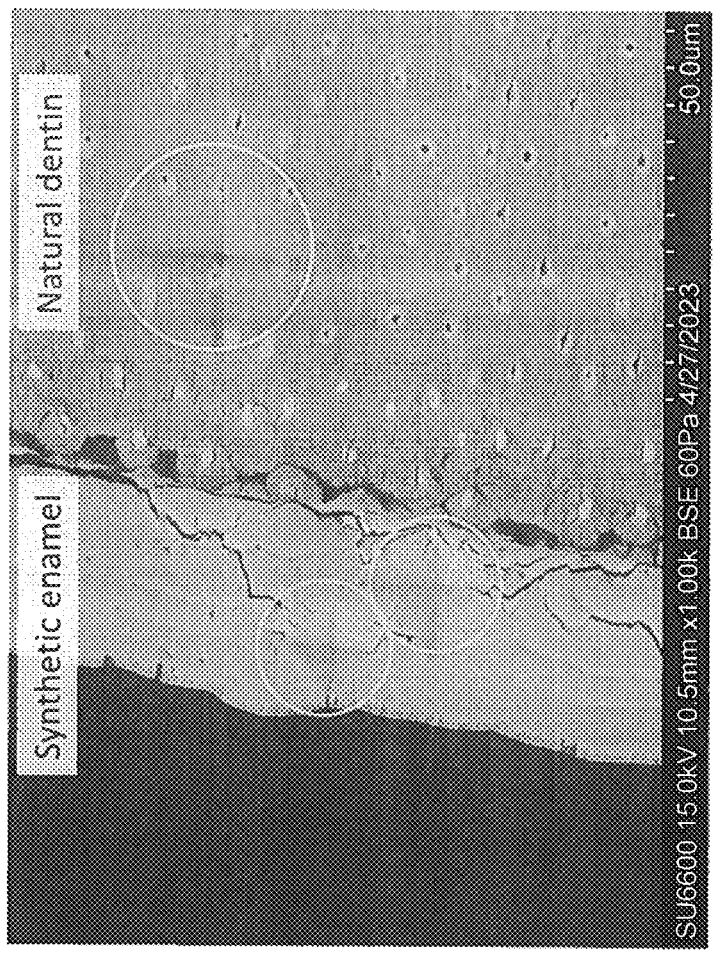
FIG. 28 examines the hardness of remineralization layer formed on etched dentin surface. The Vickers hardness of the underneath dentin is $66.7 \pm 4.5$ kg/mm$^2$ and the synthetic enamel layer is $238.7 \pm 53.4$ kg/mm$^2$ and the polished cross-section shows the treated dentin with indentations.

The dentin tubules on the surface have been fully occluded after the 24 hours of treatment with a modified composition in the presence of strontium and fluoride ions (FIGS. 26A-27).

Synthetic enamel can be grown in the presence of bacteria (FIGS. 30A-32B) after being exposed to microbes in the air, *Escherichia coli*, oral bacterial mix, and/or *Enterococcus faecalis*.

Figure 33B:
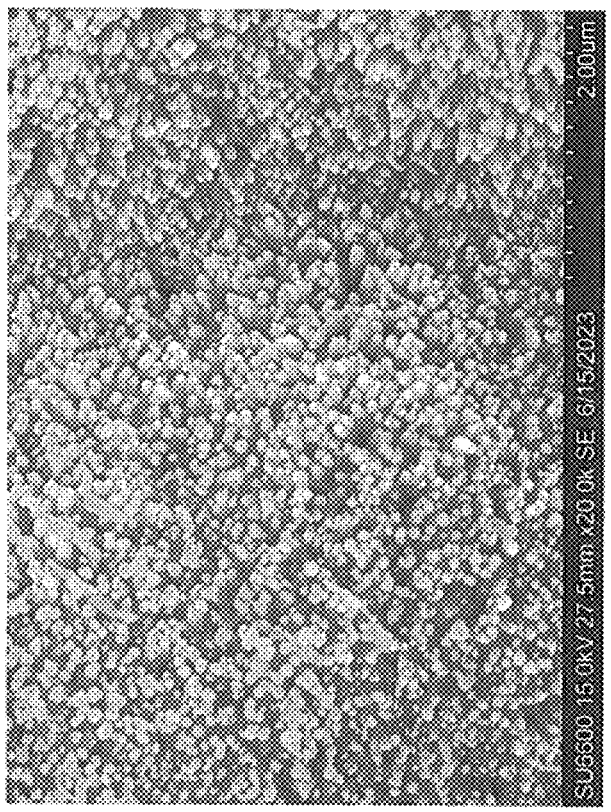
FIGS. 33A-33B show synthetic enamel formation in the presence of *Escherichia coli* and antiseptics, 100 ppm cetylpyridinium chloride (CPC).
Figure 33A:
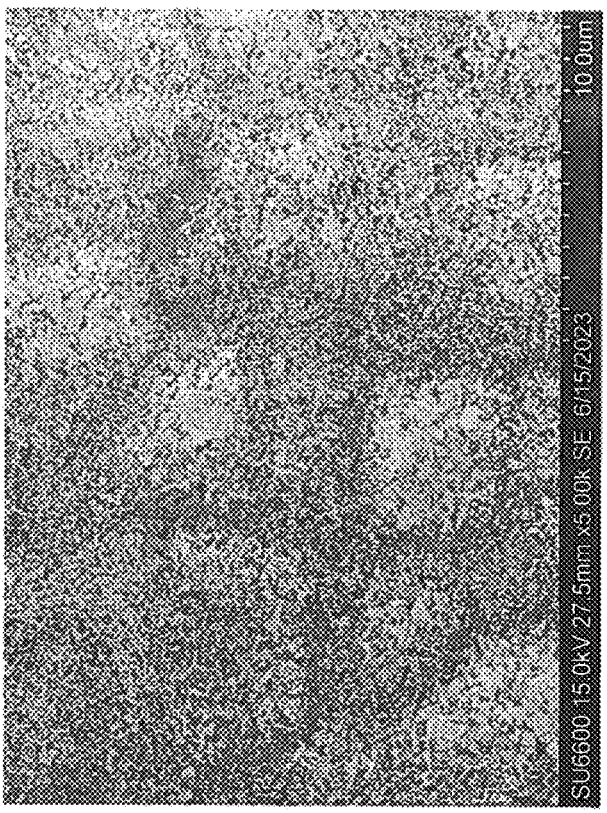

Synthetic enamel can be grown in the presence of antiseptics CPC (cetylpyridinium chloride) (FIGS. 33A-33B).

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:
1. A remineralization composition comprising:
a. calcium in a concentration from about 0.1 mM to about 500 mM;
b. phosphate in a concentration from about 0.1 mM to about 100 mM; and
c. fluoride in a concentration from about 0.2 ppm to about 300 ppm, wherein the composition has a pH of from no less than 7.1 to about 8, and an ionic strength of from about 50 mM to about 500 mM, and wherein the remineralization composition further comprises: (i) strontium in a concentration about 0.05 ppm to about 300 ppm; or (ii) stannous in a concentration from about 0.1 ppm to about 50 ppm.

2. The remineralization composition of claim 1, wherein the remineralization composition comprises sodium ions.

3. The remineralization composition of claim 2, wherein the remineralization composition comprises sodium ions in a concentration from about 100 mM to about 300 mM.

4. The remineralization composition of claim 1, wherein the composition further comprises magnesium or zinc, optionally in a concentration from about 1 ppm to about 50 ppm.

5. The remineralization composition of claim 4, wherein the magnesium is in form of a salt selected from the group consisting of magnesium chloride, magnesium acetate, magnesium benzoate, magnesium citrate, magnesium formate, magnesium hexafluorosilicate, magnesium hydroxide, magnesium lactate, magnesium molybdate, magnesium nitrate, magnesium perchlorate, magnesium phosphonate, magnesium salicylate, magnesium sulfate, magnesium sulfite, and any combination thereof; or stannous is in form of a salt selected from the group consisting of tin fluoride, tin chloride, tin bromide, tin iodide, tin cyanide and tin isothiocyanide, tin nitrate, tin sulfate, tin phosphate, and any combination thereof; or zinc is in form of a salt selected from the group consisting of zinc oxide, zinc acetate, zinc borate, zinc nitrate, zinc sulfate, zinc chloride, zinc chlorate, zinc bromide, zinc nitrate, zinc hydrophosphite, zinc oxalate, zinc oleate, zinc peroxide, zinc citrate, zinc gluconate, zinc malate, zinc tartrate, zinc carbonate, zinc phosphate, zinc molybdate, zinc chromate, zinc arsenite, zinc arsenate octahydrate, zinc bromide dehydrate, zinc citrate dihydrate, zinc cyanide, zinc fluoride, zinc hexafluorosilicate, zinc iodide, zinc methacrylate, zinc nitrate hydrate, zinc oxalate hydrate, zinc perchlorate hexahydrate, zinc selenite, zinc sulfate heptahydrate, zinc tetrafluoroborate hydrate, zinc p-toluenesulfonate hydrate, and any combination thereof.

6. The remineralization composition of claim 1, wherein the composition is supersaturated.

7. The remineralization composition of claim 1, wherein the composition exhibits synergistic remineralization activity.

8. The remineralization composition of claim 1, wherein the calcium is in form of a salt selected from the group consisting of calcium chloride, calcium acetate, calcium bromide, calcium fluoride, calcium iodide, calcium gluconate, calcium sulfate, calcium phosphate, calcium glycerophosphate, calcium borate, calcium carbonate, calcium oxalate, calcium citrate, calcium formate, calcium fumarate, calcium lactate, calcium sulfate, calcium tartrate, calcium hydride, calcium nitrite, calcium molybdate, calcium butyrate, calcium isobutyrate, calcium malate, calcium maleate, calcium benzoate, calcium lactate, calcium propionate, calcium carbonate, and any combination thereof.

9. The remineralization composition of claim 1, wherein the phosphate is in form of a salt selected from the group consisting of potassium phosphate, sodium phosphate, calcium phosphate and ammonium phosphate.

10. The remineralization composition of claim 1, wherein the fluoride is in form of a salt selected from the group consisting of sodium fluoride, potassium fluoride, cesium fluoride, silver fluoride, ammonium fluoride, sodium monofluorophosphate, sodium fluorosilicate, ammonium fluorosilicate, amine fluoride, ammonium fluoride, and any combination thereof.

11. The remineralization composition of claim 1, wherein the strontium is in form of a salt selected from the group consisting of strontium acetate, strontium chloride, strontium bromide, strontium nitrate, strontium citrate, strontium formate, strontium acetate, strontium gluconate, strontium ascorbate, strontium lactate, strontium glycinate, strontium carbonate, strontium sulfate, strontium hydroxide, and any combination thereof.

12. The remineralization composition of claim 1, wherein the remineralization composition further comprises a buffering agent, flavoring agent, sweetener, surfactant, thickening agent, anti-calculus agent, dental abrasive agent, binder, coloring agent, preservative, or humectant.

13. The remineralization composition of claim 1, wherein the remineralization composition further comprises a pH adjusting agent in an amount sufficient to adjust the pH of the composition to between from no less than 7.1 to about 8.

14. The remineralization composition of claim 1, wherein the calcium is a calcium chloride salt, the phosphate is a potassium phosphate salt, the fluoride is a sodium fluoride salt, and the strontium is a strontium acetate salt; or the calcium is a calcium chloride salt, the phosphate is a potassium phosphate salt, the fluoride is a sodium fluoride salt, and the stannous is a stannous fluoride salt.

15. The remineralization composition of claim 1, wherein the composition comprises calcium ions in a concentration from about 2 mM to about 5 mM, phosphate ions in a concentration from about 0.5 mM to about 5 mM, fluoride ions in a concentration from about 2 ppm to about 20 ppm, and sodium chloride in a concentration from about 150 mM to about 200 mM, and wherein the composition has a pH of from no less than 7.1 to about 7.8 and an ionic strength of from about 150 mM to about 200 mM, and wherein the composition comprises strontium in a concentration from about 10 ppm to about 200 ppm or stannous in a concentration from about 0.1 ppm to about 10 ppm, optionally, the composition comprises from about 2 mM to about 3 mM calcium chloride, about 1 mM to about 2 mM potassium dihydrogen phosphate, and from about 165 mM to about 175 mM sodium chloride, and wherein the composition has a pH of from no less than 7.1 to about 7.4, and the composition further comprises: (i) from about 20 ppm to about 30 ppm strontium acetate and from about 5 ppm to about 15 ppm sodium fluoride; or (ii) from about 0.1 ppm to about 1 ppm stannous fluoride and from about 1 ppm to about 3 ppm sodium fluoride.

16. The remineralization composition of claim 1, wherein the remineralization composition is formulated as a solution, gel, suspension, slurry, paste, varnish, sealant or cement.

17. The remineralization composition of claim 1, wherein the remineralization composition is formulated as an oral care composition or for application by a tooth brushing device.

18. The remineralization composition of claim 1, wherein the remineralization composition is present in a delivery device, optionally, the delivery device is a night guard, customer tray, aligner, sticky strip, or microencapsulate with micro-pump.

19. A method of remineralizing a damaged dental surface, the method comprising applying to the damaged dental surface an effective amount of a remineralization composition of claim 1, optionally the damaged dental surface comprises demineralization, decay, abrasion, superficial to moderate fractures, Non-Carious Cervical Lesions (NCCL), tooth fracture or tooth discoloration.

20. A method for dentin tube occlusion or sealing, tooth desensitization, root canal sealing, enamel hardening, or fissure filling, the method comprising applying and effective amount of a remineralization composition of claim 1 to a tooth in need thereof.

21. The remineralization composition of claim 1, wherein the remineralization composition comprises sodium chloride, potassium chloride, potassium nitrate, or ammonium chloride.

22. The remineralization composition of claim 1, wherein the remineralization composition comprises sodium chloride.

* * * * *